(12) United States Patent
Wank

(10) Patent No.: US 6,706,493 B2
(45) Date of Patent: Mar. 16, 2004

(54) DNA ENCODING A CHOLECYSTOKININ RECEPTOR

(75) Inventor: Steven A. Wank, Bethesda, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 87 days.

(21) Appl. No.: 09/443,745

(22) Filed: Nov. 19, 1999

(65) Prior Publication Data

US 2003/0055238 A1 Mar. 20, 2003

Related U.S. Application Data

(60) Division of application No. 08/029,170, filed on Mar. 10, 1993, now Pat. No. 6,169,173, which is a continuation-in-part of application No. 07/937,609, filed on Sep. 2, 1992, now Pat. No. 5,319,073, which is a continuation-in-part of application No. 07/928,033, filed on Aug. 11, 1992, now abandoned, which is a continuation-in-part of application No. 07/861,769, filed on Apr. 1, 1992, now abandoned, which is a continuation-in-part of application No. 07/831,248, filed on Feb. 7, 1992, now abandoned.

(51) Int. Cl.$^7$ .......................... C12P 21/06; C12N 1/20; C12N 5/00; C12N 5/06; C07H 21/04
(52) U.S. Cl. .................. 435/69.1; 435/252.3; 435/325; 536/23.1; 536/23.5
(58) Field of Search ................ 536/23.5, 23.1; 435/320.1, 325, 252.3, 69.1; 530/350

(56) References Cited

U.S. PATENT DOCUMENTS

| | | |
|---|---|---|
| 4,675,285 A | 6/1987 | Clark et al. |
| 4,985,352 A | 1/1991 | Julius et al. |

FOREIGN PATENT DOCUMENTS

| | | |
|---|---|---|
| WO | WO 92/20814 | 11/1992 |

OTHER PUBLICATIONS

Bork, P. (1996), Go hunting in sequence databases but watch out for the traps. Trends Genetics, 12(10):425–427.*
Bork, P. (1998), Powers and Pitfalls in Sequence Analysis: The 70% Hurdle. Genome Res., 10:398–400, esp. p. 400.*
Brenner, S. (1999) Errors in genome annotation, Trends in Genetics, 15(4): 3–4, esp. Fig. 2.*
Doerks, T. (1998), Protein annotation: detective work for function prediction., Trends Genetics. 14(6):248–250.*
Smith, et al. (1997) Nature Biotech. 15: 1222–1223.*
Baldwin et al., *J. Biol. Chem.*, 261, 12252–12257 (1986).
Chemer et al., "Functionally Distinct Receptors for Cholecystokinin and Gastrin on Dispersed Chief Cells from Guinea Pig Stomach," *Gastrointest. Liver Physiol.*, 17, G151–155 (1988).

Dufresne et al., "Purification of A–subtype Pancreatic Cholecystokinin Receptor by Immunoaffinity Chromatography," *Biochimie*, 74, 149–151 (1992).
Duong et al., "Purification and Characterization of Rat Pancreatic Cholecystokinin Receptor," *J. Biol. Chem.*, 264(30), 17990–17996 (1989).
Grider et al., "Distinct Receptors for Cholecystokinin and Gastrin on Muscle Cells of Stomach and Gallbladder," *Gastrointest. Liver Physiol.*, 22, G184–190 (1990).
Knapp et al., "A New Highly Selective CCK–B Receptor Radioligand ($[^3H][N$–methyl–Nle$^{28,31}]CCK_{26-33}$): Evidence for CCK–B Receptor Heterogeneity," *J. Pharm. Exp. Ther.*, 255(3), 1278–1286 (1990).
Kopin et al., "Expression Cloning and Characterization of the Canine Parietal Cell Gastrin Receptor," *PNAS USA*, 89 3605–3609 (1992).
Kopin, "DNA Encoding Gastrin and Cholecytokinin B Receptors Used for Isolating CCK–B Receptor Antagonists for Treating e.g. Pain etc., and Gastrin Receptor Antagonists etc.," Database Patent Family Search of Mar. 10, 1994.
Lowe et al., "Affinity Chromatography on Immobilized Dyes," *Meth. In Ehly*, 104, 97–113 (1984).
Macda, *Ann. Res. Ent.*, 34, 351–377 (1989).
Nash et al., *Nature*, 329, 836–838 (1987).
Pisegna et al., "Molecular Cloning of the Human Brain and Gastric Cholecystokinin Receptor: Structure, Functional Expression and Chromosomal Localization," *Biochemical and Biophysical Research Communications*, 189, No. 1, 296–303 (Nov. 30, 1992).
Roche et al., "Characterization of a Gastrin–Type Receptor on Rabbit Gastric Parietal Cells Using L365, 260 and L364, 718," *Gastrointest. Liver Physiol.*, 23, G182–188 (1991).
Roche et al., "'Gastrin' and 'CCK' Receptors on Histamine– and Somatostatin– Containing Cells from Rabbit Fundic Mucosa–II," *Biochem. Pharmacol.*, 42(4) 771–776 (1991).
Szecowka et al., "Purification of the Pancreatic Cholecystokinin Receptor," *Regulatory Peptides*, 24, 215–224 (1989).
Wank et al., "Brain and Gastrointestinal Cholecystokinin Receptor Family: Structure and Functional Expression," *Proc. Natl. Acad. Sci., U.S.A.*, 89, 8691–8695 (Sep. 1992).
Wank et al., "Purification, Molecular Cloning, and Functional Expression of the Cholecystokinin Receptor from Rat Pancreas," *PNAS USA*, 89, 3125–3129 (Apr. 1992).
Williams et al., *PNAS*, 85, 4939–4943 (1988).

* cited by examiner

*Primary Examiner*—Elizabeth Kemmerer
*Assistant Examiner*—Sandra Wegert
(74) *Attorney, Agent, or Firm*—Leydig, Voit & Mayer, Ltd.

(57) ABSTRACT

An unconventional approach to purifying CCK receptor protein to sequenceable-grade homogeneity has been discovered. By this approach, CCK receptor protein can be obtained and sequenced, routinely from a variety sources, and from the sequence information thus obtained it is possible to prepare oligonucleotides suitable for cloning CCK receptor genes. "CCK receptor" in this context denotes any from a group of proteins that displays a characteristic CCK binding affinity and that is encoded by a nucleotide sequence which hybridizes a oligonucleotide probe designed in accordance with the criteria elaborated herein.

6 Claims, 40 Drawing Sheets

FIG. 1A

```
CCGCAATGCT TGCCCAGATG CTCTGAGAAT GGCGAACTCA AGTTGCCTTT AGGAATGGCT    60
GCAAGCCCA CACCTGGAAA TCTCCCCCTC CCTGCTCCTC CACGGGCAGGT TGCATTGGG    120
AGACCCTGTG ATCATTAGAG GAGAGAGACA GGA ATG AGC CAT TCA CCA GCT CGC    174
                                  Met Ser His Ser Pro Ala Arg
                                   1               5

CAG CAC TTG GTA GAA AGC AGC AGG ATG GAC GTG GTC GAC AGC CTT CTT    222
Gln His Leu Val Glu Ser Ser Arg Met Asp Val Val Asp Ser Leu Leu
         10                  15                  20

ATG AAT GGG AGC AAC ATC ACT CCC CCC TGT GAA CTC GGA CTG GAA AAT    270
Met Asn Gly Ser Asn Ile Thr Pro Pro Cys Glu Leu Gly Leu Glu Asn
         25        ▲        30                  35            ▲

GAG ACG CTT TTC TGC TTG GAT CAA CCT CAA CCT TCA AAA GAG TGG CAG    318
Glu Thr Leu Phe Cys Leu Asp Gln Pro Gln Pro Ser Lys Glu Trp Gln
 40                  45                  50                  55
```

FIG. 1B

```
TCT GCA CTG CAG ATT CTC CTG TAC TCC ATC ATA TTC CTT CTC AGT GTG         366
Ser Ala Leu Gln Ile Leu Leu Tyr Ser Ile Ile Phe Leu Leu Ser Val
                60                  65                  70
                                         ⌐I
CTG GGG AAC ACG CTG GTT ATA ACG CTG ATT CGA AAC AAG AGG ATG             414
Leu Gly Asn Thr Leu Val Ile Thr Leu Ile Arg Asn Lys Arg Met
        75                  80                  85
                                                              ⌐II
CGG ACG GTC ACC AAC ATC TTC CTG CTG TCC CTG GCT GTC AGT GAC CTC         462
Arg Thr Val Thr Asn Ile Phe Leu Leu Ser Leu Ala Val Ser Asp Leu
        90                  95                 100

ATG CTC TGC CTC TTC TGC ATG CCG TTC AAC CTC ATC CCC AAC CTG CTC         510
Met Leu Cys Leu Phe Cys Met[Pro Phe Asn Leu Ile Pro Asn Leu Leu
       105                 110→                115
                                                                ⌐III
AAG GAT TTC ATC TTC GGA AGT GCC GTG TGC AAG ACT ACC ACC TAC TTC         558
Lys Asp Phe Ile Phe Gly Ser Ala Val Cys Lys]ACT[Thr Thr Tyr Phe
       120                 125                 130→        135

ATG GGC ACT TCC GTT TCC ACC TTC AAC CTG GTA GCC ATC TCT                 606
Met Gly Thr Ser Val Ser Thr Phe Asn Leu Val Ala Ile Ser
       140                 145                 150
```

FIG. 1C

```
CTG GAG AGA TAT GGC GCC ATC TGC AGA CCC CTA CAG TCC CGC GTC TGG    654
Leu Glu Arg Tyr Gly Ala Ile]Cys Arg Pro Leu Gln Ser Arg Val Trp
              155              160→           IV        165

CAA ACA AAG TCC CAT GCT GCT TTG AAG GTC ATC GCT GCC ACC TGG TGC CTC    702
Gln Thr Lys Ser His Ala Ala Leu Lys Val Ile Ala Ala Thr Trp Cys Leu
        170                  175                  180

TCC TTT ACC ATC ATG ACT CCG TAC CCC ATT TAC AGC AAC TTG GTG CCT    750
Ser Phe Thr Ile Met Thr Pro Tyr Pro Ile Tyr Ser Asn Leu Val Pro
        185                  190                  195

TTT ACT AAA AAT AAT AAC CAG ACG GCG AAC ATG TGC CGC TTC CTG TTG    798
Phe Thr Lys Asn Asn Asn Gln Thr Ala Asn Met Cys Arg Phe Leu Leu
200                  205▲                 210                 215

CCA AGT GAC GCT ATG CAG TCC TGG CAA ACA TTC CTG CTA CTC ATC    846
Pro Ser Asp Ala Met Gln Ser Trp Gln Thr Phe Leu Leu Leu Ile
        220                  225        V        230
```

FIG. 1D

```
CTC TTT CTT CTC CCT GGG ATT GTG ATG GTG GCC TAC GGG TTG ATC    894
Leu Phe Leu Leu Pro Gly Ile Val Met Val Ala Tyr Gly Leu Ile
235                         240                 245

TCT CTG GAA CTC TAC CAA GGA ATC AAA TTT GAT GCC AGC CAG AAG AAA    942
Ser Leu Glu Leu Tyr Gln Gly Ile Lys Phe Asp Ala Ser Gln Lys Lys
250                         255                 260

TCT GCC AAA GAG AAG AAG CCG AGC ACT GGC AGC AGC AGC CGA TAT GAG    990
Ser Ala Lys Glu Lys Lys Pro Ser Thr Gly Ser Ser Ser Arg Tyr Glu
265                 270                 275                 3

GAT AGT GAT GGC TGT TAC TTG CAG AAG TCC CGG CCC AGG AAG CTG    1038
Asp Ser Asp Gly Cys Tyr Leu Gln Lys Ser Arg Pro Arg Lys Leu
280                     285             290                 295

GAG CTT CAG CAG CTG TCT AGC AGC GGT GGC AGC AGA CTC AAC CGG    1086
Glu Leu Gln Gln Leu Ser Ser Ser Gly Gly Ser Arg Leu Asn Arg
300                         305                 310

ATC AGG AGC AGC AGT TCA GCT GCC AAC CTC ATA GCC AAG AAG CGC GTG    1134
Ile Arg Ser Ser Ser Ala Ala Asn Leu Ile Ala Lys Lys Arg Val
315                         320                 325
                                VI

ATC CGC ATG CTC ATT GTC ATC GTG GTC CTC TTC TTC CTG TGC TGG ATG    1182
Ile Arg Met Leu Ile Val Ile Val Val Leu Phe Phe Leu Cys Trp Met
330                         335                 340
```

FIG. 1E

| | | | | | | | | | | |
|---|---|---|---|---|---|---|---|---|---|---|
|CCC|ATC|TTC|AGC|GCC|AAC|GCC|TGG|CGG|GCA|TAT|GAC|ACG|GTT|TCT|GCC|1230
|Pro|Ile|Phe|Ser|Ala|Asn|Ala|Trp|Arg|Ala|Tyr|Asp|Thr|Val|Ser|Ala|
| | | | |345| | | |350| | | |355| | | | |

```
CCC ATC TTC AGC GCC AAC GCC TGG CGG GCA TAT GAC ACG GTT TCT GCC        1230
Pro Ile Phe Ser Ala Asn Ala Trp Arg Ala Tyr Asp Thr Val Ser Ala
        345                 350                 355

GAG AAG CAC CTC TCA GGG ACT CCC ATC TCC TTC ATC CTC CTC CTC TCC        1278
Glu Lys His Leu Ser Gly Thr Pro Ile Ser Phe Ile Leu Leu Leu Ser
    360                 365                 370                 375

TAC ACC TCC TGT GTT AAC CCC ATC ATC TAT TGC TTC CCT TGT TGC CCG AAT AAA        1326
Tyr Thr Ser Cys Val Asn Pro Ile Ile Tyr Cys Phe Pro Cys Cys Pro Asn Lys
            380                 385                 390

CGC TTT CGC CTG GGC TTC ATG GCC ACC TTC ATG AAC AAA        1374
Arg Phe Arg Leu Gly Phe Met Ala Thr Phe Met Asn Lys
        395                 400                 405

GGT CCC CCA GGG GTG AGA GGA GAG GTG GGA GAG GAT GGG AGG        1422
Gly Pro Pro Gly Val Arg Gly Glu Val Gly Glu Asp Gly Arg
    410                 415                 420

ACC ATA AGG GCA TTG CTG TCC AGG TAT TCC TAC AGC CAC ATG AGC ACC        1470
Thr Ile Arg Ala Leu Leu Ser Arg Tyr Ser Tyr Ser His Met Ser Thr
        425                 430                 435

TCT GCT CCA CCC CCC TGAACTCCAC CTGGTCCACT G        1506
Ser Ala Pro Pro Pro End
    440             445
```

FIG. 2A

```
TGACCCTGCT TGCTCAACTC TACGTCTTGT TTCGTTTCT GTTCTGGCC GTTACAGATC        60

CAAGCTCCTC GAGCCCGGGC TGCAGGAATT CTGCGGCCGC CGCTTAGCAG AGCTAAGTGG       120

GACTTCACTG GAGCC ATG GAG CTG CTC AAG CTG CTC AAC CGC AGC GTG CAG GGA   171
              Met Glu Leu Leu Lys Leu Leu Asn Arg Ser Val Gln Gly
               1                 5                        ▲    10

CCA GGA CCC GGG TCG GGG TCT TCT TTG TGC CCG GGT GTC TCC CTT            219
Pro Gly Pro Gly Ser Gly Ser Ser Leu Cys Arg Gly Pro Val Ser Leu
         15                      20                      25

CTC AAC AGC AGT AGT GCC GGG AAC CTC AGC TGT GAC CCC CCT CGT ATC        267
Leu Asn Ser Ser Ser Ala Gly Asn Leu Ser Cys Asp Pro Pro Arg Ile
 30                      35 ▲                     40

CGC GGA ACC GGG ACC AGA GAA TTG ATG GCG ATT AGA ATC ACC CTT            315
Arg Gly Thr Gly Thr Arg Glu Leu Met Ala Ile Arg Ile Thr Leu
     45                      50                     55           60

TAT GCA GTG ATC TTT CTG ATG AGT GTT GGC GGA AAC GTG CTC ATC ATC        363
Tyr Ala Val Ile Phe Leu Met Ser Val Gly Gly Asn Val Leu Ile Ile
             65                      70                      75

GTG GTC CTG GGA CTG AGC CGA CGC CTA AGA ACG GTC ACC AAC GCC TTC        411
Val Val Leu Gly Leu Ser Arg Arg Leu Arg Thr Val Thr Asn Ala Phe
         80                      85                      90
```

FIG. 2B

```
CTG CTC TCC CTG GCA GTC AGC GAC CTC CTG CTG GCC GTG GCT TGC ATG      459
Leu Leu Ser Leu Ala Val Ser Asp Leu Leu Leu Ala Val Ala Cys Met
             95                         100                    105

CCC TTC ACA CTC CTG CCC AAC CTC ATG GGC ACA TTC ATC TTC GGC ACA      507
Pro Phe Thr Leu Leu Pro Asn Leu Met Gly Thr Phe Ile Phe Gly Thr
             110                        115                    120

GTC ATC TGC AAG GCC ATT TCC TAC CTC ATG GGG GTA TCA GTG AGT GTA      555
Val Ile Cys Lys Ala Ile Ser Tyr Leu Met Gly Val Ser Val Ser Val
             125                        130                    135                140

TCC ACT CTA AAT CTC GTG GCC ATA GCC CTG GAG CGA TAC AGC GCC ATC      603
Ser Thr Leu Asn Leu Val Ala Ile Ala Leu Glu Arg Tyr Ser Ala Ile
             145                        150                    155

TGC CGA CCA CTG CAA GCA CGA GTA TGG CAA ACA CGC TCC CAC GCT          651
Cys Arg Pro Leu Gln Ala Arg Val Trp Gln Thr Arg Ser His Ala Ala
             160                        165                    170

CGG GTG ATC TTA GCC ACG TGG CTG CTG TCT GGA CTT ATG GTA CCC          699
Arg Val Ile Leu Ala Thr Trp Leu Leu Ser Gly Leu Met Val Pro
             175                        180                    185
```

FIG. 2C

```
TAC CCT GTG TAC ACC ATG GTA CAG CCA GTG GGA CCT CGA GTG CTG CAG       747
Tyr Pro Val Tyr Thr Met Val Gln Pro Val Gly Pro Arg Val Leu Gln
190                 195                 200

TGC ATG CAT CGC TGG CCC AGT GCA CGT GTC CAA CAA ACC TGG TCC GTG       795
Cys Met His Arg Trp Pro Ser Ala Arg Val Gln Gln Thr Trp Ser Val
205                 210                 215                 220
  •                                                    V

CTA CTG CTT CTT TTG TTC ATC CCG GGT GTG GTT ATT GCG GTG GTG           843
Leu Leu Leu Leu Phe Ile Pro Gly Val Val Ile Ala Val
                225                 230                 235

GCC TAT GGA CTC ATC TCC CGC GAA CTC TAC CTA GGA CTC CAC TTT GAT       891
Ala Tyr Gly Leu Ile Ser Arg Glu Leu Tyr Leu Gly Leu His Phe Asp
                240                 245                 250
        ▲
       255

GGT GAA AAT GAC AGC GAG ACC CAA AGC CGG GCC CGA AAC CAA GGG GGC       939
Gly Glu Asn Asp Ser Glu Thr Gln Ser Arg Ala Arg Asn Gln Gly Gly
                        260                 265

CTG CCG GGT GGG GCA GCA CCA GGG CCT GTC CAC CAG AAC GGG GGC TGC       987
Leu Pro Gly Gly Ala Ala Pro Gly Pro Val His Gln Asn Gly Gly Cys
270                 275                 280
```

FIG. 2D

```
CGG CCT GTA ACC AGC GTA GCT GGG GAA GAC AGT GAT GGC TGT GTG    1035
Arg Pro Val Thr Ser Val Ala Gly Glu Asp Ser Asp Gly Cys Val
285                 290                 295                 300

CAA CTT CCG CGT TCC CGA CTG GAG ATG ACA ACG CTA ACC ACA CCC ACT   1083
Gln Leu Pro Arg Ser Arg Leu Glu Met Thr Thr Leu Thr Thr Pro Thr
            305                 310                 315

CCT GGG CCA GTC CCT GGC CCT CGG CCC AAC CAG GCC AAG CTG GCT     1131
Pro Gly Pro Val Pro Gly Pro Arg Pro Asn Gln Ala Lys Leu Ala
        320                 325                 330
                                                    ⌐ II

AAG AAG CGG GTG GTG CGA ATG CTA GTG ATT GTT TTG CTT TTC TTC    1179
Lys Lys Arg Val Val Arg Met Leu Val Ile Val Leu Leu Phe Phe
            335                 340                 345

CTG TGT TGG CTG CCA GTG TAC AGC GTC AAC ACG TGG CGC GCC TTC GAT   1227
Leu Cys Trp Leu Pro Val Tyr Ser Val Asn Thr Trp Arg Ala Phe Asp
350                 355                 360
```

FIG. 2E

```
GGC CCA GGC GCA CAA CGA GCA CTC TCA GGG GCC CCT ATC TCT TTC ATC      1275
Gly Pro Gly Ala Gln Arg Ala Leu Ser Gly Ala Pro Ile Ser Phe Ile
365                 370                 375                 380
                                         |———— VII ————
CAC TTG CTG AGC TAC GTC TCT GCT TGT GTC AAC CCC CTG GTC TAC TGT      1323
His Leu Leu Ser Tyr Val Ser Ala Cys Val Asn Pro Leu Val Tyr Cys
        385                 390                 395

TTC ATG CAC CGC CGC TTC CGC CAG GCC TGC CTG GAC ACA TGT GCC CGC      1371
Phe Met His Arg Arg Phe Arg Gln Ala Cys Leu Asp Thr Cys Ala Arg
            400                 405                 410

TGT TGC CCA CGC CCT CCA CGA GCT CGA CCA CAG CCT CTT CCA GAT GAG      1419
Cys Cys Pro Arg Pro Pro Arg Ala Arg Pro Gln Pro Leu Pro Asp Glu
 •          415                 420                 425

GAT CCT ACC CCC TCC ATC ATC GCT TCG CTG TCC AGG CTA AGC TAT ACC      1467
Asp Pro Thr Pro Ser Ile Ile Ala Ser Leu Ser Arg Leu Ser Tyr Thr
        430                 435                 440

ACC ATC AGC ACA CTG GGG CCT GGC TGAGGGGTTG GGAGATTGGA GAAAGAGACA     1521
Thr Ile Ser Thr Leu Gly Pro Gly End
            445                 450
```

FIG. 2F

```
AGATACATAA TTACTATCAA ATGACCCATC CAAACACATA AGAAACAAAA TTCAGAATTA  1581
ATCAGGTGAA CACCCAACAC CATGGACAGA CCCCTACACA CAGAAAATAG TATCTTTGCT  1641
GCCCTACCTG AAACAGATAG GAGTCTCATA GGAAAGGAGG CTCACTTCTG ATAAGGGGCT  1701
GAGTCCCTTC CTAGACATCT TGCACTGACC CCATTACATG GACAGACACA AGGTCCGTAG  1761
CAGTAAACTT TACCTATAAA GGGGAACTCT GACAAGGGCT GATTGGCTCC TCATATGAAC  1821
ATATTACTGA CACTATTCTG TAGTGCCCAT AGCCTAGTGC AGAAGTGACT TAGGACATTG  1881
TGGCTGTTCC CGTTTGACTT CATTATGCC TTCCTCATCC AGCCTGAAA TTATCAACCA   1941
CACGCCTTTC ACCTTTCGGA GCTGCCGATC GTTCAGCACT CTTCCCTCCT GCCTCTCCTC  2001
TCCTTTCCAT TGGAGACTGT GGAAAGTCCC CTTCCCTCCT GCCTCTCCTC CCTCACCAGA  2061
CCACATCATA AAAGGATAAG TGACTTAGTG TCCTCCTGGA CTTCTTGAGG TAGGTGAACA  2121
GGTGTGGTTT ATGGGAAGCT TCTTCATTTA TTGGCTCCCA TGACTAATCT ACCCCATATC  2181
CAACCTTGTG CAAAAAGGCC AGGGTATGAA GATAGGGATG AGCGTACCCT CTCTTGGTTG  2241
TC                                                                2243
```

FIG. 3A

```
RCCKBR  ..........MELLKLNRSVQGPGPGSGSSLCRPGVSLLNSS..SAGNLSCDPPRL..RGTGTRELEMAIRIILYAVIFLMSVLGGNVLIIVLGLS   82
RCCKAR  ..........MSHSPARQHLVESSRMDVVDSLLMNGSNITPPCELGLENRTLFCLDQPQPSKEWQSALQILLYSIIFLLSVLGNTLVTVLIRN        84
MGRPR   ..........MAPNNCSHLNLDVDPFLS  CNDTFNQSLSPPKMDNWFHPGFIY..........VTPAVYGLIIVGLIGNTLLKIFCTV           69
RNMBR   ..........MPPRSLPNISLPTEASESELEPEVWENDFLPDSDGTTAELVHC..........VIPSLYLIIISVGLLGNMLVRIFLTN           71
RSKR    ......................MGTRAIVSDANILSGLESNATGVTAFSMPGWQLALWATAYLALVLVAVTGNATVWIILAH                  61
RSPR    ......................MDNVLPMDSDLFPNISTRVTSESNQFVQPTWQIVLWAAAYTVIVTSVGNVVVIWIILAH                   60
RNMKR   MASVPRGENWTDGTVEVGTHTGNLSSALGVTEWLALQAGNFSSALGLPATTQAPSQVRANLITNQFVQPSWRIALWSLAYGLWAVAVPGNLIVIWIILAH 100
                                                                                     ──I──

RCCKBR  RRLRTVTNAFLLSLAVSDLLLAVACMPFTLLPNLMGTFIFGTVICKAISYLMGVSVSVSTLNLVAIALERYSAICRPLQARVWQTRSHAARVILATWLLS 182
RCCKAR  KRMRTVTNIFLLSLAVSDLMLCLFCMPFNLIPNLLKDFIFGSAVCKITTYFMGTSVSVSTFNLVAISLERYGAICRPLQSRVWQTKSHALKVIAATWCLS 184
MGRPR   KSMRNVPNLFISSLALGDLLLLLVTCAPVDASKYLADRWLFGRIGCKLIPFIQLTSVGVSVFTLTALSADRYKAVRPMDIQAASHALMKICLKAALIWTVS 169
RNMBR   STMRSVPNFISNLAAGDLLLLLTCVPVDASRYFFDEWVFGKLGCKLIPPAIQLTSVGVSVFTLTALSADRYRAIVNPMDMQTSGVVLWTSLKAVGIWVVS  171
RSKR    ERMRTVTNYFIINLALADLCMAAFNATENFIYASHNIWYFGRAFCYFQNLFPITAMFVSIYSMTAIAADRYMAIVHPFQPRLSAPSTKA..IIAGIWLVA  159
RSPR    KRMRTVTNYFLVNLAFAEACMAAFNTVVNFTYAVHNVWYYGLFYCKFHNFFPIAALFASIYSMTAVAFDRYMAIIHPLQPRLSATATKV..VIFVIWVLA  158
RNMKR   KRMRTVTNYFLVNLAFSDASVAAFNTLINFIYGLHSEWYFGANYCRFQNFFPITAVFASIYSMTALAVDRYMAIIDPLKPRLSATATKI    VIGSIWILA 198
                      ──II──                                    ──III──                            ──V──

RCCKBR  GLLMVPYPVYTMVQP...VGPRVLQCMHRWPSARVQQ..TW..SVLILLLLFFIPGVVIAVAYGLISRELYL  GLHFDGENDSFTQSRARNQGGIPGGAA 274
RCCKAR  FTMTPYPIYSNLVPFTKNNNQTANMCRFLLPSDAMQQ..SW..QTFLLILFLLPGIVMVVAYGLISLELYQ..CIKFDASQKKSAKEKKPSTGS       274
MGRPR   MLLAIPEAVFSDLHPFHVKDTNQTFISCAPYPHSNELH..PKIHSMASFLVFYVIPLAIISVYYYFIARNLLQSAYNLPVEGNIHVKK            255
RNMBR   VLLAVPEAVFSEVARIGSSD  NSSSTACIPYPQTDELH..PKIHSVLIFLVFYFLIPLVIISIYYYHLAKTLIRSAHNLPGEYNEHTKK          256
RSKR    LALASPQCFYSTI...TVDEGATKCVVAWPNDNGGKMLLLYHLVVFVLIYFLPLLVMFGAYSVIGLTLWKRAVPRHQAHGA                    237
RSPR    LLLAFFQGYYSTT...ETMPSRVVCMIEWPEHPNRTYEKAYHICVTVLIYFLPLLVIGYAYTVVGITLWASEIP GDSSDR                    235
RNMKR   FLLAFPQCLYSKL...KVMPGRTLCYVQWPEGKQHF..TYHIVILLVYCFPLLIMGVTYTYIVGTILWGGEIP  GDTCDK                    273
          ──IV──
```

FIG. 3B

```
                                                                                              VI
RCCKBR  PGPVHQNGGCRPVTSVAGEDSDGCCVDLPRSR..LEMTTLTTPTPGPVPG.PRPNQAKLLAKKRVVRMLLVTVLLFFLCWLPVYSVNTWRAFDGPGAQ  369
RCCKAR  ..........................................STRYEDSDGCYLQKSRPPRKLELQQLSSGSGGSRLNRURSSSSAANLLAKKRVVIRMLIVIVLFFLCWMPIFSANAWRAYDTVSAE  360
MGRPR   ............................................................................QIESRKRLAKTVLVFVGLFAFCWLPNHVTYLYRSFHYSEVD  295
RNMBR   ............................................................................QMETRKRLAKIVLVFVGCFVFCWFPNHILYLYRSFNYKEID  297
RSKR    ...................................................................................NLRHLQAKKKFVKAMVLVVLTFAICWLPYHLYFLLGTFQEDIYY  281
RSPR    ...................................................................................YHEQVSAKRKVVKMMIVVCTFAICWLPFHVFFLLPYINPDLYL  279
RNMKR   ...................................................................................YHEQLKAKRKVVKMMIVVVTFAICWLPYHVYFILTAIYQQLNR  317
                  VII
RCCKBR  RALSGAPISFI.HLLSYVSACVNPLVYCFMHRRFRQACLDTCARCC.PRPPRARPQP.LPDEDPPTPSIASLSRLSYTTISTLGPG*  452
RCCKAR  KHLSGTPISFI.LLLSYTSSCVNPIIYCFMNKRFRLGFMATFPCCP..NPGPPGVRGE..VGEEEDGRTIRALLSRYSYSHMSTSAPPP*  444
MGRPR   TSMLHFVTSICAHLLAFTNSCVNPFALYLLSKSFRKQ.FNTQLLCC..QPGLMNRSHS..TGRSTTCMTSFKS..TNPSATFSLNRNICHEGYV*  384
RNMBR   PSLGHMIVTLVARVLSFSNSCVNPFALYLLSESFRKH.FNSQLOCG..QKSYPERSTSYLLSSSAVRMTSLKSNAKNVVTNSVLLNGHSTKQELAL*  390
RSKR    HKFIQ.QVYLALFWLAMSSTMYNPIIYCCLNHRFRSGFRLAFRCCPWVTPTEEDRLELTHTPSLSRR......VNRCHTKETLFMTGDMTHSEAT-(21)  390
RSPR    HKFIQ.QVVLASMWLAMSSTMYNPIIYCCLNDRFRLGFKHAFRCCPFISAGDYEGLEMKSTRYLQT.QSSVYKVSRLETTISTVGAHEEEPEEG-(35)  407
RNMKR   WKYIQ.QVVLASFWLAMSSTMYNPIIYCCLNKRFRAGFKRAFRWCPFIOVSSYDELELKTTRFHPTRQSSLYTVSRMESVTVLFDPNDGDPTKSS-(41)  452
```

FIG. 6A

```
CGCAGGATGC GTGCCCAGCT GGACGGAGGG TAGTGAACTC CAGGTGCCTT TAGGAATGGC        60
TGCAAAGCC CACACCTGGC AATCACTCTC TGCCCTGCCTC TCCCCGGCAG GTTGCATTTG       120
GGAGGCGCTC TGGTCATCAG AGGAATGAGC AGGAAATGAGC CTGTTTGCCA GCCCGCCAGC      180
CCCTGGTGGG AAGCAGAGGC GAGG ATG GAC GTG GTA GAC AGC CTT TTT GTG          231
                           Met Asp Val Val Asp Ser Leu Phe Val
                             1               5

AAT GGG AGC AAC ATC ACT TCT GCC TGC GAG CTC GGC TTT GAA AAT GAG         279
Asn Gly Ser Asn Ile Thr Ser Ala Cys Glu Leu Gly Phe Glu Asn Glu
 10                    15                   20                 25

ACA CTT TTC TGC TTG GAT CGG CCC CGG CCT TCC AAA GAG TGG CAG CCG         327
Thr Leu Phe Cys Leu Asp Arg Pro Arg Pro Ser Lys Glu Trp Gln Pro
         30                    35                    40

GCG GTG CAG ATT CTC TTG TAT TCC TTG ATA TTC CTG CTC AGC GTG CTG         375
Ala Val Gln Ile Leu Leu Tyr Ser Leu Ile Phe Leu Leu Ser Val Leu
    45                    50                    55
```

FIG. 6B

```
GGA AAC ACG CTG GTA ATC ACG GTG CTG ATT CGG AAC AAG AGG ATG AGG         423
Gly Asn Thr Leu Val Ile Thr Val Leu Ile Arg Asn Lys Arg Met Arg
                60                65                 70

ACG GTC ACT AAC ATC TTC CTG CTC TCA CTG GCT GTC AGT GAC CTC ATG         471
Thr Val Thr Asn Ile Phe Leu Leu Ser Leu Ala Val Ser Asp Leu Met
          75                 80                 85

CTC TGC CTC TTC TGC ATG CCC TTC AAC CTC ATC CCC AGC CTC AAG             519
Leu Cys Leu Phe Cys Met Pro Phe Asn Leu Ile Pro Ser Leu Lys Lys
        90                 95                100                105

GAT TTC ATC TTC GGG AGT GCC GTG TGC AAG ACC ACC TAC TTC ATG             567
Asp Phe Ile Phe Gly Ser Ala Val Cys Lys Thr Thr Tyr Phe Met
                110                115                120

GGC ACC TCT GTG AGT GTA TCC ACC TTT AAT CTG GTG GCC ATA TCG CTG         615
Gly Thr Ser Val Ser Val Ser Thr Phe Asn Leu Val Ala Ile Ser Leu
        125                130                135

GAG AGA TAC GGA GCA ATT TGC AAA CCC TTA CAG TCC CGC GTC TGG CAA         663
Glu Arg Tyr Gly Ala Ile Cys Lys Pro Leu Gln Ser Arg Val Trp Gln
        140                145                150
```

FIG. 6C

```
ACA AAG TCG CAT GCT TTG AAG GTG ATT GCT GCT ACC TGG TGC CTC TCC    711
Thr Lys Ser His Ala Leu Lys Val Ile Ala Ala Thr Trp Cys Leu Ser
            155                 160                 165
                                          ⎯⎯⎯⎯IV⎯⎯⎯⎯

TTT ACC ATC ATG ACC CCC TAC ATC TAC AGC AAC CTG GTG CCT TTT    759
Phe Thr Ile Met Thr Pro Tyr Ile Tyr Ser Asn Leu Val Pro Phe
170                 175                 180                 185

ACC AAA AAT AAC AAC CAG ACC GGG AAC ATG TGC CGC TTC CTA CTG CCA    807
Thr Lys Asn Asn Asn Gln Thr Gly Asn Met Cys Arg Phe Leu Leu Pro
            190                 195                 200
             ▲

AAC GAT GTT ATG ATG CAG CAG ACC TGG CAC ACT TTC CTG TTA CTC ATC CTC    855
Asn Asp Val Met Met Gln Gln Thr Trp His Thr Phe Leu Leu Ile Leu
            205                 210                 215
                                                    ⎯⎯⎯⎯V⎯⎯⎯⎯

TTT CTT ATT CCC GGA ATT GTG ATG ATG GCA TAT GGA CTG ATT TCT    903
Phe Leu Ile Pro Gly Ile Val Met Met Ala Tyr Gly Leu Ile Ser
170                 225                 230
```

FIG. 6D

| | | | | | | | | | | | | | | | |
|---|---|---|---|---|---|---|---|---|---|---|---|---|---|---|---|
| CTG | GAA | CTT | TAC | CAA | GGA | ATA | AAA | TTC | GAT | GCT | ATC | CAG | AAG | AAA | TCT |
| Leu | Glu | Leu | Tyr | Gln | Gly | Ile | Lys | Phe | Asp | Ala | Ile | Gln | Lys | Lys | Ser |
| 235 | | | | | | 240 | | | | | 245 | | | | |

951

| GCT | AAA | GAA | AGG | AAG | ACA | AGC | ACT | GGC | AGC | AGT | GGC | CCG | ATG | GAG | GAC |
|---|---|---|---|---|---|---|---|---|---|---|---|---|---|---|---|
| Ala | Lys | Glu | Arg | Lys | Thr | Ser | Thr | Gly | Ser | Ser | Gly | Pro | Met | Glu | Asp |
| 250 | | | | | 255 | | | | | 260 | | | | | 265 |

999

| AGT | GAT | GGG | TGT | TAC | CTG | CAG | AAG | TCC | AGG | CAC | CCC | AGA | AAG | CTG | GAG |
|---|---|---|---|---|---|---|---|---|---|---|---|---|---|---|---|
| Ser | Asp | Gly | Cys | Tyr | Leu | Gln | Lys | Ser | Arg | His | Pro | Arg | Lys | Leu | Glu |
| | | | | 270 | | | | | 275 | | | | | 280 | |

1047

| CTT | CGG | CAG | CTG | TCC | CCC | AGC | AGT | GGC | AGC | AGT | GGC | AGC | AAC | AGG | ATC | AAT | CGT |
|---|---|---|---|---|---|---|---|---|---|---|---|---|---|---|---|---|---|
| Leu | Arg | Gln | Leu | Ser | Pro | Ser | Ser | Gly | Ser | Ser | Gly | Ser | Asn | Arg | Ile | Asn | Arg |
| 285 | | | | | | | 290 | | | | | | | | 295 | | |

```
ATC CGG AGC AGC AGC TCC ACC GCC AAC TTG ATG GCC AAA AAG CGG GTG    1143
Ile Arg Ser Ser Ser Ser Thr Ala Asn Leu Met Ala Lys Lys Arg Val
         300                     305                     310
         ─────────────────────────VI─────────────
ATC CGC ATG CTC ATC GTC ATT GTG GTC CTC TTC TTC CTG TGC TGG ATG    1191
Ile Arg Met Leu Ile Val Ile Val Val Leu Phe Phe Leu Cys Trp Met
315                     320                     325
────────────────────────────

CCC ATC TTC AGC GCC AAT GCC TGG CGG GCA TAC GAC ACC GTC TCT GCC    1239
Pro Ile Phe Ser Ala Asn Ala Trp Arg Ala Tyr Asp Thr Val Ser Ala
330                     335                     340             345
                                                ─────VII───────
GAG CGC CAC CTC TCT GGG ACA CCT ATC TCC TTC ATC CTC CTG CTC TCT    1287
Glu Arg His Leu Ser Gly Thr Pro Ile Ser Phe Ile Leu Leu Leu Ser
         350                     355                     360
─────────────────────────────────────────────────

TAC ACC TCC TGC GTC AAC CCC ATC ATC TAC TGC TTC ATG AAC AAA        1335
Tyr Thr Ser Cys Val Asn Pro Ile Ile Tyr Cys Phe Met Asn Lys
365                     370                     375
─────────────────
```

FIG. 6F

```
CGA TTC CGT CTT GGC TTC ATG GCC ACC TTC CCC TGC TGT CCC AAC CCA         1383
Arg Phe Arg Leu Gly Phe Met Ala Thr Phe Pro Cys Cys Pro Asn Pro
380                         385                         390

GGT ACC CCT GGG GTG AGA GGA GAG ATG GGA GAG GAG GAA GGC AGG             1431
Gly Thr Pro Gly Val Arg Gly Glu Met Gly Glu Glu Glu Gly Arg
395                         400                         405

ACC ACA GGG GCG TCT TTG TCC AGA TAC TCC TAC AGC CAC ATG AGC ACC         1479
Thr Thr Gly Ala Ser Leu Ser Arg Tyr Ser Tyr Ser His Met Ser Thr
410                         415                         420                 425

TCT GCT CCG CCC CCG TGAGCTGGGC CCGGGGCTAC ACAGTACAGC AGGAAGGAGG         1534
Ser Ala Pro Pro Pro End
                    430

CCACGGGAGG AGGAGGAGAA AAGAAAGGAA AGGAGAAAGC AGGAGAAGCA GGAGGAGGCA       1594

GAAGCAAAAG AGAAGGAAGG CCCAGGT                                           1621
```

FIG. 7

```
GPCCK_AR   1 MSVERAVCQPASPWWEAEARMDVVDSLFVNGSNITSACELGFENETLFCL  50
             ||..  :  ...||||||||::|||||.:||||:||||||||
RTCCK_AR   1 .....MSHSPARQHLVESSRMDVVDSLLMNGSNITPPCELGLENETLFCL  45

51 DRPRPSKEWQPAVQILLYSLIFLLSVLGNTLVITVLIRNKRMRTVTNIFL 100
             |.|.||||||.|:||||||:||||||||||||||||||||||||||||
          46 DQPQPSKEWQSALQILLYSIIFLLSVLGNTLVITVLIRNKRMRTVTNIFL  95

101 LSLAVSDLMLCLFCMPFNLIPSLLKDFIFGSAVCKTTTYFMGTSVSVSTF 150
             ||||||||||||||||||||||.|||||||||||||||||||||||||
          96 LSLAVSDLMLCLFCMPFNLIPNLLKDFIFGSAVCKTTTYFMGTSVSVSTF 145

151 NLVAISLERYGAICKPLQSRVWQTKSHALKVIAATWCLSFTIMTPYPIYS 200
             |||||||||||||:|||||||||||||||||||||||||||||||||||
         146 NLVAISLERYGAICRPLQSRVWQTKSHALKVIAATWCLSFTIMTPYPIYS 195

201 NLVPFTKNNNQTGNMCRFLLPNDVMQQTWHTFLLLILFLIPGIVMMVAYG 250
             ||||||||||:||||||.|.|||.|:||||||||:||||:||||
         196 NLVPFTKNNNQTANMCRFLLPSDAMQQSWQTFLLLILFLLPGIVMVVAYG 245

251 LISLELYQGIKFDAIQKKSAKERKTSTGSSGPMEDSDGCYLQKSRHPRKL 300
             ||||||||||||| ||||||:|.|||||..  ||||||||||.||||
         246 LISLELYQGIKFDASQKKSAKEKKPSTGSSTRYEDSDGCYLQKSRPPRKL 295

301 ELRQLSPSSSGSNRINRIRSSSSTANLMAKKRVIRMLIVIVVLFFLCWMP 350
             ||.|||.:|:||  |:|||||||.|||:|||||||||||||||||||||
         296 ELQQLSSGSGGS.RLNRIRSSSSAANLIAKKRVIRMLIVIVVLFFLCWMP 344

351 IFSANAWRAYDTVSAERHLSGTPISFILLLSYTSSCVNPIIYCFMNKRFR 400
             ||||||||||||||||:||||||||||||||||||||||||||||||||
         345 IFSANAWRAYDTVSAEKHLSGTPISFILLLSYTSSCVNPIIYCFMNKRFR 394

401 LGFMATFPCCPNPGTPGVRGEMGEEEEGRTTGASLSRYSYSHMSTSAPPP 450
             |||||||||||||.||||||:||||:|||. | |||||||||||||||
         395 LGFMATFPCCPNPGPPGVRGEVGEEEDGRTIRALLSRYSYSHMSTSAPPP 444
```

FIG. 9A

```
CTCGGAGGGG CC ATG GAG CTG CTC AAG CTG AAC CGG AGC CTC CAG GGA        48
           Met Glu Leu Leu Lys Leu Asn Arg Ser Leu Gln Gly
            1                   5        ▲           10

CCC GGG CCT GGG CCG GGG GCT CCC CTG TGC CGC CCG GCT GGC CCG CTT       96
Pro Gly Pro Gly Pro Gly Ala Pro Leu Cys Arg Pro Ala Gly Pro Leu
            15                  20                  25

CTC AAC AGC AGC GGT GCA GGC AAC GTC AGC TGC GAA ACC CCT CGC ATC      144
Leu Asn Ser Ser Gly Ala Gly Asn Val Ser Cys Glu Thr Pro Arg Ile
            30      ▲           35  ▲               40

CGA GAA ACG AGA GAA TTG GAG CTG GCC ATC AGA GTC ACC CTT             192
Arg Glu Thr Arg Glu Leu Glu Leu Ala Ile Arg Val Thr Leu
            50                  55                  60

TAC GCA GTG ATC TTT CTG ATG AGC GTT GGA GGA AAT GTG CTC ATC ATT      240
Tyr Ala Val Ile Phe Leu Met Ser Val Gly Gly Asn Val Leu Ile Ile
            65                  70                  75
```

FIG. 9B

```
GTG GTC CTG GGA CTG AGC CGC CGC CTG AGA ACT GTG ACC AAT GCT TTC    288
Val Val Leu Gly Leu Ser Arg Arg Leu Arg Thr Val Thr Asn Ala Phe
 80                          85                          90

CTG CTC TCC CTG GCA GTC AGT GAC CTC CTG CTG GCT GTG GCT TGC ATG    336
Leu Leu Ser Leu Ala Val Ser Asp Leu Leu Leu Ala Val Ala Cys Met
 95                         100                         105

CCC TTC ACA CTC CTG CCC AAT CTT ATG GGC ACA TTC ATC TTT GGC ACC    384
Pro Phe Thr Leu Leu Pro Asn Leu Met Gly Thr Phe Ile Phe Gly Thr
110                         115                         120

GTC ATC TGC AAG GCT GTT TCC TAC CTC ATG GGG GTG TCT GTG AGC GTG    432
Val Ile Cys Lys Ala Val Ser Tyr Leu Met Gly Val Ser Val Ser Val
125                         130                         135                 140

TCC ACG CTC AGC CTT GTG GCC ATC GCC CTG GAG CGG TAC AGC GCC ATC    480
Ser Thr Leu Ser Leu Val Ala Ile Ala Leu Glu Arg Tyr Ser Ala Ile
           145                         150                         155

TGC CGA CCA CTG CAG GCT CGA GTG TGG CAG ACC CGC TCC CAC GCA GCT    528
Cys Arg Pro Leu Gln Ala Arg Val Trp Gln Thr Arg Ser His Ala Ala
           160                         165                         170
```

FIG. 9C

```
                                                        IV
      CGC GTG ATT TTA GCC ACT TGG CTG TCC GGA TTG CTC ATG GTC CCC    576
      Arg Val Ile Leu Ala Thr Trp Leu Ser Gly Leu Leu Met Val Pro
      175                             180                    185

TAC CCT GTG TAC ACT GCT GTG CAG CCG GTA GGG CCT CGT GTG CTG CAG    624
      Tyr Pro Val Tyr Thr Ala Val Gln Pro Val Gly Pro Arg Val Leu Gln
      190                         195                     200

TGC GTG CAT CGC TGG CCC AAC GCA CGG GTC CGC CAG ACC TGG TCA GTA    672
      Cys Val His Arg Trp Pro Asn Ala Arg Val Arg Gln Thr Trp Ser Val
      205                         210                     215                 220
                                                            V
      CTG CTG CTC CTC TTG TTC TTC CCC GTC GGA GTG GTT ATG GCA GTG    720
      Leu Leu Leu Leu Phe Phe Pro Val Gly Val Val Met Ala Val
                  225                     230                     235

GCC TAC GGG CTC ATC TCC CGC GAG CTC TAC TTA GGG CTT CGC TTT GAC    768
      Ala Tyr Gly Leu Ile Ser Arg Glu Leu Tyr Leu Gly Leu Arg Phe Asp
                  240                     245                     250
```

FIG. 9D

```
GGT GAC GCC GAC AGT GAG AGC CAG AGC AGG GTC CGA GGA CCG GGA GGT      816
Gly Asp Ala Asp Ser Glu Ser Gln Ser Arg Val Arg Gly Pro Gly Gly
        255                 260                 265

CTG TCC GGT TCC GCG CCA GGT TCC GCT CAC CAG AAT GGG CGT TGC CGG      864
Leu Ser Gly Ser Ala Pro Gly Pro Ala His Gln Asn Gly Arg Cys Arg
        270                 275                 280

CCT GAA TCT GGC CTG TCA GGC GAG GAC AGC GAC GGC TGC TAT GTG CAA      912
Pro Glu Ser Gly Leu Ser Gly Glu Asp Ser Asp Gly Cys Tyr Val Gln
285                 290                 295                 300

CTG CCA CGG TCT CGG CCG GCC CTG GAG CTG TCG GCC CTG GCG TCC          960
Leu Pro Arg Ser Arg Pro Ala Leu Glu Leu Ser Ala Leu Ala Ser
        305                 310                 315

ACC CCT GCA GGA CCA GGA CCT GGC CCC ACC CAG GCC AAG CTG CTG         1008
Thr Pro Ala Gly Pro Gly Pro Gly Pro Thr Gln Ala Lys Leu Leu
        320                 325                 330
                                    ─────────── VI ───
GCT AAG AAG CGC GTG GTG CGG ATG TTG CTG GTC ATC GTT GTG CTC TTT     1056
Ala Lys Lys Arg Val Val Arg Met Leu Leu Val Ile Val Val Leu Phe
        335                 340                 345
```

FIG. 9E

```
TTC CTG TGT TGG TTG CCG GTG TAC AGC GCC AAC ACG TGG CGT GCC TTC     1104
Phe Leu Cys Trp Leu Pro Val Tyr Ser Ala Asn Thr Trp Arg Ala Phe
350                 355                 360

GAC GGC CCG GGT GCG CAT CGG GCC CTC TCG GGA GCT CCC ATC TCT TTC     1152
Asp Gly Pro Gly Ala His Arg Ala Leu Ser Gly Ala Pro Ile Ser Phe
365                 370                 375                 380
                                           ├── III

ATC CAT TTG CTG AGC TAC GCC TCC TGT GTC AAC CCA CTG GTC TAC         1200
Ile His Leu Leu Ser Tyr Ala Ser Cys Val Asn Pro Leu Val Tyr
            385                 390                 395

TGC TTC ATG CAC CGT TTT CGC CAG GCC TGC CTG GAC ACT TGC GCC         1248
Cys Phe Met His Arg Phe Arg Gln Ala Cys Leu Asp Thr Cys Ala
400                 405                 410

CGC TGC TGC CCT CGA GCT CGT CCC AGG CCT CTC CCA GAG                 1296
Arg Cys Cys Pro Arg Ala Arg Pro Arg Pro Leu Pro Glu
    415                 420                 425

GAG GAC CCT CCC ACC CCC TCC ATT CGT TCG CTG TCC AGG CTG AGC TAC     1344
Glu Asp Pro Pro Thr Pro Ser Ile Arg Ser Leu Ser Arg Leu Ser Tyr
430                 435                 440

ACC ATC AGC ACG CTG GGG CCC GGC TGATGGGGGT GGTGGGGGCG               1391
Thr Ile Ser Thr Leu Gly Pro Gly End
445                 450
```

FIG. 9F

```
CTGAGGCAGC ACAGGCATCC TGTAAGCACA AATACATCCA GACACACAAG AAACACAAAC  1451
CACACTTGAC AGAGAGACTA ACACTCAACA GCATCGACTA ACCCAACACT CAGGAAACGG  1511
TGGCATAGTA CACACACACA CACACACACC AGAGCTTTAC ACAGAAAGGA GGCTCCCTGA  1571
GGGCCTTCCT AGAGACAGGG CACTGATCTT GACAGGCAAA CATAGCATCC TTAGCAGCAT  1631
CCTTATGCAC TGGGAACTCT GACAGCTGAC CGGTCCTCAT GCCCACATGC ATTAATCACA  1691
CTGATTCTCT AAGGGCAGCA GACCGTGGCA CAGGACTGAT TGGGTTATT CCAGGCTGTC  1751
TTTAGTTTGA CATCACAAGA CACTTCTCCC CACCAGCACT GCCCCTACAA CAGGCCTGAT  1811
ACCTTCCTGA CCAACAGGCT CTTTAGGACT AAAAACTCTC TCTTGTCCC TTTCCAGTTA  1871
AGGACTGCAG CCCTGCCCCC TCATCTTCAC CAGACCTCTT CAAAACACAA TAAATGACTT  1931
GCTCTCAAAA AAAAAAAAAA AAAAAAAAGC GGNNGCAGAA TTCGAGCTCG GTACCCGGGG  1991
ATCCTCTAGA GTCGACCTGC AGGC                                         2015
```

FIG. 10

FIG. 12A human CCKB receptor

```
ATG GAG CTG CTC AAG CTG AAC CGG AAC GTG CAG GGA ACC GGA CCC GGG      48
Met Glu Leu Leu Lys Leu Asn Arg Asn Val Gln Gly Thr Gly Pro Gly
 1               5                  10                  15

CCG GGG GCT TCC CTG TGC CGC CCG GGG GCG CCT CTC AAC AGC AGC          96
Pro Gly Ala Ser Leu Cys Arg Pro Gly Ala Pro Leu Asn Ser Ser
                 20                  25                  30

AGT GTG GGC AAC CTC AGC TGC GAG CCC CCT CGC ATT CGC GGA GCC GGG    144
Ser Val Gly Asn Leu Ser Cys Glu Pro Pro Arg Ile Arg Gly Ala Gly
                 35                  40                  45

ACA CGA GAA TTG GAG CTG GCC ATT AGA ATC ACT CTT TAC GCA GTG ATC    192
Thr Arg Glu Leu Glu Leu Ala Ile Arg Ile Thr Leu Tyr Ala Val Ile
             50                  55                  60

TTC CTG ATG AGC GTT GGA GGA AAT ATG CTC ATC ATC GTG GTC CTG GGA    240
Phe Leu Met Ser Val Gly Gly Asn Met Leu Ile Ile Val Val Leu Gly
 65                  70                  75                  80

CTG AGC CGC CGC CTG AGG ACT GTC ACC AAT GCC TTC CTC CTC TCA CTG    288
Leu Ser Arg Arg Leu Arg Thr Val Thr Asn Ala Phe Leu Leu Ser Leu
                 85                  90                  95
```

FIG. 12B

| | | | | | | | | |
|---|---|---|---|---|---|---|---|---|
| GCA | GTC | AGC | GAC | CTC | CTG | GCT | GTG | GCT | TGC | ATG | CCC | TTC | ACC | CTC | 336 |
| Ala | Val | Ser | Asp | Leu | Leu | Ala | Val | Ala | Cys | Met | Pro | Phe | Thr | Leu |
| 100 | | | | | | | 105 | | | | | | 110 | |

| CTG | CCC | AAT | CTC | ATG | GGC | ACA | TTC | ATC | TTT | GGC | ACC | GTC | ATC | TGC | AAG | 384 |
| Leu | Pro | Asn | Leu | Met | Gly | Thr | Phe | Ile | Phe | Gly | Thr | Val | Ile | Cys | Lys |
| 115 | | | | | 120 | | | | | 125 | | | | |

| GCG | GTT | TCC | TAC | CTC | ATG | GGG | GTG | TCT | GTG | AGT | GTG | TCC | ACG | CTA | AGC | 432 |
| Ala | Val | Ser | Tyr | Leu | Met | Gly | Val | Ser | Val | Ser | Val | Ser | Thr | Leu | Ser |
| 130 | | | | 135 | | | | | 140 | | | | | |

| CTC | GTG | GCC | ATC | GCA | CTG | CTG | GAG | CGG | TAC | AGC | GCC | ATC | TGC | CGA | CCA | CTG | 480 |
| Leu | Val | Ala | Ile | Ala | Leu | Leu | Glu | Arg | Tyr | Ser | Ala | Ile | Cys | Arg | Pro | Leu |
| 145 | | | | | 150 | | | | | 155 | | | | | 160 |

| CAG | GCA | CGA | GTG | TGG | CAG | ACG | CGC | TCC | CAC | CGC | GCT | GCG | CGC | ATT | GTA | 528 |
| Gln | Ala | Arg | Val | Trp | Gln | Thr | Arg | Ser | His | Arg | Ala | Ala | Arg | Ile | Val |
| | 165 | | | | | 170 | | | | | 175 | |

| GCC | ACG | TGG | CTG | CTG | TCC | GGA | CTA | CTC | ATG | GTG | CCC | TAC | CCC | GTG | TAC | 576 |
| Ala | Thr | Trp | Leu | Leu | Ser | Gly | Leu | Leu | Met | Val | Pro | Tyr | Pro | Val | Tyr |
| 180 | | | | | 185 | | | | | 190 | | | | |

| ACT | GTC | GTG | CAA | CCA | GTG | GGG | CCT | CGT | GTG | CTG | CAG | TGC | GTG | CAT | CGC | 624 |
| Thr | Val | Val | Gln | Pro | Val | Gly | Pro | Arg | Val | Leu | Gln | Cys | Val | His | Arg |
| | 195 | | | | | 200 | | | | | 205 | |

| TGG | CCC | AGT | GCG | CGG | GTC | CGC | CAG | ACC | TGG | TCC | GTA | CTG | CTG | CTT | CTG | 672 |
| Trp | Pro | Ser | Ala | Arg | Val | Arg | Gln | Thr | Trp | Ser | Val | Leu | Leu | Leu | Leu |
| 210 | | | | | 215 | | | | | 220 | | | | |

FIG. 12C

```
CTC TTG TTC TTC ATC CCG AGT GTG ATG GCC GTG GCC TAC GGG CTT     720
Leu Phe Phe Ile Pro Ser Val Met Ala Val Ala Tyr Gly Leu         240
225                 230                 235

ATC TCT CGC GAG CTC TAC TTA GGG CTT CGC TTT GAC GGC GAC AGT GAC  768
Ile Ser Arg Glu Leu Tyr Leu Gly Leu Arg Phe Asp Gly Asp Ser Asp
        245                 250                 255

AGC GAC AGC AGG GTC CGA AAC CAA GGC GGG CTG CCA GGG GCT         816
Ser Asp Ser Arg Val Arg Asn Gln Gly Gly Leu Pro Gly Ala
260                 265                 270

GTT CAC CAG AAC GGG CGT TGC CGG CCT GAG ACT GGC GCG GTT GGC GAA  864
Val His Gln Asn Gly Arg Cys Arg Pro Glu Thr Gly Ala Val Gly Glu
        275                 280                 285

GAC AGC GAT GGC TGC TAC GTG CAA CTT CCA CGT TCC CGG CCT GCC CTG  912
Asp Ser Asp Gly Cys Tyr Val Gln Leu Pro Arg Ser Arg Pro Ala Leu
290                 295                 300

GAG CTG ACG GCG CTG ACG GCT CCA GGG CCG GGA TCC GGC TCC CGG CCC  960
Glu Leu Thr Ala Leu Thr Ala Pro Gly Pro Gly Ser Gly Ser Arg Pro
305                 310                 315                 320
```

FIG. 12D

```
ACC CAG GCC AAG CTG GCT AAG AAG CGC GTG GTG CGA ATG TTG CTG      1008
Thr Gln Ala Lys Leu Ala Lys Lys Arg Val Val Arg Met Leu Leu
            325                 330                 335

GTG ATC GTT GTG CTT TTT TTT CTG TGT TGG TTG CCA GTT TAT AGT GCC  1056
Val Ile Val Val Leu Phe Phe Leu Cys Trp Leu Pro Val Tyr Ser Ala
        340                 345                 350

AAC ACG TGG CGC GCC TTT GAT GGC GGT GCA CCG GCA CAC CGA CTC TCG  1104
Asn Thr Trp Arg Ala Phe Asp Gly Gly Ala Pro Ala His Arg Leu Ser
        355                 360                 365

GGT GCT CCT ATC TCC TTC ATT CAC TTG CTG AGC TAC GCC TCG GCC TGT  1152
Gly Ala Pro Ile Ser Phe Ile His Leu Leu Ser Tyr Ala Ser Ala Cys
        370                 375                 380

GTC AAC CCC CTG GTC TAC TGC TTC ATG CAC CGT TTT CGC CAG GCC      1200
Val Asn Pro Leu Val Tyr Cys Phe Met His Arg Phe Arg Gln Ala
        385                 390                 395             400

TGC CTG GAA ACT TGC GCT CGC TGC TGC CCC CGG CCT CCA CGA GCT CGC  1248
Cys Leu Glu Thr Cys Ala Arg Cys Cys Pro Arg Pro Pro Arg Ala Arg
        405                 410                 415
```

FIG. 12E

```
CCC AGG GCT CTT CCC GAT GAG GAC CCT CCC ACT CCC TCC ATT GCT TCG        1296
Pro Arg Ala Leu Pro Asp Glu Asp Pro Pro Thr Pro Ser Ile Ala Ser
            420                     425                     430

CTG TCC AGG CTT AGC TAC ACC ACC ATC AGC ACA CTG GGC CCT GGC TGAGGAGTAG  1351
Leu Ser Arg Leu Ser Tyr Thr Thr Ile Ser Thr Leu Gly Pro Gly End
            435                     440                     445

AGGGGCCGTG GGGGTTGAGG CAGGGCTAAT GACATGCACT GACCCTTCCA GACATAGAAA       1411
ACACAAACCA CAACTGACAC AGGAAACCAA CACCCAAAGC ATGGACTAAC CCCAACGACA       1472
GGAAAAGGTA GCTTACCTGA CACAAGAGGA ATAAGAATGG AGCAGTACAT GGGAAAGGAG       1531
GCATGCCTCT GATATGGGAC TGAGCCTGGC CCATAGAAAC ATGACACTGA CCTTGGAGAG       1591
ACACAGCGTC CCTAGCAGTG AACTATTTCT ACACAGTGGG AACTCTGACA AGGGCTGACC       1651
TGCCTCTCAC ACACATAGAT TAATGGCACT GATTGTTTTA GAGACTATGG AGCCTGGCAC       1711
AGGACTGACT CTGGATGCT CCTAGTTTGA CTCTACAGTG ACCCTTCCCA ATCAGCACTG        1771
AAAATACCAT CAGGCCTAAT CTCATACCTC TGACCAACAG GCTGTTCTGC ACTGAAAAGG       1831
TTCTTCATCC CTTTCCAGTT AAGGACCGTG GCCCTGCCCT CTCCTTCCTT CCCAAACTGT       1891
TCAAGAAATA ATAAATTGTT TGGCTTCCTC CTGAAAAAAA AAAAAAAAA                   1951
AAAAAAAAAA GGAATTCC                                                     1969
```

FIG. 13A

```
1   GGAATGGCTGAAAAAGCCCACACCTGAAATCACTCCCTCCTGTCCTCCACGGCAGGTTGCATCTGCGAGACG  75
76  CTTCGGTCATTAGAGGAATGAGCCGGGAGTGAGCAATTCACCAGCTCTCCAGCACTTGGTGGAAAGCAGGCA  150
151 AGGATGGATGTGGTTGACAGCCTTCTTGTGAATGAAGCAACATCACTCCTCCCTGTGAACTCGGGCTCGAAAAT  225
1       MetAspValAlaAspSerLeuLeuValAsnGlySerAsnIleThrProProCysGluLeuGlyLeuGluAsn  24
226 GAGACGCTTTCGCTTGGATCAGCCCCGTCCTTCCAAAGAGTGGCAGCCAGCGGTGCAGATTCTCTTGTACTCC  300
25      GluThrLeuPheCysLeuValAspGlnProSerLysGluTrpGlnProAlaValGlnIleLeuLeuTyrSer  49
301 TTGATATTCCTGCTCAGGCGTGCTGGGAAACACGTGGTCATCACCGTCGATTCGGAACAAGCGGATGCGGACG  375
50      LeuIlePheLeuLeuSerValLeuGlyAsnThrLeuValIleThrValLeuIleArgAsnLysArgMetArgThr  74
376 GTCACCAACATCTTCCTCCCTCCTGGCTGTCAGCGACCTCATGCTCTTCTTCTGCATGCCGTTCAACCTC  450
75      ValThrAsnIlePheLeuLeuSerLeuAlaValSerAspLeuMetLeuPheCysMetProPheAsnLeu  99
451 ATCCCCAATCTGCTCAAGGATTTCATCTTCGGGAGCGCCGTTTGCAAGACCACCACTTCATGGGCACCTCT  525
100     IleProAsnLeuLeuLysAspPheIlePheGlySerAlaValCysLysThrThrThrTyrPheMetGlyThrSer  124
```

FIG. 13B

```
526  GTGAGTGTATCTACCTTTAATCTGGTAGCCATATCTCTAGAGAGATATGGTGCGATTTGCAAACCCTTACAGTCC  600
125  ValSerValSerThrPheAsnLeuValAlaIleSerLeuGluArgTyrGlyAlaIleCysLysProLeuGlnSer  149

601  CGGGTCTGGCAGACAAAATCCCATGCTTTGAAGGTGATTGCTGCTACCTGGTGCCTTTCCTTTACCATCATGACT  675
150  ArgValTrpGlnThrLysSerHisAlaLeuLysValIleAlaAlaThrTrpCysLeuSerPheThrIleMetThr  174

676  CCGTACCCCATTTATAGCAACTTGGTGCCTTTTACCAAAAATAACAACCAGACCGAATATGTGCCGCTTTCTA  750
175  ProTyrProIleTyrSerAsnLeuValProPheThrLysAsnAsnAsnGlnThrAlaAsnMetCysArgPheLeu  199

751  CTGCCAAATGATGTTATGCAGCAGTCCTGGCACACATTCCTGTTACTCATCCTCTTTCTTATTCCTGGAATTGTG  825
200  LeuProAsnAspValMetGlnSerTrpHisThrPheLeuLeuLeuIleLeuPheLeuIleProGlyIleVal  224

826  ATGATGGTGGCATATATGGATTAATCTCTTTGGAACTCTACCAGGGAATAAAATTTGAGGCTAGCCAGAAGAAGTCT  900
225  MetMetValAlaTyrGlyLeuIleSerLeuGluLeuTyrGlnGlyIleLysPheGluAlaSerGlnLysLysSer  249

901  GCTAAAGAAAAGGAAACCTAGCACCACCAGCGGCAAATATGAGGACAGCGATGGGTGTTACCTGCAAAAGACC  975
250  AlaLysGluArgLysProSerThrThrSerGlyLysTyrGluAspSerAspGlyCysTyrLeuGlnLysThr  274
```

FIG. 13C

```
 976 AGGCCCCCGAGGAAGCTGGAGCTCCGGCAGCTGTCCACCGGCAGCAGCAGGCCAACCGCATCCGGAGTAAC 1050
 275 ArgProProArgLysLeuGluLeuArgGlnLeuSerThrGlySerSerArgAlaAsnArgIleArgSerAsn 299

1051 AGTCCGCAGCCAACCTGATGGCCAAGAAAAAGGGTGATCCGGCATGCTCATCGTCATCGTGGTCCTCTTCCTG 1125
 300 SerSerAlaAsnLeuMetAlaLysLysLysGlyAspProAlaCysLeuIleValValLeuValLeuPheLeu 324

1126 TGCTGGATGCCCATCTTCAGCGCCTACGACGCCTGGCGGCCAACGCCTACGACACCGCCTCCGAGAGCGCCTCTCAGGA 1200
 325 CysTrpMetProIlePheSerAlaAsnAlaTrpArgAlaTyrAspThrAlaSerGluArgArgLeuSerGly 349

1201 ACCCCATTCCTTCATCCTCCTCCTGTCCTACACCCTCCTGGTCAACCCCATCATCTACTGCTTCATGAAC 1275
 350 ThrProIleSerPheIleLeuLeuSerTyrThrSerCysValAsnProIleIleTyrCysPheMetAsn 374

1276 AAACGCTTCCGCCTCGGCTTCATGGCCTTCATGGCCTTCCCCCTGCTGCCCAATCCTGTTCCCCCAGGGGCGAGGGGAGAG 1350
 375 LysArgPheArgLeuGlyPheMetAlaThrPheProCysProAsnProProGlyAlaArgGlyGlu 399

1351 GTGGGGGAGGAGGAAGGCGGGGACCACAGGAGCCTCTGTTCCAGTTCTCGTACAGCCATATGAGTGCCTCG 1425
 400 ValGlyGlyGluGluGluGlyGlyThrThrGlyAlaSerLeuSerArgPheSerTyrSerHisMetSerAlaSer 424
```

FIG. 13D

```
1426 GTGCCACCCCAGTGAGATGTCCCCTGACCCTCCACCGCAGAAGGAAGGCAGGGAGGAGGCAGAGAAGAAAGAACG 1500
 425 ValProGlnEnd                                                              428

1501 GAAGAAGAGATCAGGAAGAGAAGGAGCAGAGCTGATGGAGAAGGAAGGCTCCATCTCCAGTGGGAACTCT 1575
1576 TCAAGGTCTCTTTTCATCTTCATCTGATTCGATTCCAGAGCACTGCTCCAGTGGGGCCATGATTGGTTTCTAGGCAGTT 1650
1651 CAAAGCAGGATATGTTAAGTAACACTCAACCATCAG                                     1686
```

DNA ENCODING A CHOLECYSTOKININ RECEPTOR

The present application is a divisional of U.S. application Ser. No. 08/029,170, filed Mar. 10, 1993, now U.S. Pat. No. 6,169,173, which is a continuation-in-part of U.S. application Ser. No. 07/937,609, filed Sep. 2, 1992, now U.S. Pat. No. 5,319,073, and a continuation-in-part of U.S. application Ser. No. 07/928,033, filed Aug. 11, 1992, now abandoned, and a continuation-in-part of U.S. application Ser. No. 07/861,769, filed Apr. 1, 1992, now abandoned, and a continuation-in-part of U.S. application Ser. No. 07/831,248, filed Feb. 7, 1992, now abandoned.

BACKGROUND OF THE INVENTION

The present invention relates to the purification of cholecystokinin (CCK) receptor protein to sequenceable-grade homogeneity. The present invention further relates to obtaining and expressing DNAs that code for CCK receptor protein.

A family of cholecystokinin peptides was originally isolated from the mammalian gastrointestinal tract and was one of the first gastrointestinal peptides to be discovered in the brain. The predominant molecular form of CCK peptide is cholecystokinin-octapeptide (CCK-8) which exists in a sulfated and non-sulfated form.

The cholecystokinin family of receptors is widely distributed throughout the gastrointestinal and central nervous systems where they regulate pancreatic and gastric secretion, smooth muscle motility, growth, anxiety and satiety, analgesia and neuroleptic activity. The receptor family includes $CCK_A$ and $CCK_B$/gastrin receptors by virtue of their affinity for a structurally and functionally related family of peptides, including CCK and CCK analogues having identical COOH terminal pentapeptide sequence and varying sulfation at the sixth (gastrin) and seventh (CCK) tyrosyl residues. $CCK_B$ receptors more recently have been designated $CCK_B$/gastrin receptors because of the suspected homology, perhaps even identity, between $CCK_B$ and gastrin receptors. Kopin et al., PNAS USA 89: 3605 (1992).

Recently, nonpeptide agonists highly selective for each of the CCK receptor subtypes have been developed and further support the subtype classification. The most potent and selective antagonists are L-364,718 for $CCK_A$ and L-365,260 and PD134408 for $CCK_B$/gastrin receptors. The $CCK_A$ receptor differs from $CCK_B$/gastrin receptor particularly in its selectivity for CCK peptide analogues with a sulfate at the seventh position from the COOH terminus.

The $CCK_A$ receptor mediates physiologic gallbladder contraction, pancreatic growth and enzyme secretion, delayed gastric emptying, relaxation of the sphincter of Oddi and potentiation of insulin secretion. The $CCK_A$ receptor also appears in the anterior pituitary, in the myenteric plexus, and in areas of the CNS (midbrain) where CCK interaction with dopaminergic neurons has been implicated in the pathogenesis of a schizophrenia, Parkinson's disease, drug addiction and feeding disorders. Experimental rat pancreatic carcinogenesis is promoted by CCK through the $CCK_A$ receptor.

$CCK_A$ receptors in pancreatic acinar cells have been most well characterized because of the ability to prepare a homogeneous preparation of a hormonally responsive effector system in dispersed acini. In pancreatic acinar cells, CCK peptide interacts specifically with its cell surface receptor, which is coupled to a guanine nucleotide regulatory protein (G protein) which activates phospholipase C, the breakdown of phosphoinositides, the mobilization of intracellular calcium, and the activation of protein kinase C.

$CCK_A$ receptors have been functionally expressed in the plasma membrane of oocytes after injection of rat brain total RNA, and of mRNA from rat pancreatic acinar carcinoma cell line, AR42J. Affinity labeling studies of $CCK_A$ receptors from rat pancreas and partial purification demonstrate an 85–95 kDa, heavily glycosylated, binding subunit with a deglycosylated core protein of 42 kDa.

The $CCK_B$/gastrin receptor is, found predominantly throughout the CNS, where it is thought to modulate anxiety and neuroleptic activity. Interaction between CCK peptide and $CCK_B$/gastrin receptors on mesocorticolimbic, dopaminergic neurons influences the physiological states of stress and anxiety. The presence of $CCK_B$/gastrin receptors on peripheral monocytes and monocyte-derived splenic cells suggests that CCK plays a role in the long suspected neuroendocrine modulation of the immune system.

$CCK_B$/gastrin receptors, found on gastric parietal and chief cells, and gastrointestinal smooth muscle cells, regulate acid and pepsinogen secretion, and gastrointestinal motility, respectively. They are also present on some human gastric and colon cancer cells where they may regulate growth. CCK peptide, acting at peripheral $CCK_A$ receptors and at central $CCK_A$ and $CCK_B$/gastrin receptors plays a significant role in the nervous system control of appetite.

Attempts have been made to purify CCK receptor protein to homogeneity, but these efforts were unsuccessful. Duong et al., *J. Biol. Chem.* 264: 17990–96 (1989), used digitonin-solubilized rat pancreatic receptor to obtain a receptor preparation estimated to be of 80% purity. The Duong purification scheme included a three-step purification process utilizing cation exchange, Ulex europaeus agglutinin-I-agarose, and Sephacryl S-300. Szecowka et al., *Regulatory Peptides* 24: 215–24 (1989), employed a two-step purification scheme to partially purify digitonin-solubilized rat pancreatic receptor that included lectin and CCK affinity chromatography.

Researchers labored unsuccessfully for years to illuminate the molecular structure of CCK receptor protein, but were limited by the inability to purify receptor protein to a homogeneity sufficient for sequencing purposes. Instead, attempts to obtain a purified preparation yielded a partially purified CCK receptor, along with non-CCK receptor proteins. As a result, the accuracy in studies relating, for example, to binding affinities and electrophysioloy, was compromised by the inability to study a particular subtype without contamination by another type. Further, the inability to purify CCK receptor to sequenceable homogeneity prohibited cloning of receptor-encoding DNAs and the recombinant expression of a particular CCK receptor in a transformed cell line.

SUMMARY OF THE INVENTION

It is therefore an object of the present invention to provide a method for obtaining CCK receptor protein, in a homogeneous form suitable for amino acid sequencing.

It is also an object of the present invention to provide DNA molecules that encode CCK receptor protein, as well as host cells that are transformed with such a DNA and that expresses functional CCK receptor protein.

In accomplishing these and other objects, there has been provided, in accordance with one aspect of the present invention, an isolated DNA molecule encoding a CCK receptor protein. In a preferred embodiment, the DNA molecule comprises a first nucleotide sequence that consists of nucleotides 199 to 1485 of FIGS. 1A–E (SEQ ID NO:13), or a DNA sequence which hybridizes under high stringency conditions to an e oligonucleotid probe consisting of nucleotides 199 to 1485. In another preferred embodiment, a DNA molecule can comprise, in addition to the aforementioned first nucleotide sequence, a second nucleotide sequence consisting of nucleotides 154 to 198 of FIGS. 1A–E (SEQ ID NO:13), which second nucleotide sequence is positioned immediately upstream of nucleotide 199 of the first nucleotide sequence.

In another preferred embodiment, an isolated DNA molecule encoding a CCK receptor protein comprises a nucleotide sequence consisting of nucleotides 136 to 1491 of FIGS. 2A–E (SEQ ID NO:15) or a DNA sequence which hybridizes under high stringency conditions to an oligonucleotide probe consisting of nucleotides 136 to 1491 of FIGS. 2A–E (SEQ ID NO:15).

In another preferred embodiment of the invention, an isolated DNA molecule encoding a human CCK receptor protein comprises a nucleotide sequence consisting of nucleotides 1 to 1341 of FIGS. 12A–E (SEQ ID NO:28) or a DNA sequence which hybridizes under high stringency conditions to an oligonucleotide probe consisting of nucleotides 1 to 1341 of FIGS. 12A–E (SEQ ID NO:28).

In another preferred embodiment of the invention, an isolated DNA molecule encoding a human CCK receptor protein comprises a nucleotide sequence consisting of nucleotides 154 to 1437 of FIGS. 13A–D (SEQ ID NO:30), or a DNA sequence which hybridizes under high stringency conditions to an oligonucleotide probe consisting of nucleotides 154 to 1437 of FIGS. 13A–D (SEQ ID NO:30).

In accordance with another aspect of the present invention, an isolated CCK receptor protein is provided that is sufficiently pure to be sequencable. The isolated CCK receptor protein can have the amino acid sequence shown, for example, in any of FIGS. 1A–E, 2A–F, 12A–E (SEQ ID NOS. 14, 16 and 29, respectively) and 13–AD (SEQ ID NO:31). In another preferred embodiment, an isolated CCK receptor protein having an amino acid sequence corresponding to that of amino acids 16–444 of FIGS. 1A–E is provided.

In accordance with another aspect of the present invention, a cell is provided that is transformed with a DNA molecule encoding a CCK receptor protein, where the cell expresses a heterologous polypeptide that possesses a biological activity characteristic of CCK receptor protein.

In accordance with yet another aspect of the present invention, a method is provided for purifying a cholecystokinin receptor, comprising the steps of (a) solubilizing a biological preparation containing cholecystokinin receptor in 1% digitonin, (b) applying the solubilized receptor preparation to a cationic exchange resin and purifying the eluate of the resin, (c) applying the purified eluate to an agarose-bound lectin, and (d) applying an eluate of step (c) to a cibacron blue sepharose column.

BRIEF DESCRIPTION OF THE DRAWINGS

FIGS. 1A–E. Nucleotide and deduced amino acid sequences (SEQ ID NOS. 13 and 14) of the rat pancreatic $CCK_A$ receptor cDNA clone. The solid lines labelled with Roman numerals delineate the putative seven transmembrane domains predicted by Kyte Doolittle criteria, see J. Mol. Biol. 157: 105–32 (1982), and homology with other G-protein receptor superfamily members. Amino acid sequence enclosed within brackets and labelled with Arabic numerals correspond to the five internal peptide sequences obtained following CNBr cleavage or Lys-C digestion of the purified $CCK_A$ receptor protein. The triangles indicate four potential sites of N-linked glycoslation.

FIGS. 2A–F. Nucleotide and deduced amino acid sequences (SEQ ID NOS. 15 and 16) of the rat brain $CCK_B$ receptor cDNA clone. The solid lines labelled with Roman numerals I–VII delineate the putative transmembrane domains predicted by Kyte-Doolittle criteria and homology with $CCK_A$ type receptor, as well as other G-protein-coupled receptor superfamily members. The solid triangles indicate four potential sites for N-linked glycosylation. The solid bars indicate the three potential sites for serine phosphorylation and the solid circles indicate cysteine residues, which are potential sites for either disulfide bridge formation (residues #127 and #205),or palmitoylation (residue #413).

FIGS. 3A–B. Alignment of the rat $CCK_B$ receptor (RCCKBR, SEQ ID NO:16, rat $CCK_A$ receptor (RCCKAR, SEQ ID NO:14), mouse gastrin-releasing peptide receptor (MGRPR, SEQ ID NO:17), rat substance K receptor (RSKR, SEQ ID NO:19), rat substance P receptor (RSPR, SEQ ID NO:20) and rat neuromedin B receptor (RNMBR, SEQ ID NO:18) protein sequences. The sequence of rat neuromedin K receptor (RNMKR, SEQ ID NO:21) is also shown in this Figure. Using the Pileup program sequence analysis package of the Genetics Computer Group, see Devereux et al., Nucleic Acids Research 12: 387 (1984), the $CCK_B$ receptor deduced amino acid sequence (SEQ ID NO:16) was aligned for maximal homology to the deducted protein sequences of the $CCK_A$ receptor (SEQ ID NO:14) and the five sequences (mouse gastrin-releasing peptide, rat neuromedin B, rat neuromedin K, rat substance K and rat substance P receptors, SEQ ID NOS. 17, 18, 21, 19 and 20, respectively) found to be the most homologous upon searching the Swissprot. release #20 and Pir. release #30 protein data banks. Shown here using single letter abbreviations for amino acids is the result of this alignment with shaded areas denoting conserved amino acids. The number of residues in the variable C terminus not displayed are in parenthesis. Solid lines labelled with Roman numerals indicate the seven putative transmembrane domains.

FIGS. 6A–F. Nucleotide and deduced amino acid sequence (SEQ ID NOS. 22 and 23) of the CCK$_A$ receptor in guinea pig gallbladder and pancreas. The solid lines labelled with Roman numerals delineate the putative seven transmembrane domains predicted by Kyte-Doolittle criteria and homology with the other G-protein coupled receptor superfamily members. The solid triangles indicate the potential sites for N-linked glycosylation. The solid lines indicate potential sites for serine and threonine phosphorylation.

FIG. 7. Alignment of the guinea pig CCK$_A$ receptor (GPCCKAR) and rat CCK$_A$ receptor (RTCCKAR) deduced protein sequences (SEQ ID NOS. 24 and 14, respectively). Using the Gap program sequence analysis package of the Genetics Research Group the guinea pig CCK$_A$ receptor deduced protein sequence was aligned for maximal homology with the rat CCK$_A$ receptor deduced protein sequence. Solid lines denote amino acid identity, and dotted lines denote conservative substitutions. Solid lines labeled with Roman numerals indicate the seven putative transmembrane domains.

FIGS. 9A–F. Nucleotide and deduced amino acid sequence (SEQ ID NOS. 25 and 26) of the CCK$_B$ receptor in guinea pig gallbladder and pancreas. The solid lines labeled with Roman numerals delineate the putative seven transmembrane domains predicted by Kyte-Doolittle criteria and homology with other G-protein coupled receptor superfamily members. The solid triangles indicate the potential sites for N-linked glycoyslation. The solid lines indicate potential sites for serine and threonine phosphorylation.

Figure 10:
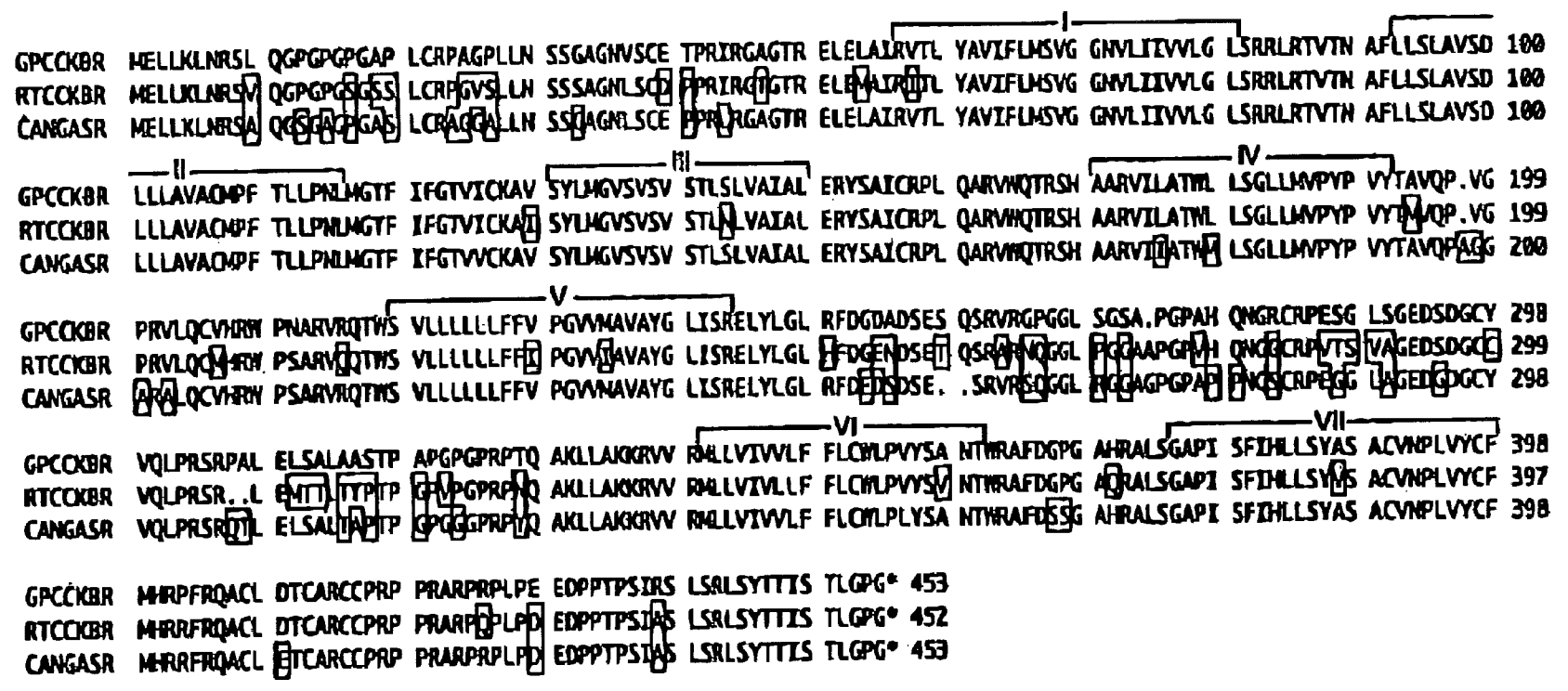

FIG. 10. Alignment of the guinea pig CCK$_B$ receptor (GPCCKBR SEQ ID NO:26) with the rat CCK$_B$ receptor (RTCCKBR SEQ ID NO:16) and the canine gastrin receptor (CANGASR SEQ ID NO:27) deduced protein sequences. Using the Pileup program sequence analysis package of the Genetics Research Group, the guinea pig CCK$_B$ receptor deduced protein sequence was aligned for maximal homology with the rat CCK$_B$ receptor and canine gastrin receptor deduced protein sequences. Solid lines labeled with Roman numerals indicate the seven putative transmembrane domains. Boxed areas denote amino acids not identical between the guinea pig CCK$_B$ receptor and the rat CCK$_B$ and/or gastrin receptors.

FIGS. 12A–E. The nucleotide and deduced amino acid sequences (SEQ ID NOS. 28 and 29) of the human CCK$_B$ receptor cDNA for both brain and stomach.

FIGS. 13A–D. The nucleotide and deduced amino acid sequences (SEQ ID NOS:30 and 31) of the human CCK$_A$ receptor cDNA.

DETAILED DESCRIPTION OF PREFERRED EMBODIMENTS

Figure 4A:
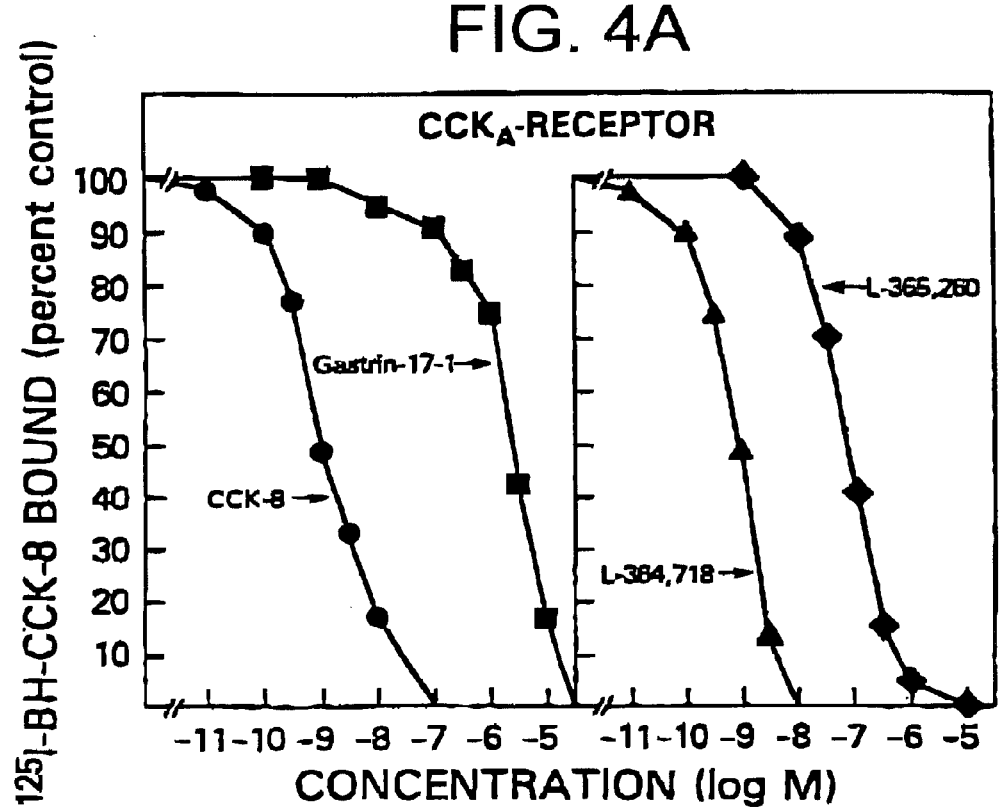
FIGS. 4A and 4B. Ability of CCK receptor agonists and antagonists to inhibit binding of $^{125}$I-BH-CCK-8 to COS-7 cells expressing either $CCK_A$ or $CCK_B$ receptors. COS-7 cells were transfected with the expression vector pCDL-SRα containing either the $CCK_A$ (top panel) or the $CCK_B$ (bottom panel) receptor cDNA sequences. $^{125}$I-BH-CCK8 (50 pM) was incubated either alone or with increasing concentrations of agonists (CCK-8 and gastrin-17-1) (left panel) or antagonists (L-364,718 and L-365,260) (right panel). Data is presented as percent saturable binding (total binding in the presence of radiolabelled hormone alone minus binding in the presence of 1 $\mu$M CCK-8). Each experiment was performed in duplicate and the results given are the means from at least two separate experiments.

An unconventional approach to purifying CCK receptor protein to sequenceable-grade homogeneity has been discovered. By means of this approach, CCK receptor protein now can be obtained and sequenced routinely from a variety of sources. From the sequence information thus obtained it is possible, pursuant to the present invention, to prepare oligonucleotides suitable for cloning CCK receptor genes.

In this context, "CCK receptor" denotes any from a group of proteins that displays a characteristic CCK binding affinity and that is encoded by a nucleotide sequence which hybridizes an oligonucleotide probe designed in accordance with the criteria elaborated herein.

Examples of CCK receptors proteins obtained and sequenced according to the invention include, but are not limited to, CCK$_A$ and CCK$_B$/gastrin receptors. By means of the present invention, it has been discovered that the CCK$_B$ and gastrin receptors are the same protein and possess identical nucleotide sequences in both dog and rat species. Accordingly, the CCK$_B$/gastrin receptor is designated simply as CCK$_B$ receptor, hereinafter.

With regard to probe design, for example, polymerase chain reaction (PCR) primers can be made utilizing polynucleotide regions common to both the CCK$_A$ gene and the CCK$_B$ gene, such as a portion of the coding sequence which encodes one or more of the seven transmembrane domains (see FIGS. 1A–E and 2A–F). PCR primers designed along these lines can be degenerate in order to hybridize to members of the CCK receptor family that are not identical to CCK$_A$ or CCK$_B$ receptor.

A DNA molecule that is a coding sequence for a CCK receptor protein is defined according to the present invention. In preferred embodiments, the DNA molecule comprises a nucleotide sequence consisting of nucleotides 199 to 1485 of FIGS. 1A–E (SEQ ID NO:13), or of nucleotides 154 to 1485 of FIGS. 1A–E (SEQ ID NO:13), or of a DNA sequence which hybridizes under high stringency conditions to an oligonucleotide probe consisting of nucleotides 199 to 1485. In another preferred embodiment, the molecule comprises nucleotides 136 to 1491 of FIGS. 2A–E (SEQ ID NO:15) or a DNA sequence which hybridizes under high stringency conditions to an oligonucleotide probe consisting of nucleotides 136 to 1491. In yet another preferred embodiment, the molecule comprises nucleotides 1 to 1341 of FIGS. 12A–E (SEQ ID NO:28) or a DNA sequence which hybridizes under high stringency conditions to an oligonucleotide probe consisting of nucleotides 1 to 1341.

The targeted gene is amplified using standard PCR technology, and the product obtained by amplification then is used to probe, under high stringency conditions, a genomic or cDNA library containing a polynucleotide coding for CCK receptor. High stringency conditions are illustrated by 0.1×SSC (0.015 saline sodium citrate, 0.15 M NaCl) at a temperature of 55° C. PCR RACE and Anchored methodologies as described, for example, by Frohman et al., *Proc. Nat'l Acad. Sci USA* 85: 8998–9002 (1988), are suitable for use in this context.

Alternatively, an oligonucleotide probe can be designed for use in screening genomic or cDNA libraries that contain polynucleotides coding for CCK receptor. Thus, one would screen for hybridization using a labeled probe which is a full-length or a partial-length $CCK_A$ or $CCK_B$ receptor coding sequence. An exemplary screening process entails screening first under low stringency conditions, then under high stringency, and selecting those plaques which do not hybridize under the latter conditions. Conditions for low stringency include, for example, 2×SSC at a temperature from 37°–42° C. Once a probe is obtained and a library screened, conventional genetic engineering methodologies may be employed to clone and express the receptor gene in a cell line.

The term "CCK binding affinity" is used in this description, with reference to those molecules that have a high affinity for CCK-8, desulfated CCK-8, CCK-33, CCK-4, desulfated or sulfated gastrin 17-1, gastrin 17-2, pentagastrin or other CCK analogues or CCK family members which are non-sulfated or sulfated. A "high affinity" molecule, in this context is one having a binding affinity constant, $K_A$, for CCK or CCK analogues that is within the range of 10 nanomolar or smaller (picomolar).

Essentially similar approaches can be used, pursuant to the present invention, to identify and clone other CCK receptor genes or $CCK_A$ and $CCK_B$ receptor proteins from different mammalian species, such as human, mouse, rabbit, dog, cat, ferret, goat, pig and monkey. That is, other CCK receptors can be obtained by PCR cloning or library-hybridization screening, or by purification from natural sources. CCK receptor purified to homogeneity from a natural source also can be sequenced. The sequence information in turn is applied to design a probe, as described above, for use in a cloning or hybridization-screening regimen.

Cells which can be transformed with a vector containing receptor DNA of the present invention include eukaryotic cells which can accommodate post-translational processing, such as glycosylation and palmitoylation, and which preferably do not express CCK receptor protein naturally. Illustrative of such eukaryotic cells are Xenopus oocytes, COS-7 and other COS cells, CHO and Swiss 3T3 cells. It is particularly preferred that the host cell possess a "second messenger" pathway, such as a G protein/protein kinase C pathway as found in pancreatic acinar cells, which is relevant to the activity of the CCK receptor in the native cell.

Transformed eukaryotic cell lines are useful for studying the receptor in an environment similar to its native environment, for example, in the context of studying the electrophysiology or binding properties of the receptor. Additionally, a prokaryotic or an insect host cell can be used for expressing CCK receptor, thereby to produce large amounts of receptor for immunological purposes or for studying protein structure, for example, crystallographically.

To confirm that a clone encodes a particular CCK receptor, ligand dose inhibition studies can be performed in cells transfected with the specific receptor cDNA insert. Examples of inhibition studies along these lines are described by Knapp et al., *J. Pharm. Exp. Ther.* 265: 3 (1990), by Grider et al. *Gastrointest. Liver Physiol.* 22: 184–90 (1990), and by Roche et al., *Gastrointest. Liver Physiol.* 23: 182–88 (1991), the respective contents of which are hereby incorporated by reference.

As, mentioned previously, the present invention relates to obtaining CCK receptor protein in a form that is sufficiently homogeneous to permit sequencing of the receptor. CCK receptor protein is obtained from smooth muscle cells of the gastrointestinal tract, such as stomach or gall bladder. Other gastrointestinal cells which express CCK receptor include gastric mucosal isolates, containing a mixture of parietal, chief, ECL and D cells. Cells of the central or peripheral nervous system are another source of CCK receptors. In addition to natural tissue, CCK receptor protein can be obtained from cultured cell lines, such as AR42-J, CHP212 and NCI-H209, or from COS-7 cells transfected with either the $CCK_A$ or the $CCK_B$ receptor encoding-DNA (see Example 3).

CCK receptors isolated from such sources can be purified by a regimen which includes the steps of (a) solubilizing a biological preparation containing cholecystokinin receptor in 1% digitonin, (b) applying said solubilized receptor preparation to a cationic a exchange resin, and purifying the eluate of said resin (c) applying said purified eluate to a agarose-bound lectin column, preferably a wheat-germ agglutinin agarose column, (d) applying eluate of step (c) to a cibacron blue sepharose column, (e) trace-labeling and subjecting purified receptor to SDS-PAGE gel electrophoresis (reducing conditions) to obtain purified receptor electro-eluted from the gel. In connection with this purification process, other affinity columns having similar properties, for example, Ulex europaeus agglutinin-I-agarose, can be used.

The amino acid sequence of an isolated CCK receptor purified by the above method can be determined, hence the term "isolated CCK receptor protein", in this context, refers to a CCK receptor protein of sufficient purity to be sequencable via the modified Edman degradation methodology (mixture sequencing and OPA blocking) as described in Example 1. A nucleotide probe can be synthesized which corresponds to the amino acid sequence of the isolated CCK protein or fragments thereof. This nucleotide probe can be used to isolate other CCK proteins in the manner described above.

Isolated CCK receptor proteins or fragments thereof are useful for obtaining antibodies which can recognize CCK-expressing cells. Although the length of a CCK receptor polypeptide or fragment thereof used to stimulate antibody production is not critical, the requirement for immunogenicity may require that the polypeptide be attached to a immunogenicity-imparting carrier, e.g., a particulate carrier like a liposome or a soluble macromolecule (protein or polysaccharide) with a molecular weight in the range of about 10,000 to 1,000,000, or be administered with an adjuvant, such as complete Freund's adjuvant. For artificial polypeptides, as distinguished from CCK fragments, maximum length is determined largely by the limits of techniques readily available for peptide synthesis, that being about fifty amino acids. Thus, a synthetic polypeptide of the present invention is preferably between four and about fifty amino acids in length.

In this context, the term "antibody" encompasses monoclonal and polyclonal antibodies. Such an antibody can belong to any antibody class (IgG, IgM, IgA, etc.). For monoclonal antibody (Mab) production, one generally proceeds by isolating lymphocytes of an animal which has been sensitized with $CCK_A$ or the $CCK_B$ receptor polypeptide, and fusing them with myelona cells, producing hybridomas. The cloned hybridomas are then screened for production of antibodies that bind preferentially to either the $CCK_A$ or the $CCK_B$ receptor.

"Antibody" also encompasses fragments, like Fab and $F(ab')_2$, of anti-$CCK_A$ or anti-$CCK_B$ antibodies, and conjugates of such fragments, and so-called "antigen binding proteins" (single-chain antibodies) which are based on anti-$CCK_A$ or anti-$CCK_B$ antibodies, in accordance, for example, with U.S. Pat. No. 4,704,692, the contents of which are hereby incorporated by reference. Alternatively, Mabs or a fragment thereof within the present invention can be produced using conventional procedures via the expression of isolated DNA which codes for variable regions of such an Mab in host cells like *E. coli*, see, e.g., Ward, et al., *Nature*, 341:544–546 (1989), or transfected murine myeloma cells. See Gillies, et al., *Biotechnol.* 7: 799–804 (1989); Nakatani, et al., *Biotechnol.* 7: 805–10 (1989).

Diagnostic applications of these antibodies are exemplified, according to the present invention, by the use of a kit containing an anti-$CCK_A$ or an anti-$CCK_B$ antibody, which undergoes a reaction with a biological sample to determine the extent of $CCK_A$ or $CCK_B$ protein expression. Such a reaction involves the binding of anti-$CCK_A$ antibody to $CCK_A$ antigen or the binding of anti-$CCK_B$ antibody to $CCK_B$ antigen. The observation of an antibody-antigen complex in a biological sample would indicate a positive result. A kit of this sort could be used to detect the extent of expression of CCK receptor in a particular biological sample from an individual, animal, or cell line.

Pursuant to another aspect of the present invention, a CCK receptor-antagonist or agonist can be site-directed to CCK-expressing cells. This is accomplished by conjugating such a compound to a monoclonal antibody, such as an anti-$CCK_A$ or anti-$CCK_B$ antibody. In a preferred embodiment, a CCK inhibitory compound, such as the specific $CCK_A$ receptor-antagonist, L-364,718 or the specific $CCK_B$ receptor-antagonist, L-365,260, is conjugated to an antibody. Conjugation is accomplished by conventional methods for antibody-toxin linkage, such as described by Hertler et al., *J. Clin. Oncol.* 7(12): 1932 (1989), which is incorporated by reference herein. The antibody conjugates described according to the invention can be used to target CCK-expressing cells, which are present in colon, gastric, and pancreatic tumors, as well as in small cell lung carcinomas.

The present invention is further described with reference to the following, illustrative examples.

EXAMPLE 1

ISOLATION AND CLONING OF $CCK_A$ RECEPTOR

Purification of $CCK_A$, Receptors From Rat Pancreas

Rat pancreatic membranes were prepared from 250 male Sprague-Dawley rat pancreases and solubilized in 2.5 liters of buffer (10 mM HEPES (pH 6.5), 1 mM EGTA, 5 mM $MgCl_2$, 1 μM dithiothreitol (DTT), 1 μM leupeptin, 1 μM pepstatin, 0.5 mM phenylmethylsulfonyl fluoride (PMSF), 140 μg/ml bacitracin, 200 μg/ml benzamidine and soybean trypsin inhibitor 0.1 mg/ml at 4° C.) with 1% (weight/volume) digitonin using similar methods, as described by Szecowka et al., *Reg. Pep.* 10: 71 (1985), and Chang et al., *Biochem J.* 3: 1709 (1987). Soluble extract was applied to a S-Sepharose (Pharmacia) cationic exchange column (4×15 cm), washed with 600 ml of buffer containing 100 mM NaCl and 0.2% digitonin and eluted with buffer containing 300 mM NaCl and 0.2% digitonin. Receptor purification was followed by a radiolabelled antagonist ([$^3$H]L-364,718) binding assay until final purification by SDS-PAGE. Elution fractions containing [$^3$H]L-364,718 binding activity were pooled, diluted with ⅓ volume of buffer and applied to a wheat-germ agglutinin agarose (Vector Labs) affinity column (1.7 ml packed volume in a Bio-Rad Econo Column), washed overnight with 100 column volumes of buffer containing 150 mM NaCl and 0.1% digitonin and eluted stepwise with 3×1.4 ml volumes of wash buffer plus 16 mM N,N', N"-triacetylchitotriose. The pooled elutions were then applied to a Cibacron Blue Sepharose (Pharmacia) column (0.5 ml packed volume in a Bio-Rad Econo Column), washed and eluted with five 0.5 ml volumes of buffer with 1 mN Cibacron F3GA in a method similar to the above wheat-germ affinity chromatography. Purified receptor was then trace labelled with $^{125}$I by the chloramine T method and subjected to preparative SDS-PAGE (11%) under reducing conditions (50 mM DTT). The major Coomassie brilliant blue stained band corresponding to >90% of the radioactivity was cut, electroeluted, ethanol precipitated and submitted for amino acid analysis and sequencing. Each step of the receptor purification was assayed for protein either by the method of Bradford, *Anal. Biochem.* 72: 248 (1976), and corrected for the presence of digitonin, or on the basis of amino acid compositional analysis (Beckman analyzer).

Automated Protein Sequence Analysis

Ten micrograms of intact purified rat pancreatic $CCK_A$ receptor was subjected to automated sequence analysis on an Applied Biosystems model 475A gas phase sequencer.

Chemical and Eenzymatic Cleavage of the CCK Receptor

Cyanogen bromide (CNBr) cleavage of the CCK receptor was performed on the sequencer filter after five cycles of Edman degradation of the intact receptor using standard methods. The chemically cleaved receptor was then resequenced.

Lysyl Endopeptidase (Wako Chemicals, Osaka, Japan) digestion was performed on 10 μg of the purified $CCK_A$ receptor in 150 μl of 0.1 M Tris HCL, pH 9.0. Enzyme (1:20 relative to the receptor weight) was added at 0 and 2 hours and the reaction was continued for a total of 16 hours at 37° C. and then fractionated by HPLC.

Sequencing of the mixture of peptides was performed on chemical and enzymatic digests to determine the cycle at which proline appeared at the amino terminus. Primary amines of the mixture of peptides were blocked in subsequent sequencing runs where prolines appeared using o-phthalaldehyde (Pierce Chem. Co.) 0.2% (w/v) in n-butyl chloride containing 0.6% (w/v) β-mercaptoethanol delivered through the S1 reservoir instead of R1 (phenylisothiocyanate) at predetermined cycles.

HPLC Separation of CCK Receptor Peptides

CCK receptor products were fractionated on a 2.1 mm×3 cm $C_4$ reverse phase column (Aquapore Bu-300, Brownlee Labs).

Construction of a Rat Pancreatic cDNA Library and Isolation of cDNA Clones

Messenger RNA was isolated from male, Sprague-Dawley rat pancreas. Oligo dt-primed cDNA of greater than 2 Kb in size was size selected by electrophoresis on an agarose gel. A library was constructed in lambda Zap II (Stratagene) and in vitro packaged according to established methods. Approximately $7.5 \times 10^5$ plaques were screened with a $^{32}$P labelled, randomly primed probe using a 527 basepair product of the MOPAC PCR described below. Samples on duplicate filters were hybridized at 42° C. overnight, washed once at room temperature for 5 minutes in 300 nM NaCl, 3 mM NaCitrate (2×SSC), 0.1% sodium dodecyl sulfate (SDS) and twice at 45° C. for 20 minutes in 0.1×SSC, and 0.1% SDS, dried and autoradiographed for one to two days. Positive clones were plaque purified and the phagemid pBluescript containing the insert was in vivo excised using the helper phage R408 according to standard protocol (Stratagene).

DNA Sequencing

Sequencing of both DNA strands was done by the dideoxy chain-termination method of Sanger with Seguenase version 2 (United States Biochemical).

cDNA Cloning Using the Polymerase Chain Reaction (PCR)

Mixed oligonucleotides primed amplification of cDNA (MOPAC) was performed using two groups of degenerate primers based on the amino acid sequence from peptides 1 and 3 (FIG. 1B and 1C SEQ ID NO:13). The sense group of primers, based on peptide 1, was 72 fold degenerate, included two inosines and had the following sequence (SEQ ID NO:1): 5'-ATGCCIAT/(CG)AAC/TCTIATC/(AT)CCA/(GCT)AA-3'. The antisense group of primers, based on peptide 3, was 80 fold degenerate and consisted of two groups of 32 and 48 fold degenerate primers with the following sequences respectively: (SEQ ID NO:2) 5' CCA/GTCA/GCTA/GTCT/CTCA/GTA-3' and (SEQ ID NO:3) 5'-CCA/GTCA/(TG)GAA/GTCT/CTCA/GTA-3'. One hundred picomoles of each group of primers were used in the PCR reaction. Four percent of the cDNA reversed transcribed from 1 μg of rat pancreatic mRNA was used as a template. The conditions for the PCR were as follows: denaturation for 1 minute at 94° C., annealing for 1.5 minutes at 50° C. and extension for 1 minute at 72° C. The reaction was carried out for 36 cycles. Two percent of the PCR product served as a template for asymmetric PCR using either the sense or antisense group of primers under otherwise same reaction conditions for an additional 25 cycles. The product of the asymmetric PCR was sequenced to confirm its specificity and to provide sequence needed to generate nondegenerate primers for subsequent PCR.

The remaining 3' coding and untranslated sequence was obtained using the methods of rapid amplification of cDNA ends (RACE) and anchored PCR. RACE PCR was performed using 25 pmoles of the gene specific primers, (SEQ ID NO:4) 5'-GCCAGCCAGAAGAAATCTGCC-3' for the first round and the nested primer (SEQ ID NO:5) 5'-AGCCGAGCACTGGCAGCAGCA-3' for the second round. The RACE PCR conditions were as follows. First round: denaturation for 7 minutes at 95° C., annealing for 2 minutes at 58° C. and extension for 40 minutes at 72° C. for first cycle; denaturation for 45 seconds at 94° C., annealing for 25 seconds at 58° C., and extension for 3 minutes at 72° C. for 19 cycles and a final similar cycle except extension was for 15 minutes. Second round RACE utilized 2% of the first round product, the nested primer above and the same conditions as the first round except for the omission of the first cycle and a total of 25 cycles. Anchored PCR utilized the unamplified cDNA library constructed in lambda Zap-II described above as template DNA, the gene specific primer containing an Xba 1 site and 9 bp cap on the 5' end, (SEQ ID NO:6) 5'-ACTGACTAGTCTAGATCAGCTG CCAACCTGATAGCC-3' and the anchored primer from the vector also with an Xba 1 site and 9 pb cap, (SEQ ID NO:7) 5' ACTGACTAGTCTAGATAATACGACTCACTATAGG-GCG-3'. PCR conditions were as follows: denaturation for 3 minutes at 94° C., annealing for 25 seconds at 61° C., extension for 2 minutes at 72° C. for the first cycle, followed by 33 similar cycles except for denaturation for 45 seconds and a final similar cycle except for extension for 15 minutes. The PCR product was digested with Xba 1, subcloned into pGEM (Promega) and sequenced using standard methods.

The $CCK_A$ receptor open reading frame with 5' and partial 3' flanking sequence (nucleotides 5 to 1506, FIG. 1) was cloned using PCR. The sense primer (SEQ ID NO:8) 5'-ACTGACTAGTCTAGAAATGCTTGCCCAGATGCT-CTG-3' (excluding a 5' Xba 1 site and 9 bp cap) was obtained from sequence of a plaque purified clone resulting from cDNA library hybridization screening described above. The antisense primer (SEQ ID NO:9) 5'ACTGACTAGT-CTAGACAGTGGACCAGGTGGAGTTCA-3' (excluding the 5' Xba 1 site and 9 bp cap) was obtained from sequence of the product of anchored PCR described above. Single stranded cDNA reversed transcribed from rat pancreatic mRNA served as DNA template. The PCR conditions were the same as those used for anchored PCR described above. The PCR product was digested with Xba 1 and subcloned into the expression vector pcDNA-1 (Invitrogen) and sequenced.

Northern Blot Analysis of mRNAs

PolyA+mRNA was isolated from tissue or cell culture lines, electrophoretically separated on a 1.4% agarose/formaldehyde gel, blotted onto Nytran (Schleicher and Schuell), hybridized with $CCK_A$ receptor cDNA probe labelled with $^{32}$P by random priming, washed and autoradiographed for 4 days.

In Vitro Transcription of the CCK Receptor and Expression in Xenopus Oocytes

DNA was in vitro transcribed using T7 RNA polymerase from a CCK receptor clone template (5 to 1506, FIG. 1, SEQ NO:13) in pcDNA-1 (5 μg linearized with Apa 1) in the presence of the cap analog m$^7$G(5')ppp(5')G as recommended by the manufacturer (Promega). Xenopus oocytes were injected with 50 nl of approximately 25 ng of transcribed RNA. At 1–2 days, oocytes were voltage clamped at −70 mV, ligands were applied rapidly and directly to the constantly perfused bath and the ligand dependent Cl⁻ current measured.

Pharmacological studies clearly demonstrate that the rat pancreas contains CCK receptors which are of the $CCK_A$ subtype. (See, Jensen et al., Trends Pharmacol. Sci. 10: 418 (1989). Biochemical studies provide strong evidence on the basis of affinity crosslinking experiments with radiolabelled ligand that the receptors are highly glycosylated and have a molecular weight of 85–95 kDa. With this knowledge, 250 rat pancreases were used to purify the $CCK_A$ receptor to homogeneity. A crude membrane preparation derived from the whole organ was solubilized in 1% digitonin and sequentially purified over three chromatographic columns, cationic exchange resin, wheat-germ agglutinin agarose and Blue sepharose. starting with 11.7 gms of membrane protein this resulted in an approximately 14,600 fold increase in specific radiolabelled antagonist, [$^3$H]L-364,718, binding activity in 260 μg of purified receptor protein. Radiolabelling of the purified receptor was $^{125}$I by the chloramine T method followed by SDS-PAGE under denaturing conditions resulted in a single, broad band (suggesting heavy glycosylation) with molecular weight of 85–95 kDA. Purification on preparative SDS-PAGE and electroelution yielded 200 μg of homogeneous receptor for amino acid sequencing.

Initial attempts to obtain a sequence from 10 μg of purified intact $CCK_A$ receptor were unsuccessful and indicated that the amino terminus of the receptor was blocked to Edman degradation. Treatment of the intact $CCK_A$ receptor on the filter with CNBr after 5 sequencer cycles resulted in the generation of multiple signals upon resequencing which further suggested that the amino terminus was blocked. One of the signals generated on the first sequencing cycle after CNBr cleavage was a proline. Therefore, a second 10 μg of $CCK_A$ receptor was handled similarly, except that a blocking step using O-phthaldehyde (OPA) was performed at the 1st cycle after CNBr cleavage. A single major signal was generated in the next cycle resulting in the sequence of peptide 1 (FIG. 1B, SEQ ID NO:13). This same technique of mixture sequencing and OPA blocking of praline residues was also applied to a lysyl endoproteinase (Lys-C) digest of the intact $CCK_A$ receptor where a praline was observed at cycle 2 of the mixture sequece. This resulted in the sequence of peptide 3 (FIGS. 1B and 1C, SEQ ID NO:13). Further sequence analysis was performed on peptides obtained from Lys-C digestion of intact $CCK_A$ receptor followed by HPLC separation on a $C_4$ column. This resulted in peptides 2, 4 and 5 (FIGS. 1B–D, SEQ ID NO:13).

Based on the sequences of peptides 1 and 3 (FIG. 1B and 1C, SEQ ID NO:13), two groups of mixed degenerate oligonucleotides were synthesized and MOPAC PCR was used on single stranded cDNA reversed transcribed from rat pancreatic mRNA. This resulted in a 527 bp, product (corresponding to sequence 481–1007, FIGS. 1B–D, SEQ ID NO:13) which, after $^{32}P$ random prime labelling, was used for hybridization screening of an oligo (dT) primed cDNA library constructed from rat pancreas in the vector Lambda Zap II. Twenty-six strongly hybridizing clones were identified on initial screening of approximately $7.5 \times 10^5$ clones. However, after three rounds of plaque purification, only 6 clones remained. The six clones were in vivo excised with R408 helper phage into pBluescript and sequenced. All 6 of these clones contained various mutational deletions of the entire 3' end of the hybridizing sequence. Repeat screening of the library using other bacterial species including phenotypically Rec A and B positive Sure cells (Stratagene) gave similar results. Therefore, only partial sequence corresponding to the 5' untranslated and partial 5' coding region (sequence 1–985, FIGS. 1A–D, SEQ ID NO:13) was obtained.

The remainder of the $CCK_A$ receptor sequence was obtained using PCR cloning methods to circumvent the high rate of mutation during amplification in bacteria. With knowledge of the 5' end of the $CCK_A$ receptor cDNA sequence, gene specific primers were synthesized corresponding to sequences 928–948 and 959–979 (FIG. 1D, SEQ ID NO:13), and used in the first and second rounds, respectively, of the RACE protocol. This resulted in only an additional, 366 bp of sequence (sequence 986–1351, FIGS. 1D and 1E, SEQ ID NO:13) because the PCR preferentially amplified truncated products. The remaining 3' sequence was then obtained by the method of "anchored" PCR using a gene specific primer corresponding to sequence 1102–1122 (FIG. 1D, SEQ ID NO:13) and the Lambda Zap II, vector-specific T7 primer/promoter. An additional 155 bp of sequence completed the 3' coding and part of the 3' untranslated sequence to give a total of 1506 bp. The first in frame ATG consistent with a consensus translation initiation site represents the start codon of a single long open reading frame encoding a unique 444 amino acid protein with predicted molecular weight of 49.6 kDa. The five independent peptide sequences obtained from the CNBr cleavage and Lys-C digestion of the purified $CCK_A$ receptor protein are present within the predicted protein sequence (FIGS. 1A–E, SEQ ID NO:13) and confirm that the combined DNA sequence derived from cDNA cloning by library hybridization of PCR codes for the purified protein having high affinity for the specific antagonist, L-364,718. The sequence allows for four potential N-linked glycosylation sites, three in the amino terminus and one in the extracellular fourth loop (FIGS. 1A–E, SEQ ID NO:13) which is consistent with the heavily glycosylated 85–95 kDa band seen on Coomassie staining and subsequent four step reduction to a final molecular weight of approximately 42 kDa following deglycosylation with Endogylcosidase F (FIGS. 1A–E, SEQ ID NO:13). There are four potential sites for protein kinase C phosphorylation, 3 on serine in the large intracellular fifth loop (residues 260, 264 and 275) and one on threonine in the cytoplasmic tail (residue 424) which is consistent with previous data indicating predominately serine, minor threonine and no tyrosine phosphorylation of the $CCK_A$ receptor in rat pancreas following CCK and phorbol 12-myristate 13-acetate stimulation and inhibition of phosphorylation by staurosporine.

A hydropathy plot of the predicted amino acid sequence, using the criteria of Kyte and Doolittle and homology to other G-protein receptor superfamily members, identifies seven regions of hydrophobic residues corresponding to putative transmembrane domains expected for members of the G protein-coupled superfamily of receptors. This is consistent with evidence that G proteins couple $CCK_A$ receptors to phospholipase C in exocrine pancreas. A comparison of the $CCK_A$ receptor deduced protein sequence with all protein sequences in available databanks found that the five most homologous proteins (rat neuromedin K, bovine substance K, mouse gastrin-releasing peptide, rat substance P and rat beta-1 adrenergic receptors) having 27–30% amino acid identity and 50–54% similarity were all members of the G-protein receptor superfamily.

High stringency northern blot analysis of organ- and tissue-specific polyadenylated RNA using a full coding region probe revealed a 2.7 kb hybridizing transcript in rat pancreas and a rat pancreatic acinar carcinoma cell line, AR42J. No hybridization was observed in rat brain or guinea pig gallbladder, organs known to posses CCK receptors, presumably because of low level expression and/or low amount of expressing cell representation in these organs or different receptor subtypes unable to hybridize under the stringent conditions employed. As expected, no signal was observed in liver, muscle or kidney. The size of the hybridizing transcript in consistent with the cloned cDNA size, and the 3 kb size estimated from sucrose gradient fractionation of AR42J mRNA functionally expressed in Xenopus oocytes.

Figure 5A:
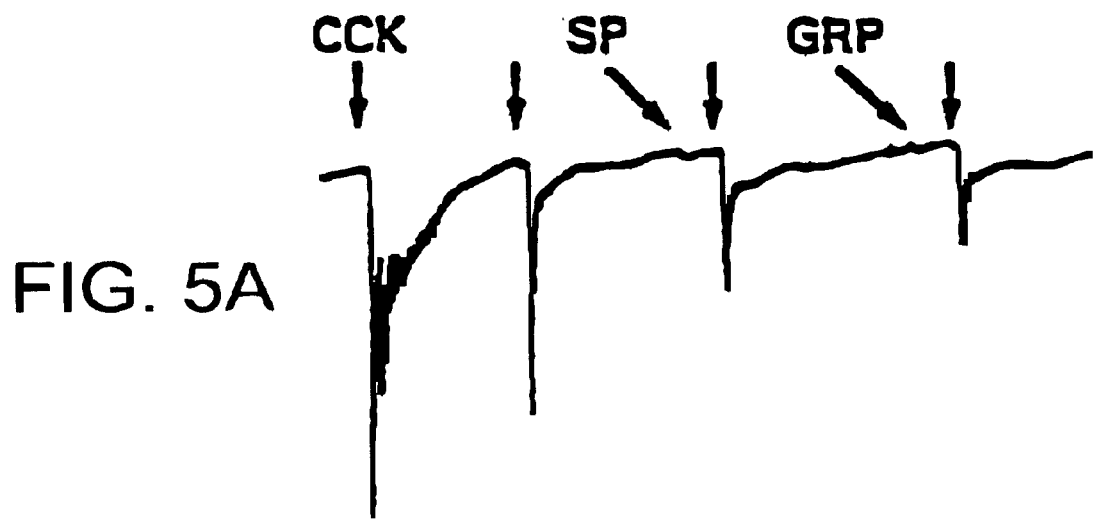
FIGS. 5A and 5B. Expression of the $CCK_A$ receptor in Xenopus oocytes. Ligand, induced chloride currents measured in the same oocytes one (A) and two (B) days after injection of mRNA (25 ng) in vitro transcribed from $CCK_A$ receptor cDNA cloned from rat pancreas. A. Response to agonists. Application of 1 $\mu$M CCK-8 (vertical arrows) elicits a response which desensitizes with repeated applications in the same oocyte. Application of 1 $\mu$M gastrin-releasing peptide and 4 $\mu$M substance P (diagonal arrows), interspersed between response evoking applications of CCK-8, fail to elicit responses. B. Inhibition by the specific CCK$_A$ receptor antagonist, L-364,718. Application of 1 μM CCK-8 (vertical arrows) to the same oocyte shown in (A) two days after mRNA injection elicits a response which is completely inhibited by the coapplication of 5 μM L-364,718 (diagonal arrow). The response to 1 μM CCK-8 could not be restored following antagonist application despite prolonged washes with buffer. Experiments were repeated several times (n=12 for (A) and n=10 for (B)) in different oocytes, with similar results.
Figure 5B:
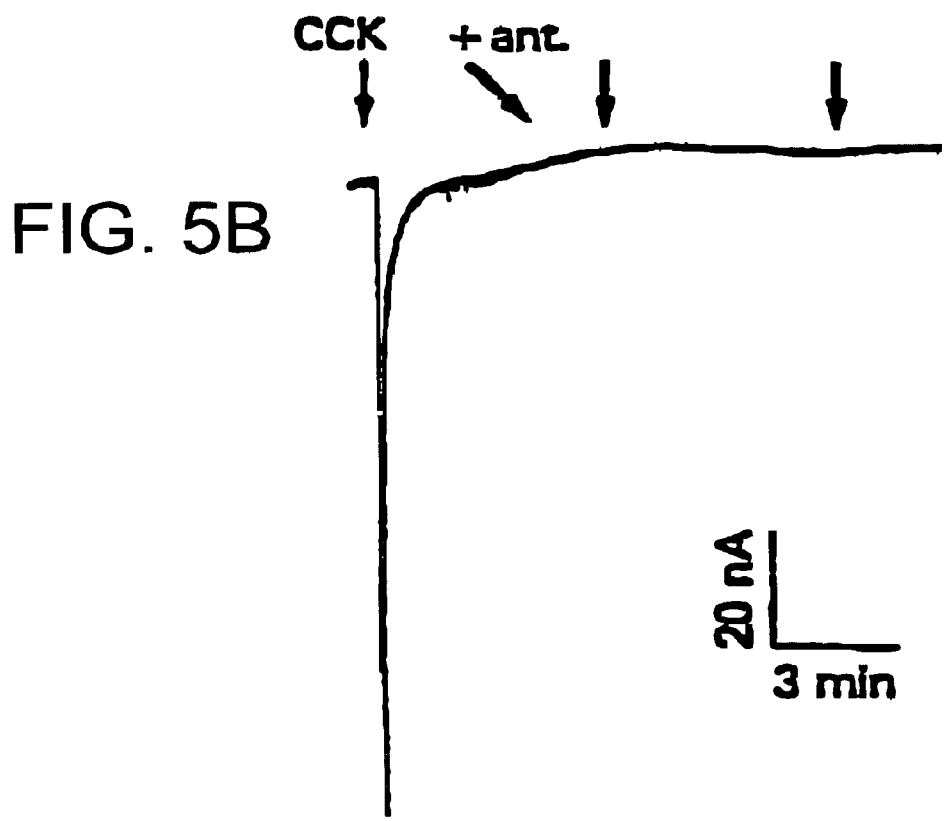
Figure 8:
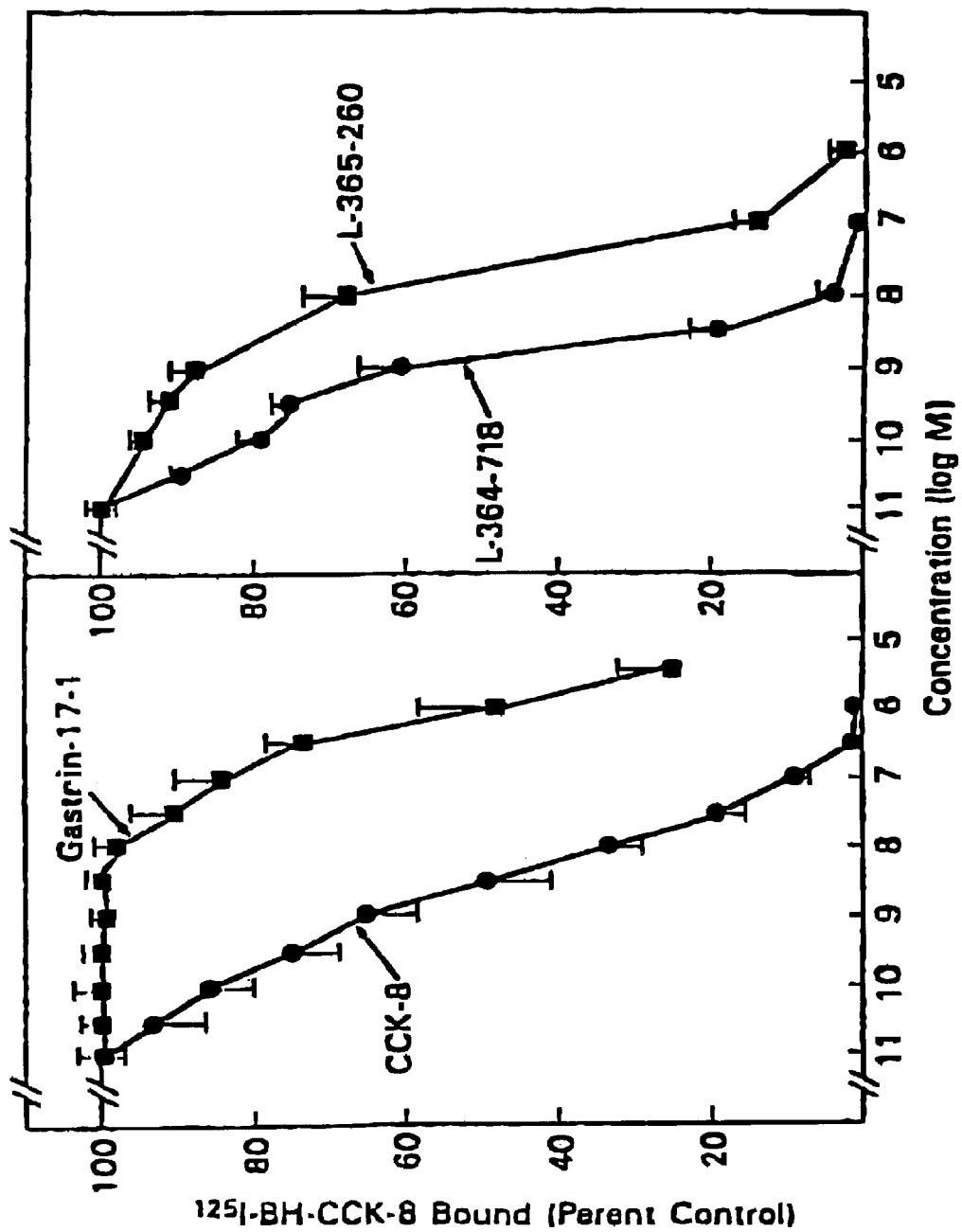
FIG. 8. Ability of CCK receptor agonists and antagonists to inhibit $^{125}$I-BH-CCK-8 to COS-7 cells expressing guinea pig CCK$_A$ receptor. COS-7 cells were transfected with the expression vector pCDL-SRα containing the CCK$_A$ receptor cDNA sequence. $^{125}$I-BH-CCK 8 (50 pM) was incubated either alone or with increasing concentrations of agonists (CCK-8 and Gastrin-17-1) (left panel) or antagonists (L-364,718 and L-365,260) (right panel). Data are presented as percent saturable binding (total binding in the presence of radiolabelled hormone alone minus binding in the presence of 1 μM CCK-8). The results given are means of values from at least three experiments performed in duplicate. Vertical bars are standard deviations from the mean.

To further demonstrate that the protein sequence encoded by the cDNA represents a functional $CCK_A$ receptor, a capped in vitro transcript of a cDNA clone containing the entire coding region and 5' untranslated sequence (5 to 1506 bp FIGS. 1A–E, SEQ ID NO:13) was injected into Xenopus oocytes and assayed for specific, call surface, functional expression 1 and 2 days later (FIGS. 5A and 5B). The oocytes responded to CCK octapeptide (CCK-8) (FIG. 5A) but not to gastrin-releasing peptide (GRP), substance P (SP) nor acetylcholine (ACh). Repeated challenges with CCK-8 caused only a moderate desensitization of the response (FIG. 5A) and allowed an internal positive control for the effect of the specific $CCK_A$ receptor antagonist, L-364,718. Application of the specific, $CCK_A$ receptor antagonist, L-364,718, after an initial response to CCK-8 inhibited any further response to repeated applications of CCK-8 (FIG. 5B). Inhibition was specific for $CCK_A$ receptors (i.e., there was no inhibition of SP or ACh response in oocytes injected with their respective receptor mRNAs). Oocytes injected with rat pancreatic total mRNA'showed a typical CCK-8 evoked response. Coinjection of the same mRNA with an antisense oligo (reverse complement of nucleotides 265 to 295) completely abolished the response to CCK-8.

EXAMPLE 2

CLONING Of $CCK_B$ RECEPTOR cDNA Construction and Isolation of cDNA Clones

Total RNA was isolated from the rat pancreatic carcinoma cultured cell line, AR42-J and rat brain cortex using a low temperature GITC/GnHCl extraction procedure as described by Han et al., *Biochem.* 26: 1617 (1987), and poly (A)+RNA was isolated using oligo dT cellulose. Separate cDNA libraries were constructed from each source of poly (A)+RNA. Oligo dT primed cDNA greater than 2 kilobases was size-selected by agarose gel electrophoresis, electroeluted, adapted with Eco RI, ligated into lambda gt10 arms, and in vitro packaged according to methods described by Davis et al., BASIC METHODS IN MOLECULAR BIOLOGY (1988). Each library ($7.5 \times 10^5$ plaques) was screened with a $^{32}P$ labelled, randomly primed probe corresponding to the coding region of the $CCK_A$ receptor cDNA isolated from rat pancreas initially under conditions of low and later high stringency (three 20-min washes at 42° C. with 2×SSC/0.1% SDS for low stringency screening and three 20-min washes at 55° C. with 0.1×SSC/0.1% SDS for high stringency washes (1×SSC=150 mM NaCl/15 mM sodium citrate, pH 7.0)). Several clones that hybridized at low stringency were plaque-purified from the AR42-J cell library and subcloned into pCDL-SRα at the Xba I site. A $^{32}P$-labelled, randomly primed probe corresponding to the open reading frame of the AR42-J cDNA clones was used to screen another $7.5 \times 10^5$ plaques from the rat brain cortex library under conditions of high stringency. Several purified and subcloned into the vector pCDL-SRα at the Xba I site.

DNA Sequencing

Both strands of two cDNA clones isolated from the AR42-J cell library were sequenced by the dideoxy chain termination method of Sanger using Sequenase 2.0 (U.S. Biochemical). One of the cDNA clones isolated from the rat brain cortex library and the product of PCR cloning from the rat brain subcortex cDNA were cycle sequenced (Bethesda Research Labs).

DNA and Protein Sequence Analysis

Nucleotide and amino acid sequences were analyzed with the Wisconsin Genetics Computer Group software package, by means of the Gap program, as described by Devereux et al., *Nucleic Acids Res.* 12:387 (1984).

Northern Blot Analysis of mRNAs

Poly (A)+RNA was isolated using a low temperature GITC/GnHCl extraction, according to the method of Han et al., *supra*, from rat pancreas, brain cortex and subcortex, striated muscle, liver, kidney, the rat pancreatic acinar carcinoma cell line AR42-J, and guinea pig gallbladder. (Rats do not have gallbladders.) Four micrograms of poly (A)+ RNA per lane were electrophoretically separated on a 1.4% agarose/formaldehyde gel and blotted onto Nytran (Schleicher and Schuell, Keene, New Hampshire). The blot was hybridized separately with $CCK_A$ AND $CCK_B$ full length coding region probes, which had been $^{32}P$-labelled (random-primed). The blot was washed under conditions of high stringency (three 20-minute washes at 55° C. with 0.1×SSC/0.1% SDS) and exposed for 24 hours in a phosphorimager (Molecular Dynamics) to prepare an autoradiograph.

To obtain the rat brain CCK, receptor cDNA, the $^{32}P$ labelled, randomly primed full length coding region of the $CCK_A$ receptor isolated from rat pancreas was used. Approximately $7.5 \times 10^5$ plaques from two rat brain cDNA libraries constructed from cortex and subcortex were screened under conditions of low and high stringency to isolate clones corresponding to pharmacologically described $CCK_B$ receptors, as described by Saito et al., *Science* 1155 (1980). When this approach did not yield any hybridizing plaques, a cDNA library was constructed from AR42-J cells, a rat pancreatic acinar carcinoma cell line known to express predominantly (80%) $CCK_B$ type CCK receptors. Several candidate clones were isolated only under low stringency conditions, two of which contained a long open reading frame highly homologous to the $CCK_A$ receptor cDNA.

To confirm that the $CCK_B$ receptor isolated from the AR42-J cells was the same $CCK_B$ receptor pharmacologically identified in rat brain (Lambert et al., *Reg. Pept.* 322: 151 (1991), $7.5-10^5$ plaques were screened from the cortex cDNA library using the new $CCK_B$ open reading frame sequence as a $^{32}P$ labelled, randomly-primed probe. Only high stringency hybridizing clones were isolated, one of which was a 2,243 bp clone containing identical cDNA sequence to the two clones isolated from the AR42-J cell cDNA library (FIGS. 1A–E, SEQ ID NO:13).

A comparison of the nucleotide sequence of the $CCK_B$ receptor cDNA to the $CCK_A$ receptor cDNA sequence (SEQ ID NOS. 15 and 13, respectively) reveals a 54% homology, higher than any other sequence reported to date. The first in frame ATG consistent with a consensus translation initiation site initiates a single long open reading frame encoding a unique 452 amino acid protein with predicted molecular weight of 48,954 Da. Similar to the $CCK_A$ receptor, the sequence contains four potential N-linked glycosylation sites, three in the amino terminus and one in the fourth extracellular loop, which would account for the larger than predicted molecular weight of 90 kDa reported in affinity crosslinking studies. There is one potential site for protein kinase C phosphorylation on serine in the first intracellular loop (serine residue #82) and two potential sites for protein kinase A phosphorylation on serine-154 in the second intracellular loop and serine-442 in the cytoplasmic tail and none in the third intracellular loop, unlike the $CCK_A$ receptor.

The predicted amino acid sequences of the $CCK_A$ and $CCK_B$ receptors (SEQ ID NOS. 14 and 16, respectively) have a 48% identity which is in the expected range for receptors within the same family and is higher than any other reported protein. A hydropathy plot of the predicted amino acid sequence using criteria of Kyte and Doolittle and homology to the other G-protein receptor superfamily members identifies seven regions of hydrophobic residues corresponding to putative transmembrane domains. Cysteine residues in the first and second extracellular domains are conserved in both receptors as well as other G protein-coupled receptors and may form a disulfide bridge. A cysteine residue in the C-terminal region (residue #377) conserved in most of the G protein coupled receptors may be a membrane anchoring palmitoylation site. An aspartate commonly found in the third transmembrane domain of charged amine ligand binding receptors is absent as expected for these peptide hormone receptors.

Several other areas of $CCK_A$ and $CCK_B$ amino acid sequence homology also are commonly conserved among other G protein-coupled receptors, indicating their common membership in the G protein-coupled receptor superfamily. The five most similar proteins were mouse gastrin-releasing peptide receptor, rat neuromedin B receptor, rat substance K receptor, rat substance P receptor, and rat neuromedin K receptor, which further supports their suspected membership in the G-protein coupled receptor superfamily (FIGS. 3A–B, SEQ ID NOS. 16, 14, 17, 19, 20, 18 and 21). The homology between the two CCK receptor amino acid sequences diverge most notably in the length and composition of their third intracellular loops. This difference may contribute to a difference in G protein coupling specificity since this region has been shown to be important in G protein coupling specificity of other receptors. Cysteines in the first and second extracellular domains are conserved in both receptors and may form a disulfide bridge required for stabilization of a functional tertiary structure as demonstrated for rhodopsin, β-adrenergic and muscarinic receptors. A cysteine in the C-terminal region conserved in many of the G protein coupled receptors may be a membrane anchoring palmitoylation site as demonstrated for rhodopsin and the $\beta_2$-adrenergic receptors. An aspartate commonly found in the third transmembrane domain of charged amine-binding receptors is absent, as expected in these peptide hormone receptors.

Northern blot analysis reveals that the $CCK_A$ receptor cDNA hybridizes to a single poly A+RNA of 2.7 Kb from pancreas and AR42-J cells and 4.4 Kb from guinea pig gallbladder, but not to rat brain, striated muscle, liver, and kidney. The absence of Northern blot hybridization to rat brain is not surprising for such a diverse cellular organ with $CCK_A$ receptors localized to only small discreet areas and is consistent with the need to use PCR cloning methods when a large but limited plaque hybridization screening method failed to identify any positive plaques. High stringency Northern blot hybridization to poly A+RNA from the same tissues using a $CCK_B$ receptor cDNA probe revealed a single hybridizing transcript of 2.4 kB with the expected intensity and distribution in rat brainstem, cortex, and AR42-J cells, and absence of hybridization to rat pancreas, striated muscle, liver, and kidney, tissues and cells expressing either rare or no $CCK_B$ receptors. The size of the hybridizing transcript was in close agreement with the cloned CCK, receptor cDNA isolated from AR42-J cells.

EXAMPLE 3

EXPRESSION OF $CCK_A$ AND $CCK_B$ RECEPTOR cDNAS IN MAMMALIAN CELLS AND LIGAND INHIBITION STUDIES

Two micrograms of PCDL-SRα containing either the $CCK_A$ coding region insert subcloned at an Xba 1 site in the sense orientation or the $CCK_B$ insert subcloned at an Eco R1 site in the sense orientation were transfected into a near confluent 100 mm tissue culture plate containing approximately $1 \times 10^6$ COS-7 cells using a DEAE/dextran method. Approximately 48 hours post transfection, the cells were washed twice with phosphate buffered saline (PBS), pH 7.4, 0.1% BSA at 4° C., scraped from the plate in Dulbeccols Modified Eagle's Medium (DMEM), 0.1% BSA, 4° C., centrifuged at 400×G, and resuspended at approximately 3–105 cells per ml in DMEM, 0.1% BSA, 4° C. Five hundred microliters of resuspended cells were incubated for 60 minutes at 37° C. with 50 pM of the radiolabelled hormone $^{125}$I-Bolton-Hunter-CCK-8 (2200 Ci/mmole) either with or without varying concentrations of unlabelled agonist or antagonist. Cells were subsequently washed three times with 2 ml PBS, 0.1% BSA, 4° C. by filtration on glass filters (Whatman GF/B) using a suction manifold (Millipore). Filters were assayed for gamma radioactivity (Packard, Auto-Gamma).

To confirm that the two receptors cloned from rat brain correspond to the $CCK_A$ and $CCK_B$ receptor subtypes, ligand binding dose inhibition studies were performed. COS-7 cells transfected with the full length cDNA inserts of either $CCK_A$ (FIGS. 2A–F, SEQ ID NO:13) or $CCK_B$, (FIGS. 2A–F, SEQ ID NO:15) subcloned into the vector, PCDL-SRα (at the Xba1 site), were incubated with the radiolabelled ligand, $^{125}$I-BH-CCK-8, alone or in the presence of increasing concentrations of unlabelled CCK receptor agonists or antagonists. Studies with COS-7 cells transfected with the vector containing the $CCK_A$ receptor cDNA insert showed that radiolabelled $^{125}$I-CCK-8 binding inhibition by CCK-8 was about 1000–10,000 fold, or preferably about 3000 fold more potent than gastrin-17-I, and that the $CCK_A$ receptor specific antagonist, L-364,718 was about equally potent to CCK-8, and about 30–100 fold more potent than the $CCK_B$ receptor specific antagonist, L-365,260.

Studies with COS-7 cells transfected with the vector containing the $CCK_B$ receptor cDNA insert showed that CCK-8 was only about 3–10 fold more potent than Gastrin-17-I, and that the $CCK_B$ receptor specific antagonist, L-365, 260 was about 10–100 fold more potent than the $CCK_A$ receptor specific antagonist, L-364,718 at inhibiting $^{125}$I-BH-CCK-8 binding. These results agree closely with previous pharmacological binding studies of $CCK_A$ and $CCK_B$ receptors from rat brain and support the classification of these cloned receptors from rat brain as $CCK_A$ and $CCK_B$ subtypes.

It was demonstrated that DNA molecules encoding CCK receptor proteins can be obtained by employing nucleotide sequences encoding $CCK_A$ and $CCK_B$ receptor proteins as identified by the present invention as probes to isolate from other species such nucleotide molecules encoding CCK receptor protein. Using the methods described above, DNA molecules encoding guinea pig $CCK_A$ and $CCK_B$ receptor proteins were isolated, whose sequences, are provided in FIGS. 6A–F (SEQ ID NOS. 22 and 23) and 9A–F (SEQ ID NOS. 25 and 26), respectively.

EXAMPLE 4

CONSTRUCTION OF A GUINEA PIG GALLBLADDER cDNA LIBRARY AND ISOLATION OF $CCK_A$ AND $CCK_B$ RECEPTOR cDNA CLONES

Male Hartley guinea pigs (150–175 g) were obtained from the Small animal section, Veterinary Resources Branch, National Institutes of Health, Bethesda, Md. Guinea pig pancreases and gallbladders were immediately snap frozen in liquid nitrogen. Total RNA was extracted using a low temperature guanidine isothiocyanate/guanidine hydrochloride method (Han et al., *supra*). Poly (A)+RNA was isolated using oligo dT cellulose. Oligo dT primed cDNA>2 kb was size selected by agarose gel electrophoresis, electroeluted, adapted with Eco R1, ligated into lambda gt 10 arms and in vitro packaged using established methods. Approximately 8–105 plaques were screened under high stringency conditions with a $^{32}$P-labelled, randomly primed probe generated from the rat $CCK_A$ or the rat $CCK_B$ receptor coding regions to obtain the guinea pig $CCK_A$ or $CCK_B$ receptors, respectively. Duplicate filters were washed once at room temperature for 5 minutes in 2×standard saline citrate (SSC; 2×SSC =300 mN NaCl/3mM sodium citrate and 0.1% SDS) and three times at 55° C. for 20 minutes in 0.1×SSC and 0.1% SDS, dried and autoradiographed for 2 days using. Positive hybridizing clones were plaque purified using established methods.

EXAMPLE 5

ISOLATION OF HUMAN CCK$_B$ RECEPTOR cDNA

The nucleotide and deduced amino acid sequences of the human CCK$_B$ receptor cDNA (FIGS. 12A–E, SEQ ID NOS 28 and 29), found to be identical for both brain and stomach, were obtained according to the following method. A human temporal cortex oligo d(T)/random-primed cDNA library, in λ-phage vector, DR 2 (Clontech, Palo Alto, Calif.; catalogue #HL1143), was screened under low stringency conditions (three 30-minute washes in 2×SSC (0.015 saline sodium citrate, 0.15 M NaCl), 0.1% SDS (sodium dodecyl sulfate) at 37° C.) with a $^{32}$P-labelled, random-primed probe derived from the rat CCK$_B$ receptor cDNA. The longest clone, Hu-B-10, provided the sequence of nucleotides 281–1969.

The initial portion of the sequence, nucleotides 1–280, was obtained by the polymerase chain reaction using the degenerate sense primer, (SEQ ID NO:10) 5'-GGAG/CC/TTCA/GG/CA/TGGA/GGCCATGGA-3'. This degenerate primer was derived from the rat and guinea pig CCK$_B$ receptor cDNA sequences. The antisense primer used, (SEQ ID NO:11) 5'-GGGCCAGCGATGCACGCACTG-3, was obtained from the Hu-B-10 cDNA sequence described above. The target DNA for PCR was human stomach cDNA prepared from oligo d(T)-primed mRNA, according to the method described by Wank et al., PNAS USA 89: 3125 (1992).

Figure 4B:
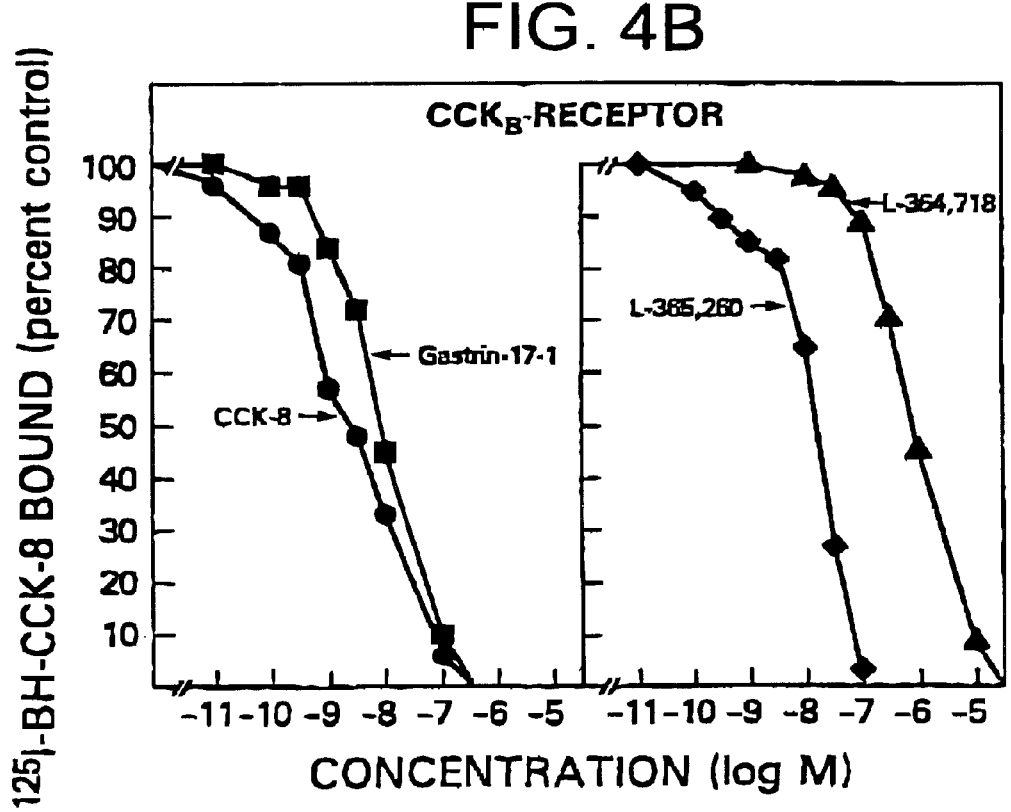
Figure 11:
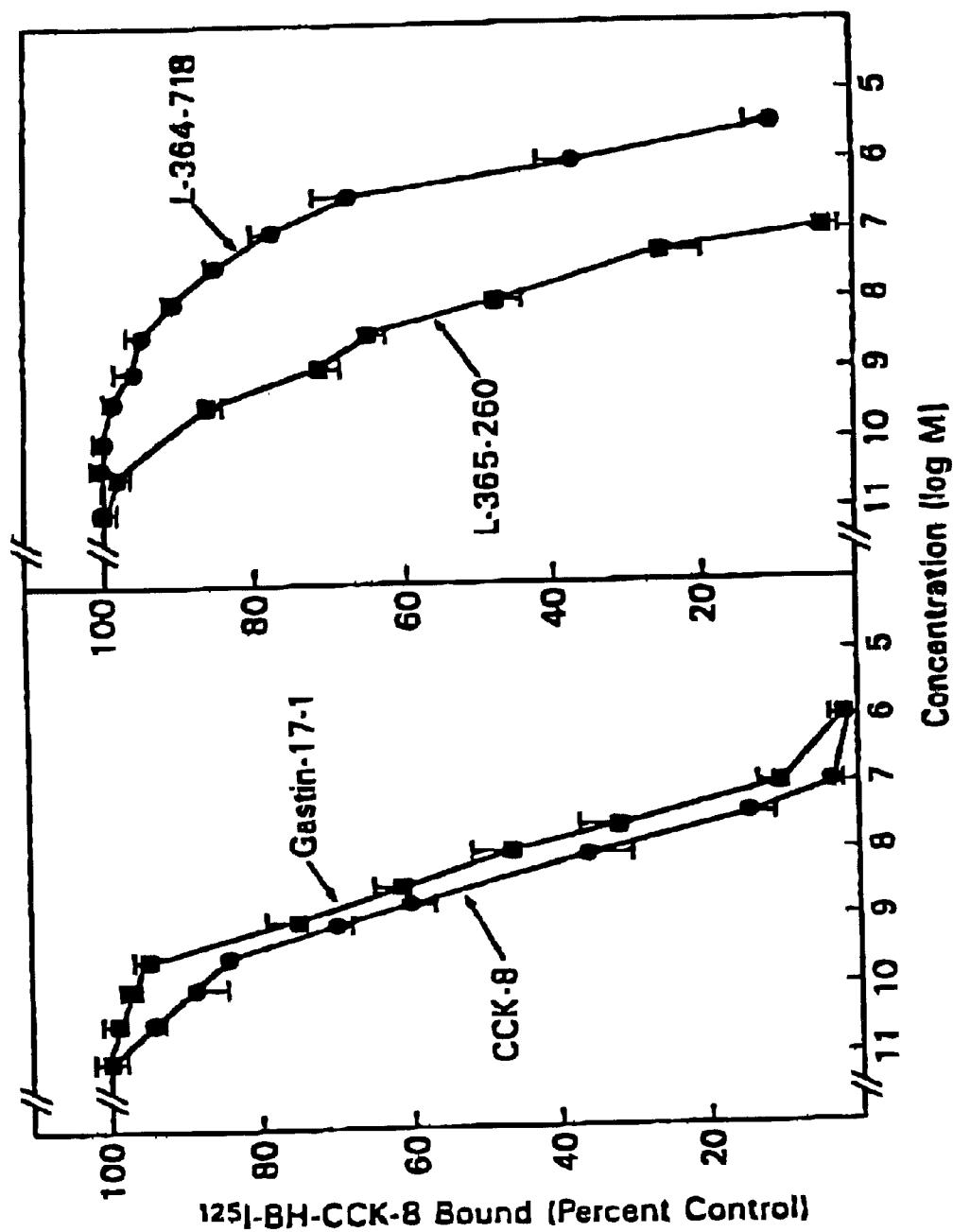
FIG. 11. Ability of CCK receptor agonists and antagonists to inhibit $^{125}$BH-CCK-8 to COS-7 cells expressing the guinea pig CCK$_B$ receptor. COS-7 cells were transfected with the expression vector pCDL-SRα containing the CCK$_B$ receptor cDNA sequence. $^{125}$I-BH-CCK 8 (50 pM) was incubated either alone or with increasing concentrations of agonists (CCK-8 and Gastrin-17-1) (left panel or antagonists (L-364,718 and L-365,260) (right panel). Data are presented as percent saturable binding (total binding in the presence of radiolabelled hormone alone minus binding in the presence of 1 μM CCK-8). The results given are means of values from at least three experiments performed in duplicate. Vertical bars are standard deviations from the mean.

A full-length cDNA coding region sequence and partial 3' untranslated sequence of the human CCK$_B$ receptor was obtained as a single PCR product using the above degenerate sense primer (SEQ ID NO:10) 5'-GGAG/CC/TTCA/GG/CA/TGGA/GGCCATGGA-3') plus an additional 5'-15-basepair sequence and a different antisense primer, (SEQ ID NO:12) 5'-ACTGACTAGTCTAGAGCTTTGGGTGTTG-GTTTCCTG-3' (containing a 5' cap sequence and a Xba1 restriction sequence). The 5'-15-basepair sequence was comprised of a cap sequence followed by an Xba1 restriction sequence. The full-length sequence and partial 3' untranslated sequence was made from these primers, digested with Xba1 endonuclease, and subcloned into PCDL-SRα vector and subcloned into COS-7 cells. The pharmacology exhibited by the expressed hCCK$_B$ protein was similar to that of guinea pig and rat CCK$_B$ receptors, as discussed above (see FIG. 4B and FIG. 11).

EXAMPLE 6

ISOLATION OF HUMAN CCK$_A$ RECEPTOR cDNA

A [$^{32}$P]-labelled rat CCK$_A$ receptor probe was used to screen a human placental genomic library in λ FIX II vector under conditions of high stringency (0.1×SSC, 42° C.). Screening of approximately 7.5×10$^5$ clones resulted in 9 plaque purified clones. PCR amplification of two of these clones using primers derived from the rat CCK$_A$ receptor resulted in products highly homologous to the 5' and 3' untranslated regions of the rat CCK$_A$ receptor cDNA sequence. Primers derived from this new human genomic sequence 5' GGCAGGTTGCATCTGCGAGAC3' (bases 54–74 of SEQ ID NO:30) and 5' CGTTCTTTCTTCTCT-GCCTCC3' (SEQ ID NO:32), were used in PCR cloning of a 1446 basepair cDNA product (nucleotides 54–1500 of FIGS. 13A–C (SEQ ID NO:30) from a human gallbladder cDNA library. This human cDNA sequence contained a single long open reading frame encoding a unique 428 amino acid protein (SEQ ID NO:32) having 91% and 92% homology to the rat and guinea pig CCK$_A$ receptors, respectively. Hydropathy analysis revealed seven regions of hydrophobic residues that correspond to putative transmembrane spanning regions expected for members of the G-protein-coupled superfamily of receptors. Similar to the rat, the sequence allows for three potential N-linked glycosylation sites and 4 potential protein kinase C phosphorylation sites.

Expression of Human CCK$_A$ Receptors in Mammalian Cells and Ligand Inhibition Studies The human CCK$_A$ receptor cDNA clone was subcloned in the mammalian expression vector PCDL-SRα and transfected into COS 7 calls using DEAE/dextran. Transient expression of cell surface receptors was assayed 48 hours post transfection for binding of $^{125}$I-Bolton-Hunter labelled CCK-8 ($^{125}$I-BH-CCK).

$^{125}$I-BH-CCK binding was specific and saturable. CCK-8 inhibited binding with high potency (IC50=10 nm) and was greater than 1000 fold more potent than gastrin-17-I. The CCK$_A$ receptor selective antagonist L-364,718 inhibited $^{125}$I-BH-CCK binding with high potency (IC50=1 nM) and was greater than 30-fold more potent than the CCK$_B$ receptor selective antagonist, L-365,260. These studies demonstrated that the cDNA cloned from human gallbladder has selective high affinity for sulfated CCK-8 and for the selective CCK$_A$ antagonist L-364,718. These studies confirmed that this receptor is a CCK$_A$ subtype.

Northern hybridization using the human CCK$_A$ receptor cDNA as a [$^{32}$P]-labelled probe identified a 5 Kb hybridizing transcript in the human gallbladder. These results describe for the first time the molecular cloning of the human CCK$_A$ receptor. This knowledge will enhance the understanding of the distribution, pharmacology and physiologic role of CCK$_A$ receptor in humans.

The CCK family of peptides interact with at least two receptor subtypes widely distributed throughout the gastrointestinal and nervous systems with some cells possessing both subtypes. The present results should allow better assignment of CCK receptor subtype distribution and function on the basis of such studies as in situ hybridization, cloning of other subtypes using low stringency hybridization methods, production of large quantities of pure receptor for immunization and screening of new more potent and selective agonists and antagonists. This should ultimately allow targeting of therapy to diseased organs of the gastrointestinal and nervous systems while sparing uninvolved organs which possess different CCK subtypes.

As will be apparent to those skilled in the art in which the invention is addressed, the present invention may be embodied in forms other than those specifically disclosed above without departing from the spirit or essential characteristics of the invention. The particular embodiments of the present invention, described above, are therefore to be considered in all respects as illustrative and not restrictive. The scope of the present invention is as set forth in the appended claims rather than being limited to the foregoing examples.

What is claimed is:

1. An isolated DNA molecule (i) encoding a CCK receptor protein or a functional fragment thereof, whereby the fragment binds to the CCK receptor family of peptides, and (ii) consisting essentially of a nucleotide sequence which comprises nucleotides 154–1437 of SEQ ID NO: 30, which encodes SEQ ID NO: 31, or which comprises a nucleotide sequence which hybridizes to an isolated nucleic acid molecule consisting essentially of nucleotides 154–1437 of SEQ ID NO: 30.

2. A cell transformed with a DNA molecule of claim 1, wherein the DNA molecule is optionally in the form of a vector.

3. The isolated DNA molecule of claim 1 consisting essentially of a nucleotide sequence which hybridizes to an isolated nucleic acid molecule consisting essentially of nucleotides 154–1437 of SEQ ID NO: 30 under conditions comprising a wash with 0.1×SSC at a temperature of 55° C.

4. The isolated DNA molecule of claim 3, wherein the conditions comprise three 20-minute washes with 0.1×SSC/0.1% SDS at a temperature of 55° C.

5. A cell transformed with a DNA molecule of claim 3, wherein the DNA molecule is optionally in the form of a vector.

6. A cell transformed with a DNA molecule of claim 4, wherein the DNA molecule is optionally in the form of a vector.

\* \* \* \* \*

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ix) FEATURE:
       (A) NAME/KEY: misc_difference
       (B) LOCATION: replace(6, "")
       (D) OTHER INFORMATION: /note= "N at position 6 represents
           Inosine"

(ix) FEATURE:
       (A) NAME/KEY: misc_difference
       (B) LOCATION: replace(14, "")
       (D) OTHER INFORMATION: /note= "N at position 14 represents
           Inosine"

(xi) SEQUENCE DESCRIPTION: SEQ ID NO:1:

ATGCCNABAA YCTNATHCCN AA                                              22

(2) INFORMATION FOR SEQ ID NO:2:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (iv) ANTI-SENSE: YES (xi) SEQUENCE DESCRIPTION: SEQ ID NO:2:

CCRTCRCTRT CYTCRTA                                                    17

(2) INFORMATION FOR SEQ ID NO:3:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (iv) ANTI-SENSE: YES (xi) SEQUENCE DESCRIPTION: SEQ ID NO:3:

CCRTCDGART CYTCRTA                                                    17

(2) INFORMATION FOR SEQ ID NO:4:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:4:

GCCAGCCAGA AGAAATCTGC C                                               21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:5:

AGCCGAGCAC TGGCAGCAGC A                              21

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:6:

ACTGACTAGT CTAGATCAGC TGCCAACCTG ATAGCC            36

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:7:

ACTGACTAGT CTAGATAATA CGACTCACTA TAGGGCG           37

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:8:

ACTGACTAGT CTAGAAATGC TTGCCCAGAT GCTCTG            36

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:9:

ACTGACTAGT CTAGACAGTG GACCAGGTGG AGTTCA            36

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:10:

GGASYTCRSW GGRGCCATGG A                              21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:11:

```
GGGCCAGCGA TGCACGCACT G                                              21
```

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:12:

```
ACTGACTAGT CTAGAGCTTT GGGTGTTGGT TTCCTG                              36
```

(2) INFORMATION FOR SEQ ID NO:13:

(i) SEQUENCE CHARACTERISTICS:
        (A) LENGTH: 1506 base pairs
        (B) TYPE: nucleic acid
        (C) STRANDEDNESS: double
        (D) TOPOLOGY: linear (ii) MOLECULE TYPE: cDNA (vii) IMMEDIATE SOURCE:
        (B) CLONE: rat pancreatic CCKA receptor (ix) FEATURE:
        (A) NAME/KEY: CDS
        (B) LOCATION: 154..1488

(xi) SEQUENCE DESCRIPTION: SEQ ID NO:13:

```
CCGCAATGCT TGCCCAGATG CTCTGAGAAT GGCGAACTCA AGTTGCCTTT AGGAATGGCT     60

GCAAAGCCCA CACCTGGAAA TCTCCCCCTC CCTGCTCCTC CACGGCAGGT TGCATTTGGG    120

AGACCCTGTG ATCATTAGAG GAGAGAGACA GGA ATG AGC CAT TCA CCA GCT CGC    174
                                   Met Ser His Ser Pro Ala Arg
                                    1               5

CAG CAC TTG GTA GAA AGC AGC AGG ATG GAC GTG GTC GAC AGC CTT CTT    222
Gln His Leu Val Glu Ser Ser Arg Met Asp Val Val Asp Ser Leu Leu
         10                  15                  20

ATG AAT GGG AGC AAC ATC ACT CCC CCC TGT GAA CTC GGA CTG GAA AAT    270
Met Asn Gly Ser Asn Ile Thr Pro Pro Cys Glu Leu Gly Leu Glu Asn
     25                  30                  35

GAG ACG CTT TTC TGC TTG GAT CAA CCT CAA CCT TCA AAA GAG TGG CAG    318
Glu Thr Leu Phe Cys Leu Asp Gln Pro Gln Pro Ser Lys Glu Trp Gln
 40                  45                  50                  55

TCT GCA CTG CAG ATT CTC CTG TAC TCC ATC ATA TTC CTT CTC AGT GTG    366
Ser Ala Leu Gln Ile Leu Leu Tyr Ser Ile Ile Phe Leu Leu Ser Val
             60                  65                  70

CTG GGG AAC ACG CTG GTT ATA ACG GTG CTG ATT CGA AAC AAG AGG ATG    414
Leu Gly Asn Thr Leu Val Ile Thr Val Leu Ile Arg Asn Lys Arg Met
         75                  80                  85
```

-continued

| | |
|---|---|
| CGG ACG GTC ACC AAC ATC TTC CTG CTG TCC CTG GCT GTC AGT GAC CTC<br>Arg Thr Val Thr Asn Ile Phe Leu Leu Ser Leu Ala Val Ser Asp Leu<br>        90                         95                      100 | 462 |
| ATG CTC TGC CTC TTC TGC ATG CCG TTC AAC CTC ATC CCC AAC CTG CTC<br>Met Leu Cys Leu Phe Cys Met Pro Phe Asn Leu Ile Pro Asn Leu Leu<br>        105                     110                     115 | 510 |
| AAG GAT TTC ATC TTC GGA AGT GCC GTG TGC AAG ACT ACC ACC TAC TTC<br>Lys Asp Phe Ile Phe Gly Ser Ala Val Cys Lys Thr Thr Thr Tyr Phe<br>120                      125                     130                    135 | 558 |
| ATG GGC ACT TCC GTG AGC GTT TCC ACC TTC AAC CTG GTA GCC ATC TCT<br>Met Gly Thr Ser Val Ser Val Ser Thr Phe Asn Leu Val Ala Ile Ser<br>             140                     145                     150 | 606 |
| CTG GAG AGA TAT GGC GCC ATC TGC AGA CCC CTA CAG TCC CGC GTC TGG<br>Leu Glu Arg Tyr Gly Ala Ile Cys Arg Pro Leu Gln Ser Arg Val Trp<br>             155                     160                     165 | 654 |
| CAA ACA AAG TCC CAT GCT TTG AAG GTC ATC GCT GCC ACC TGG TGC CTC<br>Gln Thr Lys Ser His Ala Leu Lys Val Ile Ala Ala Thr Trp Cys Leu<br>             170                     175                     180 | 702 |
| TCC TTT ACC ATC ATG ACT CCG TAC CCC ATT TAC AGC AAC TTG GTG CCT<br>Ser Phe Thr Ile Met Thr Pro Tyr Pro Ile Tyr Ser Asn Leu Val Pro<br>             185                     190                     195 | 750 |
| TTT ACT AAA AAT AAT AAC CAG ACG GCG AAC ATG TGC CGC TTC CTG TTG<br>Phe Thr Lys Asn Asn Asn Gln Thr Ala Asn Met Cys Arg Phe Leu Leu<br>200                      205                     210                    215 | 798 |
| CCA AGT GAC GCT ATG CAG CAG TCC TGG CAA ACA TTC CTG CTA CTC ATC<br>Pro Ser Asp Ala Met Gln Gln Ser Trp Gln Thr Phe Leu Leu Leu Ile<br>             220                     225                     230 | 846 |
| CTC TTT CTT CTC CCT GGG ATT GTG ATG GTG GTG GCC TAC GGG TTG ATC<br>Leu Phe Leu Leu Pro Gly Ile Val Met Val Val Ala Tyr Gly Leu Ile<br>             235                     240                     245 | 894 |
| TCT CTG GAA CTC TAC CAA GGA ATC AAA TTT GAT GCC AGC CAG AAG AAA<br>Ser Leu Glu Leu Tyr Gln Gly Ile Lys Phe Asp Ala Ser Gln Lys Lys<br>             250                     255                     260 | 942 |
| TCT GCC AAA GAG AAG AAG CCG AGC ACT GGC AGC AGC ACC CGA TAT GAG<br>Ser Ala Lys Glu Lys Lys Pro Ser Thr Gly Ser Ser Thr Arg Tyr Glu<br>             265                     270                     275 | 990 |
| GAT AGT GAT GGC TGT TAC TTG CAG AAG TCC CGG CCC CCG AGG AAG CTG<br>Asp Ser Asp Gly Cys Tyr Leu Gln Lys Ser Arg Pro Pro Arg Lys Leu<br>280                      285                     290                    295 | 1038 |
| GAG CTT CAG CAG CTG TCT AGC GGC AGC GGT GGC AGC AGA CTC AAC CGG<br>Glu Leu Gln Gln Leu Ser Ser Gly Ser Gly Gly Ser Arg Leu Asn Arg<br>             300                     305                     310 | 1086 |
| ATC AGG AGC AGC AGT TCA GCT GCC AAC CTG ATA GCC AAG AAG CGC GTG<br>Ile Arg Ser Ser Ser Ser Ala Ala Asn Leu Ile Ala Lys Lys Arg Val<br>             315                     320                    325 | 1134 |
| ATC CGC ATG CTC ATT GTC ATC GTG GTC CTC TTC TTC CTG TGC TGG ATG<br>Ile Arg Met Leu Ile Val Ile Val Val Leu Phe Phe Leu Cys Trp Met<br>             330                     335                     340 | 1182 |
| CCC ATC TTC AGC GCC AAC GCC TGG CGG GCA TAT GAC ACG GTT TCT GCC<br>Pro Ile Phe Ser Ala Asn Ala Trp Arg Ala Tyr Asp Thr Val Ser Ala<br>             345                     350                    355 | 1230 |
| GAG AAG CAC CTC TCA GGG ACT CCC ATC TCC TTC ATC CTC CTC CTC TCC<br>Glu Lys His Leu Ser Gly Thr Pro Ile Ser Phe Ile Leu Leu Leu Ser<br>360                      365                     370                    375 | 1278 |
| TAC ACC TCC TCC TGT GTT AAC CCC ATC ATC TAT TGC TTC ATG AAC AAA<br>Tyr Thr Ser Ser Cys Val Asn Pro Ile Ile Tyr Cys Phe Met Asn Lys<br>             380                     385                    390 | 1326 |
| CGC TTT CGC CTG GGC TTC ATG GCC ACC TTC CCT TGT TGC CCG AAT CCC<br>Arg Phe Arg Leu Gly Phe Met Ala Thr Phe Pro Cys Cys Pro Asn Pro<br>             395                     400                    405 | 1374 |

```
GGT CCC CCA GGG GTG AGA GGA GAG GTG GGA GAG GAG GAG GAT GGG AGG                    1422
Gly Pro Pro Gly Val Arg Gly Glu Val Gly Glu Glu Glu Asp Gly Arg
        410                 415                 420

ACC ATA AGG GCA TTG CTG TCC AGG TAT TCC TAC AGC CAC ATG AGC ACC                    1470
Thr Ile Arg Ala Leu Leu Ser Arg Tyr Ser Tyr Ser His Met Ser Thr
    425                 430                 435

TCT GCT CCA CCC CCC TGAACTCCAC CTGGTCCACT G                                        1506
Ser Ala Pro Pro Pro
440             445
```

(2) INFORMATION FOR SEQ ID NO:14:

(i) SEQUENCE CHARACTERISTICS:
        (A) LENGTH: 444 amino acids
        (B) TYPE: amino acid
        (D) TOPOLOGY: linear (ii) MOLECULE TYPE: protein (xi) SEQUENCE DESCRIPTION: SEQ ID NO:14:

```
Met Ser His Ser Pro Ala Arg Gln His Leu Val Glu Ser Ser Arg Met
 1               5                  10                  15

Asp Val Val Asp Ser Leu Leu Met Asn Gly Ser Asn Ile Thr Pro Pro
                20                  25                  30

Cys Glu Leu Gly Leu Glu Asn Glu Thr Leu Phe Cys Leu Asp Gln Pro
            35                  40                  45

Gln Pro Ser Lys Glu Trp Gln Ser Ala Leu Gln Ile Leu Leu Tyr Ser
        50                  55                  60

Ile Ile Phe Leu Leu Ser Val Leu Gly Asn Thr Leu Val Ile Thr Val
 65                  70                  75                  80

Leu Ile Arg Asn Lys Arg Met Arg Thr Val Thr Asn Ile Phe Leu Leu
                85                  90                  95

Ser Leu Ala Val Ser Asp Leu Met Leu Cys Leu Phe Cys Met Pro Phe
            100                 105                 110

Asn Leu Ile Pro Asn Leu Leu Lys Asp Phe Ile Phe Gly Ser Ala Val
            115                 120                 125

Cys Lys Thr Thr Thr Tyr Phe Met Gly Thr Ser Val Ser Val Ser Thr
            130                 135                 140

Phe Asn Leu Val Ala Ile Ser Leu Glu Arg Tyr Gly Ala Ile Cys Arg
145                 150                 155                 160

Pro Leu Gln Ser Arg Val Trp Gln Thr Lys Ser His Ala Leu Lys Val
                165                 170                 175

Ile Ala Ala Thr Trp Cys Leu Ser Phe Thr Ile Met Thr Pro Tyr Pro
            180                 185                 190

Ile Tyr Ser Asn Leu Val Pro Phe Thr Lys Asn Asn Asn Gln Thr Ala
            195                 200                 205

Asn Met Cys Arg Phe Leu Leu Pro Ser Asp Ala Met Gln Gln Ser Trp
        210                 215                 220

Gln Thr Phe Leu Leu Leu Ile Leu Phe Leu Leu Pro Gly Ile Val Met
225                 230                 235                 240

Val Val Ala Tyr Gly Leu Ile Ser Leu Glu Leu Tyr Gln Gly Ile Lys
                245                 250                 255

Phe Asp Ala Ser Gln Lys Lys Ser Ala Lys Glu Lys Lys Pro Ser Thr
            260                 265                 270

Gly Ser Ser Thr Arg Tyr Glu Asp Ser Asp Gly Cys Tyr Leu Gln Lys
            275                 280                 285
```

```
Ser Arg Pro Pro Arg Lys Leu Glu Leu Gln Gln Leu Ser Ser Gly Ser
    290                 295                 300

Gly Gly Ser Arg Leu Asn Arg Ile Arg Ser Ser Ser Ala Ala Asn
305                 310                 315                 320

Leu Ile Ala Lys Lys Arg Val Ile Arg Met Leu Ile Val Ile Val Val
                325                 330                 335

Leu Phe Phe Leu Cys Trp Met Pro Ile Phe Ser Ala Asn Ala Trp Arg
            340                 345                 350

Ala Tyr Asp Thr Val Ser Ala Glu Lys His Leu Ser Gly Thr Pro Ile
        355                 360                 365

Ser Phe Ile Leu Leu Leu Ser Tyr Thr Ser Ser Cys Val Asn Pro Ile
    370                 375                 380

Ile Tyr Cys Phe Met Asn Lys Arg Phe Arg Leu Gly Phe Met Ala Thr
385                 390                 395                 400

Phe Pro Cys Cys Pro Asn Pro Gly Pro Pro Gly Val Arg Gly Glu Val
                405                 410                 415

Gly Glu Glu Glu Asp Gly Arg Thr Ile Arg Ala Leu Leu Ser Arg Tyr
            420                 425                 430

Ser Tyr Ser His Met Ser Thr Ser Ala Pro Pro Pro
    435                 440
```

(2) INFORMATION FOR SEQ ID NO:15:

(i) SEQUENCE CHARACTERISTICS:
      (A) LENGTH: 2243 base pairs
      (B) TYPE: nucleic acid
      (C) STRANDEDNESS: double
      (D) TOPOLOGY: linear (ii) MOLECULE TYPE: cDNA (vii) IMMEDIATE SOURCE:
      (B) CLONE: rat brain CCKB receptor (ix) FEATURE:
      (A) NAME/KEY: CDS
      (B) LOCATION: 136..1494

(xi) SEQUENCE DESCRIPTION: SEQ ID NO:15:

```
TGACCCTGCT TGCTCAACTC TACGTCTTGT TTCGTTTTCT GTTCTGCGCC GTTACAGATC        60

CAAGCTCCTC GAGCCCGGGC TGCAGGAATT CTGCGGCCGC CGCTTAGCAG AGCTAAGTGG       120

GACTTCACTG GAGCC ATG GAG CTG CTC AAG CTG AAC CGC AGC GTG CAG GGA       171
             Met Glu Leu Leu Lys Leu Asn Arg Ser Val Gln Gly
               1               5                  10

CCA GGA CCC GGG TCG GGG TCT TCT TTG TGC CGC CCG GGT GTC TCC CTT        219
Pro Gly Pro Gly Ser Gly Ser Ser Leu Cys Arg Pro Gly Val Ser Leu
        15                  20                  25

CTC AAC AGC AGT AGT GCC GGG AAC CTC AGC TGT GAC CCC CCT CGT ATC        267
Leu Asn Ser Ser Ser Ala Gly Asn Leu Ser Cys Asp Pro Pro Arg Ile
    30                  35                  40

CGC GGA ACC GGG ACC AGA GAA TTG GAG ATG GCG ATT AGA ATC ACC CTT        315
Arg Gly Thr Gly Thr Arg Glu Leu Glu Met Ala Ile Arg Ile Thr Leu
45                  50                  55                  60

TAT GCA GTG ATC TTT CTG ATG AGT GTT GGC GGA AAC GTG CTC ATC ATC        363
Tyr Ala Val Ile Phe Leu Met Ser Val Gly Gly Asn Val Leu Ile Ile
                65                  70                  75

GTG GTC CTG GGA CTG AGC CGA CGC CTA AGA ACG GTC ACC AAC GCC TTC        411
Val Val Leu Gly Leu Ser Arg Arg Leu Arg Thr Val Thr Asn Ala Phe
            80                  85                  90
```

-continued

| | | |
|---|---|---|
| CTG CTC TCC CTG GCA GTC AGC GAC CTC CTG CTG GCC GTG GCT TGC ATG<br>Leu Leu Ser Leu Ala Val Ser Asp Leu Leu Leu Ala Val Ala Cys Met<br>         95                  100               105 | 459 |
| CCC TTC ACA CTC CTG CCC AAC CTC ATG GGC ACA TTC ATC TTC GGC ACA<br>Pro Phe Thr Leu Leu Pro Asn Leu Met Gly Thr Phe Ile Phe Gly Thr<br>110                   115                   120 | 507 |
| GTC ATC TGC AAG GCC ATT TCC TAC CTC ATG GGG GTA TCA GTG AGT GTA<br>Val Ile Cys Lys Ala Ile Ser Tyr Leu Met Gly Val Ser Val Ser Val<br>125                   130                   135               140 | 555 |
| TCC ACT CTA AAT CTC GTG GCC ATA GCC CTG GAG CGA TAC AGC GCC ATC<br>Ser Thr Leu Asn Leu Val Ala Ile Ala Leu Glu Arg Tyr Ser Ala Ile<br>                145                   150               155 | 603 |
| TGC CGA CCA CTG CAA GCA CGA GTA TGG CAA ACA CGC TCC CAC GCA GCT<br>Cys Arg Pro Leu Gln Ala Arg Val Trp Gln Thr Arg Ser His Ala Ala<br>                160                   165               170 | 651 |
| CGG GTG ATC TTA GCC ACG TGG CTG CTG TCT GGA CTG CTT ATG GTA CCC<br>Arg Val Ile Leu Ala Thr Trp Leu Leu Ser Gly Leu Leu Met Val Pro<br>         175                   180                   185 | 699 |
| TAC CCT GTG TAC ACC ATG GTA CAG CCA GTG GGA CCT CGA GTG CTG CAG<br>Tyr Pro Val Tyr Thr Met Val Gln Pro Val Gly Pro Arg Val Leu Gln<br>         190                   195                   200 | 747 |
| TGC ATG CAT CGC TGG CCC AGT GCA CGT GTC CAA CAA ACC TGG TCC GTG<br>Cys Met His Arg Trp Pro Ser Ala Arg Val Gln Gln Thr Trp Ser Val<br>205                   210                   215               220 | 795 |
| CTA CTG CTA CTG CTT TTG TTC TTC ATC CCG GGT GTG GTT ATT GCG GTG<br>Leu Leu Leu Leu Leu Leu Phe Phe Ile Pro Gly Val Val Ile Ala Val<br>                225                   230               235 | 843 |
| GCC TAT GGA CTC ATC TCC CGC GAA CTC TAC CTA GGA CTC CAC TTT GAT<br>Ala Tyr Gly Leu Ile Ser Arg Glu Leu Tyr Leu Gly Leu His Phe Asp<br>         240                   245                   250 | 891 |
| GGT GAA AAT GAC AGC GAG ACC CAA AGC CGG GCC CGA AAC CAA GGG GGC<br>Gly Glu Asn Asp Ser Glu Thr Gln Ser Arg Ala Arg Asn Gln Gly Gly<br>                255                   260               265 | 939 |
| CTG CCG GGT GGG GCA GCA CCA GGG CCT GTC CAC CAG AAC GGG GGC TGC<br>Leu Pro Gly Gly Ala Ala Pro Gly Pro Val His Gln Asn Gly Gly Cys<br>         270                   275                   280 | 987 |
| CGG CCT GTA ACC AGC GTA GCT GGG GAA GAC AGT GAT GGC TGC TGT GTG<br>Arg Pro Val Thr Ser Val Ala Gly Glu Asp Ser Asp Gly Cys Cys Val<br>285                   290                   295               300 | 1035 |
| CAA CTT CCG CGT TCC CGA CTG GAG ATG ACA ACG CTA ACC ACA CCC ACT<br>Gln Leu Pro Arg Ser Arg Leu Glu Met Thr Thr Leu Thr Thr Pro Thr<br>                305                   310               315 | 1083 |
| CCT GGG CCA GTC CCT GGC CCT CGG CCC AAC CAG GCC AAG CTG CTG GCT<br>Pro Gly Pro Val Pro Gly Pro Arg Pro Asn Gln Ala Lys Leu Leu Ala<br>         320                   325                   330 | 1131 |
| AAG AAG CGG GTG GTG CGA ATG CTG CTA GTG ATT GTT TTG CTT TTC TTC<br>Lys Lys Arg Val Val Arg Met Leu Leu Val Ile Val Leu Leu Phe Phe<br>         335                   340               345 | 1179 |
| CTG TGT TGG CTG CCA GTG TAC AGC GTC AAC ACG TGG CGC GCC TTC GAT<br>Leu Cys Trp Leu Pro Val Tyr Ser Val Asn Thr Trp Arg Ala Phe Asp<br>350                   355                   360 | 1227 |
| GGC CCA GGC GCA CAA CGA GCA CTC TCA GGG GCC CCT ATC TCT TTC ATC<br>Gly Pro Gly Ala Gln Arg Ala Leu Ser Gly Ala Pro Ile Ser Phe Ile<br>365                   370                   375               380 | 1275 |
| CAC TTG CTG AGC TAC GTC TCT GCT TGT GTC AAC CCC CTG GTC TAC TGT<br>His Leu Leu Ser Tyr Val Ser Ala Cys Val Asn Pro Leu Val Tyr Cys<br>                385                   390               395 | 1323 |
| TTC ATG CAC CGC CGC TTC CGC CAG GCC TGC CTG GAC ACA TGT GCC CGC<br>Phe Met His Arg Arg Phe Arg Gln Ala Cys Leu Asp Thr Cys Ala Arg<br>         400                   405                   410 | 1371 |

```
TGT TGC CCA CGC CCT CCA CGA GCT CGC CCA CAG CCT CTT CCA GAT GAG    1419
Cys Cys Pro Arg Pro Pro Arg Ala Arg Pro Gln Pro Leu Pro Asp Glu
        415                 420                 425

GAT CCT CCT ACC CCC TCC ATC GCT TCG CTG TCC AGG CTA AGC TAT ACC    1467
Asp Pro Pro Thr Pro Ser Ile Ala Ser Leu Ser Arg Leu Ser Tyr Thr
    430                 435                 440

ACC ATC AGC ACA CTG GGG CCT GGC TGAGGGGTTG GGAGATTGGA GAAAGAGACA   1521
Thr Ile Ser Thr Leu Gly Pro Gly
445                 450

AGATACATAA TTACTATCAA ATGACCCATC CAAACACATA AGAAACAAAA TTCAGAATTA  1581

ATCAGGTGAA CACCCAACAC CATGGACAGA CCCCTACACA CAGAAAATAG TATCTTTGCT  1641

GCCCTACCTG AAACAGATAG GAGTCTCATA GGAAAGGAGG CTCACTTCTG ATAAGGGGCT  1701

GAGTCCCTTC CTAGACATCT TGCACTGACC CCATTACATG GACAGACACA AGGTCCGTAG  1761

CAGTAAACTT TACCTATAAA GGGGAACTCT GACAAGGGCT GATTGGCTCC TCATATGAAC  1821

ATATTACTGA CACTATTCTG TAGTGCCCAT AGCCTAGTGC AGAAGTGACT TAGGACATTG  1881

TGGCTGTTCC CGTTTGACTT CATTATTGCC TTCCTCATCC AGCACTGAAA TTATCAACCA  1941

CACGCCTTTC ACCTTTCGGA GCTGCCGATC GTTCAGCACT GAAAAGTCCC CCCCCCCAC   2001

TCCTTTCCAT TGGAGACTGT GGAAAGTCCT CTTCCCTCCT GCCTCTCCTC CCTCACCAGA  2061

CCACATCATA AAAGGATAAG TGACTTAGTG TCCTCCTGGA CTTCTTGAGG TAGGTGAACA  2121

GGTGTGGTTT ATGGGAAGCT TCTTCATTTA TTGGCTCCCA TGACTAATCT ACCCCATATC  2181

CAACCTTGTG CAAAAAGGCC AGGGTATGAA GATAGGGATG AGCGTACCCT CTCTTGGTTG  2241

TC                                                                 2243

(2) INFORMATION FOR SEQ ID NO:16:

(i) SEQUENCE CHARACTERISTICS:
        (A) LENGTH: 452 amino acids
        (B) TYPE: amino acid
        (D) TOPOLOGY: linear (ii) MOLECULE TYPE: protein (xi) SEQUENCE DESCRIPTION: SEQ ID NO:16:

Met Glu Leu Leu Lys Leu Asn Arg Ser Val Gln Gly Pro Gly Pro Gly
 1               5                  10                  15

Ser Gly Ser Ser Leu Cys Arg Pro Gly Val Ser Leu Leu Asn Ser Ser
                20                  25                  30

Ser Ala Gly Asn Leu Ser Cys Asp Pro Pro Arg Ile Arg Gly Thr Gly
            35                  40                  45

Thr Arg Glu Leu Glu Met Ala Ile Arg Ile Thr Leu Tyr Ala Val Ile
        50                  55                  60

Phe Leu Met Ser Val Gly Gly Asn Val Leu Ile Ile Val Val Leu Gly
 65                 70                  75                  80

Leu Ser Arg Arg Leu Arg Thr Val Thr Asn Ala Phe Leu Leu Ser Leu
                85                  90                  95

Ala Val Ser Asp Leu Leu Leu Ala Val Ala Cys Met Pro Phe Thr Leu
            100                 105                 110

Leu Pro Asn Leu Met Gly Thr Phe Ile Phe Gly Thr Val Ile Cys Lys
        115                 120                 125

Ala Ile Ser Tyr Leu Met Gly Val Ser Val Ser Val Ser Thr Leu Asn
    130                 135                 140

Leu Val Ala Ile Ala Leu Glu Arg Tyr Ser Ala Ile Cys Arg Pro Leu
145                 150                 155                 160
```

-continued

Gln Ala Arg Val Trp Gln Thr Arg Ser His Ala Ala Arg Val Ile Leu
                165                 170                 175

Ala Thr Trp Leu Leu Ser Gly Leu Leu Met Val Pro Tyr Pro Val Tyr
            180                 185                 190

Thr Met Val Gln Pro Val Gly Pro Arg Val Leu Gln Cys Met His Arg
        195                 200                 205

Trp Pro Ser Ala Arg Val Gln Gln Thr Trp Ser Val Leu Leu Leu
    210                 215                 220

Leu Leu Phe Phe Ile Pro Gly Val Val Ile Ala Val Ala Tyr Gly Leu
225                 230                 235                 240

Ile Ser Arg Glu Leu Tyr Leu Gly Leu His Phe Asp Gly Glu Asn Asp
                245                 250                 255

Ser Glu Thr Gln Ser Arg Ala Arg Asn Gln Gly Gly Leu Pro Gly Gly
            260                 265                 270

Ala Ala Pro Gly Pro Val His Gln Asn Gly Gly Cys Arg Pro Val Thr
        275                 280                 285

Ser Val Ala Gly Glu Asp Ser Asp Gly Cys Cys Val Gln Leu Pro Arg
    290                 295                 300

Ser Arg Leu Glu Met Thr Thr Leu Thr Thr Pro Thr Pro Gly Pro Val
305                 310                 315                 320

Pro Gly Pro Arg Pro Asn Gln Ala Lys Leu Leu Ala Lys Lys Arg Val
                325                 330                 335

Val Arg Met Leu Leu Val Ile Val Leu Leu Phe Phe Leu Cys Trp Leu
            340                 345                 350

Pro Val Tyr Ser Val Asn Thr Trp Arg Ala Phe Asp Gly Pro Gly Ala
        355                 360                 365

Gln Arg Ala Leu Ser Gly Ala Pro Ile Ser Phe Ile His Leu Leu Ser
    370                 375                 380

Tyr Val Ser Ala Cys Val Asn Pro Leu Val Tyr Cys Phe Met His Arg
385                 390                 395                 400

Arg Phe Arg Gln Ala Cys Leu Asp Thr Cys Ala Arg Cys Cys Pro Arg
                405                 410                 415

Pro Pro Arg Ala Arg Pro Gln Pro Leu Pro Asp Glu Asp Pro Pro Thr
            420                 425                 430

Pro Ser Ile Ala Ser Leu Ser Arg Leu Ser Tyr Thr Thr Ile Ser Thr
        435                 440                 445

Leu Gly Pro Gly
    450

(2) INFORMATION FOR SEQ ID NO:17:

(i) SEQUENCE CHARACTERISTICS:
        (A) LENGTH: 384 amino acids
        (B) TYPE: amino acid
        (D) TOPOLOGY: linear (vii) IMMEDIATE SOURCE:
        (B) CLONE: mouse gastrin-releasing peptide receptor (xi) SEQUENCE DESCRIPTION: SEQ ID NO:17:

Met Ala Pro Asn Asn Cys Ser His Leu Asn Leu Asp Val Asp Pro Phe
1               5                   10                  15

Leu Ser Cys Asn Asp Thr Phe Asn Gln Ser Leu Ser Pro Pro Lys Met
            20                  25                  30

Asp Asn Trp Phe His Pro Gly Phe Ile Tyr Val Ile Pro Ala Val Tyr
        35                  40                  45

```
Gly Leu Ile Ile Val Ile Gly Leu Ile Gly Asn Ile Thr Leu Ile Lys
             50                  55                  60

Ile Phe Cys Thr Val Lys Ser Met Arg Asn Val Pro Asn Leu Phe Ile
 65                  70                  75                  80

Ser Ser Leu Ala Leu Gly Asp Leu Leu Leu Val Thr Cys Ala Pro
                     85                  90                  95

Val Asp Ala Ser Lys Tyr Leu Ala Asp Arg Trp Leu Phe Gly Arg Ile
                    100                 105                 110

Gly Cys Lys Leu Ile Pro Phe Ile Gln Leu Thr Ser Val Gly Val Ser
                    115                 120                 125

Val Phe Thr Leu Thr Ala Leu Ser Ala Asp Arg Tyr Lys Ala Ile Val
                    130                 135                 140

Arg Pro Met Asp Ile Gln Ala Ser His Ala Leu Met Lys Ile Cys Leu
145                 150                 155                 160

Lys Ala Ala Leu Ile Trp Ile Val Ser Met Leu Leu Ala Ile Pro Glu
                    165                 170                 175

Ala Val Phe Ser Asp Leu His Pro Phe His Val Lys Asp Thr Asn Gln
                    180                 185                 190

Thr Phe Ile Ser Cys Ala Pro Tyr Pro His Ser Asn Glu Leu His Pro
                    195                 200                 205

Lys Ile His Ser Met Ala Ser Phe Leu Val Phe Tyr Val Ile Pro Leu
210                 215                 220

Ala Ile Ile Ser Val Tyr Tyr Tyr Phe Ile Ala Arg Asn Leu Ile Gln
225                 230                 235                 240

Ser Ala Tyr Asn Leu Pro Val Glu Gly Asn Ile His Val Lys Lys Gln
                    245                 250                 255

Ile Glu Ser Arg Lys Arg Leu Ala Lys Thr Val Leu Val Phe Val Gly
                    260                 265                 270

Leu Phe Ala Phe Cys Trp Leu Pro Asn His Val Ile Tyr Leu Tyr Arg
                    275                 280                 285

Ser Tyr His Tyr Ser Glu Val Asp Thr Ser Met Leu His Phe Val Thr
290                 295                 300

Ser Ile Cys Ala His Leu Leu Ala Phe Thr Asn Ser Cys Val Asn Pro
305                 310                 315                 320

Phe Ala Leu Tyr Leu Leu Ser Lys Ser Phe Arg Lys Gln Phe Asn Thr
                    325                 330                 335

Gln Leu Leu Cys Cys Gln Pro Gly Leu Met Asn Arg Ser His Ser Thr
                    340                 345                 350

Gly Arg Ser Thr Thr Cys Met Thr Ser Phe Lys Ser Thr Asn Pro Ser
                    355                 360                 365

Ala Thr Phe Ser Leu Ile Asn Arg Asn Ile Cys His Glu Gly Tyr Val
                    370                 375                 380
```

(2) INFORMATION FOR SEQ ID NO:18:

(i) SEQUENCE CHARACTERISTICS:
        (A) LENGTH: 390 amino acids
        (B) TYPE: amino acid
        (D) TOPOLOGY: linear (vii) IMMEDIATE SOURCE:
        (B) CLONE: rat neuromedin B receptor (xi) SEQUENCE DESCRIPTION: SEQ ID NO:18:

```
Met Pro Pro Arg Ser Leu Pro Asn Leu Ser Leu Pro Thr Glu Ala Ser
 1               5                  10                  15
```

-continued

```
Glu Ser Glu Leu Glu Pro Glu Val Trp Glu Asn Asp Phe Leu Pro Asp
             20                  25                  30
Ser Asp Gly Thr Thr Ala Glu Leu Val Ile Arg Cys Val Ile Pro Ser
         35                  40                  45
Leu Tyr Leu Ile Ile Ile Ser Val Gly Leu Leu Gly Asn Ile Met Leu
 50                  55                  60
Val Lys Ile Phe Leu Thr Asn Ser Thr Met Arg Ser Val Pro Asn Ile
 65                  70                  75                  80
Phe Ile Ser Asn Leu Ala Ala Gly Asp Leu Leu Leu Leu Thr Cys
                 85                  90                  95
Val Pro Val Asp Ala Ser Arg Tyr Phe Phe Asp Glu Trp Val Phe Gly
                100                 105                 110
Lys Leu Gly Cys Lys Leu Ile Pro Ala Ile Gln Leu Thr Ser Val Gly
             115                 120                 125
Val Ser Val Phe Thr Leu Thr Ala Leu Ser Ala Asp Arg Tyr Arg Ala
         130                 135                 140
Ile Val Asn Pro Met Asp Met Gln Thr Ser Gly Val Val Leu Trp Thr
145                 150                 155                 160
Ser Leu Lys Ala Val Gly Ile Trp Val Val Ser Val Leu Leu Ala Val
                165                 170                 175
Pro Glu Ala Val Phe Ser Glu Val Ala Arg Ile Gly Ser Ser Asp Asn
                180                 185                 190
Ser Ser Phe Thr Ala Cys Ile Pro Tyr Pro Gln Thr Asp Glu Leu His
             195                 200                 205
Pro Lys Ile His Ser Val Leu Ile Phe Leu Val Tyr Phe Leu Ile Pro
         210                 215                 220
Leu Val Ile Ile Ser Ile Tyr Tyr Tyr His Ile Ala Lys Thr Leu Ile
225                 230                 235                 240
Arg Ser Ala His Asn Leu Pro Gly Glu Tyr Asn Glu His Thr Lys Lys
                245                 250                 255
Gln Met Glu Thr Arg Lys Arg Leu Ala Lys Ile Val Leu Val Phe Val
                260                 265                 270
Gly Cys Phe Val Phe Cys Trp Phe Pro Asn His Ile Leu Tyr Leu Tyr
         275                 280                 285
Arg Ser Phe Asn Tyr Lys Glu Ile Asp Pro Ser Leu Gly His Met Ile
 290                 295                 300
Val Thr Leu Val Ala Arg Val Leu Ser Phe Ser Asn Ser Cys Val Asn
305                 310                 315                 320
Pro Phe Ala Leu Tyr Leu Leu Ser Glu Ser Phe Arg Lys His Phe Asn
                325                 330                 335
Ser Gln Leu Cys Cys Gly Gln Lys Ser Tyr Pro Glu Arg Ser Thr Ser
             340                 345                 350
Tyr Leu Leu Ser Ser Ser Ala Val Arg Met Thr Ser Leu Lys Ser Asn
         355                 360                 365
Ala Lys Asn Val Val Thr Asn Ser Val Leu Leu Asn Gly His Ser Thr
     370                 375                 380
Lys Gln Glu Ile Ala Leu
385                 390
```

(2) INFORMATION FOR SEQ ID NO:19:

(i) SEQUENCE CHARACTERISTICS:
        (A) LENGTH: 369 amino acids
        (B) TYPE: amino acid
        (D) TOPOLOGY: linear -continued (vii) IMMEDIATE SOURCE:
   (B) CLONE: rat substance K receptor (xi) SEQUENCE DESCRIPTION: SEQ ID NO:19:

Met Gly Thr Arg Ala Ile Val Ser Asp Ala Asn Ile Leu Ser Gly Leu
1               5                   10                  15

Glu Ser Asn Ala Thr Gly Val Thr Ala Phe Ser Met Pro Gly Trp Gln
            20                  25                  30

Leu Ala Leu Trp Ala Thr Ala Tyr Leu Ala Leu Val Leu Val Ala Val
        35                  40                  45

Thr Gly Asn Ala Thr Val Ile Trp Ile Ile Leu Ala His Glu Arg Met
    50                  55                  60

Arg Thr Val Thr Asn Tyr Phe Ile Ile Asn Leu Ala Leu Ala Asp Leu
65                  70                  75                  80

Cys Met Ala Ala Phe Asn Ala Thr Phe Asn Phe Ile Tyr Ala Ser His
            85                  90                  95

Asn Ile Trp Tyr Phe Gly Arg Ala Phe Cys Tyr Phe Gln Asn Leu Phe
            100                 105                 110

Pro Ile Thr Ala Met Phe Val Ser Ile Tyr Ser Met Thr Ala Ile Ala
            115                 120                 125

Ala Asp Arg Tyr Met Ala Ile Val His Pro Phe Gln Pro Arg Leu Ser
130                 135                 140

Ala Pro Ser Thr Lys Ala Ile Ile Ala Gly Ile Trp Leu Val Ala Leu
145                 150                 155                 160

Ala Leu Ala Ser Pro Gln Cys Phe Tyr Ser Thr Ile Thr Val Asp Glu
            165                 170                 175

Gly Ala Thr Lys Cys Val Val Ala Trp Pro Asn Asp Asn Gly Gly Lys
            180                 185                 190

Met Leu Leu Leu Tyr His Leu Val Val Phe Val Leu Ile Tyr Phe Leu
            195                 200                 205

Pro Leu Leu Val Met Phe Gly Ala Tyr Ser Val Ile Gly Leu Thr Leu
            210                 215                 220

Trp Lys Arg Ala Val Pro Arg His Gln Ala His Gly Ala Asn Leu Arg
225                 230                 235                 240

His Leu Gln Ala Lys Lys Lys Phe Val Lys Ala Met Val Leu Val Val
            245                 250                 255

Leu Thr Phe Ala Ile Cys Trp Leu Pro Tyr His Leu Tyr Phe Ile Leu
            260                 265                 270

Gly Thr Phe Gln Glu Asp Ile Tyr Tyr His Lys Phe Ile Gln Gln Val
            275                 280                 285

Tyr Leu Ala Leu Phe Trp Leu Ala Met Ser Ser Thr Met Tyr Asn Pro
            290                 295                 300

Ile Ile Tyr Cys Cys Leu Asn His Arg Phe Arg Ser Gly Phe Arg Leu
305                 310                 315                 320

Ala Phe Arg Cys Cys Pro Trp Val Thr Pro Thr Glu Glu Asp Arg Leu
            325                 330                 335

Glu Leu Thr His Thr Pro Ser Leu Ser Arg Arg Val Asn Arg Cys His
            340                 345                 350

Thr Lys Glu Thr Leu Phe Met Thr Gly Asp Met Thr His Ser Glu Ala
            355                 360                 365

Thr

-continued (2) INFORMATION FOR SEQ ID NO:20:

(i) SEQUENCE CHARACTERISTICS:
        (A) LENGTH: 372 amino acids
        (B) TYPE: amino acid
        (D) TOPOLOGY: linear (vii) IMMEDIATE SOURCE:
        (B) CLONE: rat substance P receptor (xi) SEQUENCE DESCRIPTION: SEQ ID NO:20:

```
Met Asp Asn Val Leu Pro Met Asp Ser Asp Leu Phe Pro Asn Ile Ser
1               5                   10                  15

Thr Asn Thr Ser Glu Ser Asn Gln Phe Val Gln Pro Thr Trp Gln Ile
            20                  25                  30

Val Leu Trp Ala Ala Ala Tyr Thr Val Ile Val Val Thr Ser Val Val
        35                  40                  45

Gly Asn Val Val Val Ile Trp Ile Ile Leu Ala His Lys Arg Met Arg
    50                  55                  60

Thr Val Thr Asn Tyr Phe Leu Val Asn Leu Ala Phe Ala Glu Ala Cys
65              70                  75                  80

Met Ala Ala Phe Asn Thr Val Val Asn Phe Thr Tyr Ala Val His Asn
                85                  90                  95

Val Trp Tyr Tyr Gly Leu Phe Tyr Cys Lys Phe His Asn Phe Phe Pro
            100                 105                 110

Ile Ala Ala Leu Phe Ala Ser Ile Tyr Ser Met Thr Ala Val Ala Phe
        115                 120                 125

Asp Arg Tyr Met Ala Ile Ile His Pro Leu Gln Pro Arg Leu Ser Ala
    130                 135                 140

Thr Ala Thr Lys Val Val Ile Phe Val Ile Trp Val Leu Ala Leu Leu
145                 150                 155                 160

Leu Ala Phe Pro Gln Gly Tyr Tyr Ser Thr Thr Glu Thr Met Pro Ser
                165                 170                 175

Arg Val Val Cys Met Ile Glu Trp Pro Glu His Pro Asn Arg Thr Tyr
            180                 185                 190

Glu Lys Ala Tyr His Ile Cys Val Thr Val Leu Ile Tyr Phe Leu Pro
        195                 200                 205

Leu Leu Val Ile Gly Tyr Ala Tyr Thr Val Val Gly Ile Thr Leu Trp
    210                 215                 220

Ala Ser Glu Ile Pro Gly Asp Ser Ser Asp Arg Tyr His Glu Gln Val
225                 230                 235                 240

Ser Ala Lys Arg Lys Val Val Lys Met Met Ile Val Val Val Cys Thr
                245                 250                 255

Phe Ala Ile Cys Trp Leu Pro Phe His Val Phe Phe Leu Leu Pro Tyr
            260                 265                 270

Ile Asn Pro Asp Leu Tyr Leu Lys Lys Phe Ile Gln Gln Val Tyr Leu
        275                 280                 285

Ala Ser Met Trp Leu Ala Met Ser Ser Thr Met Tyr Asn Pro Ile Ile
    290                 295                 300

Tyr Cys Cys Leu Asn Asp Arg Phe Arg Leu Gly Phe Lys His Ala Phe
305                 310                 315                 320

Arg Cys Cys Pro Phe Ile Ser Ala Gly Asp Tyr Glu Gly Leu Glu Met
                325                 330                 335

Lys Ser Thr Arg Tyr Leu Gln Thr Gln Ser Ser Val Tyr Lys Val Ser
            340                 345                 350
```

```
Arg Leu Glu Thr Thr Ile Ser Thr Val Val Gly Ala His Glu Glu Glu
            355                 360                 365
Pro Glu Glu Gly
    370

(2) INFORMATION FOR SEQ ID NO:21:

(i) SEQUENCE CHARACTERISTICS:
        (A) LENGTH: 411 amino acids
        (B) TYPE: amino acid
        (D) TOPOLOGY: linear (xi) SEQUENCE DESCRIPTION: SEQ ID NO:21:

Met Ala Ser Val Pro Arg Gly Glu Asn Trp Thr Asp Gly Thr Val Glu
1               5                   10                  15

Val Gly Thr His Thr Gly Asn Leu Ser Ser Ala Leu Gly Val Thr Glu
            20                  25                  30

Trp Leu Ala Leu Gln Ala Gly Asn Phe Ser Ser Ala Leu Gly Leu Pro
        35                  40                  45

Ala Thr Thr Gln Ala Pro Ser Gln Val Arg Ala Asn Leu Thr Asn Gln
    50                  55                  60

Phe Val Gln Pro Ser Trp Arg Ile Ala Leu Trp Ser Leu Ala Tyr Gly
65                  70                  75                  80

Leu Val Val Ala Val Ala Val Phe Gly Asn Leu Ile Val Ile Trp Ile
                85                  90                  95

Ile Leu Ala His Lys Arg Met Arg Thr Val Thr Asn Tyr Phe Leu Val
                100                 105                 110

Asn Leu Ala Phe Ser Asp Ala Ser Val Ala Ala Phe Asn Thr Leu Ile
            115                 120                 125

Asn Phe Ile Tyr Gly Leu His Ser Glu Trp Tyr Phe Gly Ala Asn Tyr
130                 135                 140

Cys Arg Phe Gln Asn Phe Phe Pro Ile Thr Ala Val Phe Ala Ser Ile
145                 150                 155                 160

Tyr Ser Met Thr Ala Ile Ala Val Asp Arg Tyr Met Ala Ile Ile Asp
                165                 170                 175

Pro Leu Lys Pro Arg Leu Ser Ala Thr Ala Thr Lys Ile Val Ile Gly
            180                 185                 190

Ser Ile Trp Ile Leu Ala Phe Leu Leu Ala Phe Pro Gln Cys Leu Tyr
        195                 200                 205

Ser Lys Ile Lys Val Met Pro Gly Arg Thr Leu Cys Tyr Val Gln Trp
    210                 215                 220

Pro Glu Gly Pro Lys Gln His Phe Thr Tyr His Ile Ile Val Ile Ile
225                 230                 235                 240

Leu Val Tyr Cys Phe Pro Leu Leu Ile Met Gly Val Thr Tyr Thr Ile
                245                 250                 255

Val Gly Ile Thr Leu Trp Gly Gly Glu Ile Pro Gly Asp Thr Cys Asp
            260                 265                 270

Lys Tyr His Glu Gln Leu Lys Ala Lys Arg Lys Val Val Lys Met Met
        275                 280                 285

Ile Ile Val Val Val Thr Phe Ala Ile Cys Trp Leu Pro Tyr His Val
    290                 295                 300

Tyr Phe Ile Leu Thr Ala Ile Tyr Gln Gln Leu Asn Arg Trp Lys Tyr
305                 310                 315                 320

Ile Gln Gln Val Tyr Leu Ala Ser Phe Trp Leu Ala Met Ser Ser Thr
                325                 330                 335
```

-continued

```
Met Tyr Asn Pro Ile Ile Tyr Cys Cys Leu Asn Lys Arg Phe Arg Ala
            340                 345                 350

Gly Phe Lys Arg Ala Phe Arg Trp Cys Pro Phe Ile Gln Val Ser Ser
            355                 360                 365

Tyr Asp Glu Leu Glu Leu Lys Thr Thr Arg Phe His Pro Thr Arg Gln
            370                 375                 380

Ser Ser Leu Tyr Thr Val Ser Arg Met Glu Ser Val Thr Val Leu Phe
385                 390                 395                 400

Asp Pro Asn Asp Gly Asp Pro Thr Lys Ser Ser
                405                 410
```

(2) INFORMATION FOR SEQ ID NO:22:

(i) SEQUENCE CHARACTERISTICS:
        (A) LENGTH: 1621 base pairs
        (B) TYPE: nucleic acid
        (C) STRANDEDNESS: double
        (D) TOPOLOGY: linear (vii) IMMEDIATE SOURCE:
        (B) CLONE: guinea pig gallbladder and pancreas CCKA
            receptor (ix) FEATURE:
        (A) NAME/KEY: CDS
        (B) LOCATION: 205..1497

(xi) SEQUENCE DESCRIPTION: SEQ ID NO:22:

```
CGCAGGATGC GTGCCCAGCT GGACGGAGGG TAGTGAACTC CAGGTGCCTT TAGGAATGGC      60

TGCAAAAGCC CACACCTGGC AATCACTCTC TGCCTGCCTC TCCCCGGCAG GTTGCATTTG     120

GGAGGCGCTC TGGTCATCAG AGGAATGAGC GTGGAGAGAG CTGTTTGCCA GCCCGCCAGC     180

CCCTGGTGGG AAGCAGAGGC GAGG ATG GAC GTG GTA GAC AGC CTT TTT GTG        231
                          Met Asp Val Val Asp Ser Leu Phe Val
                           1               5

AAT GGG AGC AAC ATC ACT TCT GCC TGC GAG CTC GGC TTT GAA AAT GAG       279
Asn Gly Ser Asn Ile Thr Ser Ala Cys Glu Leu Gly Phe Glu Asn Glu
 10              15                  20                  25

ACA CTT TTC TGC TTG GAT CGG CCC CGG CCT TCC AAA GAG TGG CAG CCG       327
Thr Leu Phe Cys Leu Asp Arg Pro Arg Pro Ser Lys Glu Trp Gln Pro
             30                  35                  40

GCG GTG CAG ATT CTC TTG TAT TCC TTG ATA TTC CTG CTC AGC GTG CTG       375
Ala Val Gln Ile Leu Leu Tyr Ser Leu Ile Phe Leu Leu Ser Val Leu
                 45                  50                  55

GGA AAC ACG CTG GTA ATC ACG GTG CTG ATT CGG AAC AAG AGG ATG AGG       423
Gly Asn Thr Leu Val Ile Thr Val Leu Ile Arg Asn Lys Arg Met Arg
             60                  65                  70

ACG GTC ACT AAC ATC TTC CTG CTC TCA CTG GCT GTC AGT GAC CTC ATG       471
Thr Val Thr Asn Ile Phe Leu Leu Ser Leu Ala Val Ser Asp Leu Met
 75                  80                  85

CTC TGC CTC TTC TGC ATG CCC TTC AAC CTC ATC CCC AGC CTG CTC AAG       519
Leu Cys Leu Phe Cys Met Pro Phe Asn Leu Ile Pro Ser Leu Leu Lys
 90                  95                 100                 105

GAT TTC ATC TTC GGG AGT GCC GTG TGC AAG ACC ACC ACC TAC TTC ATG       567
Asp Phe Ile Phe Gly Ser Ala Val Cys Lys Thr Thr Thr Tyr Phe Met
             110                 115                 120

GGC ACC TCT GTG AGT GTA TCC ACC TTT AAT CTG GTG GCC ATA TCG CTG       615
Gly Thr Ser Val Ser Val Ser Thr Phe Asn Leu Val Ala Ile Ser Leu
             125                 130                 135

GAG AGA TAC GGA GCA ATT TGC AAA CCC TTA CAG TCC CGC GTC TGG CAA       663
Glu Arg Tyr Gly Ala Ile Cys Lys Pro Leu Gln Ser Arg Val Trp Gln
             140                 145                 150
```

```
ACA AAG TCG CAT GCT TTG AAG GTG ATT GCT GCT ACC TGG TGC CTC TCC        711
Thr Lys Ser His Ala Leu Lys Val Ile Ala Ala Thr Trp Cys Leu Ser
    155                 160                 165

TTT ACC ATC ATG ACC CCC TAC CCC ATC TAC AGC AAC CTG GTG CCT TTT        759
Phe Thr Ile Met Thr Pro Tyr Pro Ile Tyr Ser Asn Leu Val Pro Phe
170                 175                 180                 185

ACC AAA AAT AAC AAC CAG ACC GGG AAC ATG TGC CGC TTC CTA CTG CCA        807
Thr Lys Asn Asn Asn Gln Thr Gly Asn Met Cys Arg Phe Leu Leu Pro
                190                 195                 200

AAC GAT GTT ATG CAG CAG ACC TGG CAC ACT TTC CTG TTA CTC ATC CTC        855
Asn Asp Val Met Gln Gln Thr Trp His Thr Phe Leu Leu Leu Ile Leu
            205                 210                 215

TTT CTT ATT CCC GGA ATT GTG ATG ATG GTG GCA TAT GGA CTG ATT TCT        903
Phe Leu Ile Pro Gly Ile Val Met Met Val Ala Tyr Gly Leu Ile Ser
        220                 225                 230

CTG GAA CTT TAC CAA GGA ATA AAA TTC GAT GCT ATC CAG AAG AAA TCT        951
Leu Glu Leu Tyr Gln Gly Ile Lys Phe Asp Ala Ile Gln Lys Lys Ser
    235                 240                 245

GCT AAA GAA AGG AAG ACA AGC ACT GGC AGT AGT GGC CCG ATG GAG GAC        999
Ala Lys Glu Arg Lys Thr Ser Thr Gly Ser Ser Gly Pro Met Glu Asp
250                 255                 260                 265

AGT GAT GGG TGT TAC CTG CAG AAG TCC AGG CAC CCC AGA AAG CTG GAG       1047
Ser Asp Gly Cys Tyr Leu Gln Lys Ser Arg His Pro Arg Lys Leu Glu
                270                 275                 280

CTT CGG CAG CTG TCC CCC AGC AGC AGT GGC AGC AAC AGG ATC AAT CGT       1095
Leu Arg Gln Leu Ser Pro Ser Ser Ser Gly Ser Asn Arg Ile Asn Arg
            285                 290                 295

ATC CGG AGC AGC AGC TCC ACC GCC AAC TTG ATG GCC AAA AAG CGG GTG       1143
Ile Arg Ser Ser Ser Ser Thr Ala Asn Leu Met Ala Lys Lys Arg Val
        300                 305                 310

ATC CGC ATG CTC ATC GTC ATT GTG GTC CTC TTC TTC CTG TGC TGG ATG       1191
Ile Arg Met Leu Ile Val Ile Val Val Leu Phe Phe Leu Cys Trp Met
    315                 320                 325

CCC ATC TTC AGC GCC AAT GCC TGG CGG GCA TAC GAC ACC GTC TCT GCC       1239
Pro Ile Phe Ser Ala Asn Ala Trp Arg Ala Tyr Asp Thr Val Ser Ala
330                 335                 340                 345

GAG CGC CAC CTC TCT GGG ACA CCT ATC TCC TTC ATC CTC CTG CTC TCT       1287
Glu Arg His Leu Ser Gly Thr Pro Ile Ser Phe Ile Leu Leu Leu Ser
                350                 355                 360

TAC ACC TCC TCC TGC GTC AAC CCC ATC ATC TAC TGC TTC ATG AAC AAA       1335
Tyr Thr Ser Ser Cys Val Asn Pro Ile Ile Tyr Cys Phe Met Asn Lys
            365                 370                 375

CGA TTC CGT CTT GGC TTC ATG GCC ACC TTC CCC TGC TGT CCC AAC CCA       1383
Arg Phe Arg Leu Gly Phe Met Ala Thr Phe Pro Cys Cys Pro Asn Pro
        380                 385                 390

GGT ACC CCT GGG GTG AGA GGA GAG ATG GGA GAG GAG GAA GGC AGG           1431
Gly Thr Pro Gly Val Arg Gly Glu Met Gly Glu Glu Glu Gly Arg
    395                 400                 405

ACC ACA GGG GCG TCT TTG TCC AGA TAC TCC TAC AGC CAC ATG AGC ACC       1479
Thr Thr Gly Ala Ser Leu Ser Arg Tyr Ser Tyr Ser His Met Ser Thr
410                 415                 420                 425

TCT GCT CCG CCC CCG TGAGCTGGGC CCGGGGCTAC ACAGTACAGC AGGAAGGAGG       1534
Ser Ala Pro Pro Pro
                430

CCACGGGAGG AGGAGGAGAA AAGAAAGGAA AGGAGAAAGC AGGAGAAGCA GGAGGAGGCA     1594

GAAGCAAAAG AGAAGGAAGG CCCAGGT                                         1621
```

-continued (2) INFORMATION FOR SEQ ID NO:23:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO:23:

```
Met Asp Val Val Asp Ser Leu Phe Val Asn Gly Ser Asn Ile Thr Ser
 1               5                  10                  15

Ala Cys Glu Leu Gly Phe Glu Asn Glu Thr Leu Phe Cys Leu Asp Arg
                20                  25                  30

Pro Arg Pro Ser Lys Glu Trp Gln Pro Ala Val Gln Ile Leu Leu Tyr
            35                  40                  45

Ser Leu Ile Phe Leu Leu Ser Val Leu Gly Asn Thr Leu Val Ile Thr
        50                  55                  60

Val Leu Ile Arg Asn Lys Arg Met Arg Thr Val Thr Asn Ile Phe Leu
65                  70                  75                  80

Leu Ser Leu Ala Val Ser Asp Leu Met Leu Cys Leu Phe Cys Met Pro
                85                  90                  95

Phe Asn Leu Ile Pro Ser Leu Leu Lys Asp Phe Ile Phe Gly Ser Ala
            100                 105                 110

Val Cys Lys Thr Thr Thr Tyr Phe Met Gly Thr Ser Val Ser Val Ser
        115                 120                 125

Thr Phe Asn Leu Val Ala Ile Ser Leu Glu Arg Tyr Gly Ala Ile Cys
    130                 135                 140

Lys Pro Leu Gln Ser Arg Val Trp Gln Thr Lys Ser His Ala Leu Lys
145                 150                 155                 160

Val Ile Ala Ala Thr Trp Cys Leu Ser Phe Thr Ile Met Thr Pro Tyr
                165                 170                 175

Pro Ile Tyr Ser Asn Leu Val Pro Phe Thr Lys Asn Asn Asn Gln Thr
            180                 185                 190

Gly Asn Met Cys Arg Phe Leu Leu Pro Asn Asp Val Met Gln Gln Thr
        195                 200                 205

Trp His Thr Phe Leu Leu Leu Ile Leu Phe Leu Ile Pro Gly Ile Val
    210                 215                 220

Met Met Val Ala Tyr Gly Leu Ile Ser Leu Glu Leu Tyr Gln Gly Ile
225                 230                 235                 240

Lys Phe Asp Ala Ile Gln Lys Lys Ser Ala Lys Glu Arg Lys Thr Ser
                245                 250                 255

Thr Gly Ser Ser Gly Pro Met Glu Asp Ser Asp Gly Cys Tyr Leu Gln
            260                 265                 270

Lys Ser Arg His Pro Arg Lys Leu Glu Leu Arg Gln Leu Ser Pro Ser
        275                 280                 285

Ser Ser Gly Ser Asn Arg Ile Asn Arg Ile Arg Ser Ser Ser Ser Thr
    290                 295                 300

Ala Asn Leu Met Ala Lys Lys Arg Val Ile Arg Met Leu Ile Val Ile
305                 310                 315                 320

Val Val Leu Phe Phe Leu Cys Trp Met Pro Ile Phe Ser Ala Asn Ala
                325                 330                 335

Trp Arg Ala Tyr Asp Thr Val Ser Ala Glu Arg His Leu Ser Gly Thr
            340                 345                 350

Pro Ile Ser Phe Ile Leu Leu Leu Ser Tyr Thr Ser Ser Cys Val Asn
        355                 360                 365
```

```
Pro Ile Ile Tyr Cys Phe Met Asn Lys Arg Phe Arg Leu Gly Phe Met
    370                 375                 380

Ala Thr Phe Pro Cys Cys Pro Asn Pro Gly Thr Pro Gly Val Arg Gly
385                 390                 395                 400

Glu Met Gly Glu Glu Glu Gly Arg Thr Thr Gly Ala Ser Leu Ser
                405                 410                 415

Arg Tyr Ser Tyr Ser His Met Ser Thr Ser Ala Pro Pro Pro
            420                 425                 430

(2) INFORMATION FOR SEQ ID NO:24:

(i) SEQUENCE CHARACTERISTICS:
        (A) LENGTH: 450 amino acids
        (B) TYPE: amino acid
        (D) TOPOLOGY: linear (vii) IMMEDIATE SOURCE:
        (B) CLONE: guinea pig CCKA receptor (xi) SEQUENCE DESCRIPTION: SEQ ID NO:24:

Met Ser Val Glu Arg Ala Val Cys Gln Pro Ala Ser Pro Trp Trp Glu
1               5                   10                  15

Ala Glu Ala Arg Met Asp Val Val Asp Ser Leu Phe Val Asn Gly Ser
                20                  25                  30

Asn Ile Thr Ser Ala Cys Glu Leu Gly Phe Glu Asn Glu Thr Leu Phe
            35                  40                  45

Cys Leu Asp Arg Pro Arg Pro Ser Lys Glu Trp Gln Pro Ala Val Gln
50                  55                  60

Ile Leu Leu Tyr Ser Leu Ile Phe Leu Leu Ser Val Leu Gly Asn Thr
65                  70                  75                  80

Leu Val Ile Thr Val Leu Ile Arg Asn Lys Arg Met Arg Thr Val Thr
                85                  90                  95

Asn Ile Phe Leu Leu Ser Leu Ala Val Ser Asp Leu Met Leu Cys Leu
                100                 105                 110

Phe Cys Met Pro Phe Asn Leu Ile Pro Ser Leu Leu Lys Asp Phe Ile
        115                 120                 125

Phe Gly Ser Ala Val Cys Lys Thr Thr Thr Tyr Phe Met Gly Thr Ser
        130                 135                 140

Val Ser Val Ser Thr Phe Asn Leu Val Ala Ile Ser Leu Glu Arg Tyr
145                 150                 155                 160

Gly Ala Ile Cys Lys Pro Leu Gln Ser Arg Val Trp Gln Thr Lys Ser
                165                 170                 175

His Ala Leu Lys Val Ile Ala Ala Thr Trp Cys Leu Ser Phe Thr Ile
            180                 185                 190

Met Thr Pro Tyr Pro Ile Tyr Ser Asn Leu Val Pro Phe Thr Lys Asn
                195                 200                 205

Asn Asn Gln Thr Gly Asn Met Cys Arg Phe Leu Leu Pro Asn Asp Val
    210                 215                 220

Met Gln Gln Thr Trp His Thr Phe Leu Leu Leu Ile Leu Phe Leu Ile
225                 230                 235                 240

Pro Gly Ile Val Met Met Val Ala Tyr Gly Leu Ile Ser Leu Glu Leu
                245                 250                 255

Tyr Gln Gly Ile Lys Phe Asp Ala Ile Gln Lys Lys Ser Ala Lys Glu
            260                 265                 270

Arg Lys Thr Ser Thr Gly Ser Ser Gly Pro Met Glu Asp Ser Asp Gly
        275                 280                 285
```

```
Cys Tyr Leu Gln Lys Ser Arg His Pro Arg Lys Leu Glu Leu Arg Gln
            290                 295                 300

Leu Ser Pro Ser Ser Gly Ser Asn Arg Ile Asn Arg Ile Arg Ser
305                 310                 315                 320

Ser Ser Ser Thr Ala Asn Leu Met Ala Lys Lys Arg Val Ile Arg Met
                325                 330                 335

Leu Ile Val Ile Val Val Leu Phe Phe Leu Cys Trp Met Pro Ile Phe
            340                 345                 350

Ser Ala Asn Ala Trp Arg Ala Tyr Asp Thr Val Ser Ala Glu Arg His
                355                 360                 365

Leu Ser Gly Thr Pro Ile Ser Phe Ile Leu Leu Ser Tyr Thr Ser
    370                 375                 380

Ser Cys Val Asn Pro Ile Ile Tyr Cys Phe Met Asn Lys Arg Phe Arg
385                 390                 395                 400

Leu Gly Phe Met Ala Thr Phe Pro Cys Cys Pro Asn Pro Gly Thr Pro
                405                 410                 415

Gly Val Arg Gly Glu Met Gly Glu Glu Glu Gly Arg Thr Thr Gly
            420                 425                 430

Ala Ser Leu Ser Arg Tyr Ser Tyr Ser His Met Ser Thr Ser Ala Pro
        435                 440                 445

Pro Pro
    450

(2) INFORMATION FOR SEQ ID NO:25:

(i) SEQUENCE CHARACTERISTICS:
        (A) LENGTH: 2015 base pairs
        (B) TYPE: nucleic acid
        (C) STRANDEDNESS: double
        (D) TOPOLOGY: linear (vii) IMMEDIATE SOURCE:
        (B) CLONE: guinea pig gallbladder and pancreas CCKB
            receptor (ix) FEATURE:
        (A) NAME/KEY: CDS
        (B) LOCATION: 13..1374

(xi) SEQUENCE DESCRIPTION: SEQ ID NO:25:

CTCGGAGGGG CC ATG GAG CTG CTC AAG CTG AAC CGG AGC CTC CAG GGA        48
              Met Glu Leu Leu Lys Leu Asn Arg Ser Leu Gln Gly
                1               5                   10

CCC GGG CCT GGG CCG GGG GCT CCC CTG TGC CGC CCG GCT GGC CCG CTT     96
Pro Gly Pro Gly Pro Gly Ala Pro Leu Cys Arg Pro Ala Gly Pro Leu
        15                  20                  25

CTC AAC AGC AGC GGT GCA GGC AAC GTC AGC TGC GAA ACC CCT CGC ATC    144
Leu Asn Ser Ser Gly Ala Gly Asn Val Ser Cys Glu Thr Pro Arg Ile
    30                  35                  40

CGA GGC GCC GGG ACG AGA GAA TTG GAG CTG GCC ATC AGA GTC ACC CTT    192
Arg Gly Ala Gly Thr Arg Glu Leu Glu Leu Ala Ile Arg Val Thr Leu
45                  50                  55                  60

TAC GCA GTG ATC TTT CTG ATG AGC GTT GGA GGA AAT GTG CTC ATC ATT    240
Tyr Ala Val Ile Phe Leu Met Ser Val Gly Gly Asn Val Leu Ile Ile
                65                  70                  75

GTG GTC CTG GGA CTG AGC CGC CGC CTG AGA ACT GTG ACC AAT GCT TTC    288
Val Val Leu Gly Leu Ser Arg Arg Leu Arg Thr Val Thr Asn Ala Phe
            80                  85                  90

CTG CTC TCC CTG GCA GTC AGT GAC CTC CTG CTG GCT GTG GCT TGC ATG    336
Leu Leu Ser Leu Ala Val Ser Asp Leu Leu Leu Ala Val Ala Cys Met
        95                  100                 105
```

```
CCC TTC ACA CTC CTG CCC AAT CTT ATG GGC ACA TTC ATC TTT GGC ACC         384
Pro Phe Thr Leu Leu Pro Asn Leu Met Gly Thr Phe Ile Phe Gly Thr
    110                 115                 120

GTC ATC TGC AAG GCT GTT TCC TAC CTC ATG GGG GTG TCT GTG AGC GTG         432
Val Ile Cys Lys Ala Val Ser Tyr Leu Met Gly Val Ser Val Ser Val
125                 130                 135                 140

TCC ACG CTC AGC CTT GTG GCC ATC GCC CTG GAG CGG TAC AGC GCC ATC         480
Ser Thr Leu Ser Leu Val Ala Ile Ala Leu Glu Arg Tyr Ser Ala Ile
                145                 150                 155

TGC CGA CCA CTG CAG GCT CGA GTG TGG CAG ACC CGC TCC CAC GCA GCT         528
Cys Arg Pro Leu Gln Ala Arg Val Trp Gln Thr Arg Ser His Ala Ala
        160                 165                 170

CGC GTG ATT TTA GCC ACT TGG CTG CTG TCC GGA TTG CTC ATG GTC CCC         576
Arg Val Ile Leu Ala Thr Trp Leu Leu Ser Gly Leu Leu Met Val Pro
            175                 180                 185

TAC CCT GTG TAC ACT GCT GTG CAG CCG GTA GGG CCT CGT GTG CTG CAG         624
Tyr Pro Val Tyr Thr Ala Val Gln Pro Val Gly Pro Arg Val Leu Gln
        190                 195                 200

TGC GTG CAT CGC TGG CCC AAC GCA CGG GTC CGC CAG ACC TGG TCA GTA         672
Cys Val His Arg Trp Pro Asn Ala Arg Val Arg Gln Thr Trp Ser Val
205                 210                 215                 220

CTG CTG CTC CTG CTC TTG TTC TTC GTC CCC GGA GTG GTT ATG GCA GTG         720
Leu Leu Leu Leu Leu Leu Phe Phe Val Pro Gly Val Val Met Ala Val
                225                 230                 235

GCC TAC GGG CTC ATC TCC CGC GAG CTC TAC TTA GGG CTT CGC TTT GAC         768
Ala Tyr Gly Leu Ile Ser Arg Glu Leu Tyr Leu Gly Leu Arg Phe Asp
            240                 245                 250

GGT GAC GCC GAC AGT GAG AGC CAG AGC AGG GTC CGA GGC CCG GGA GGT         816
Gly Asp Ala Asp Ser Glu Ser Gln Ser Arg Val Arg Gly Pro Gly Gly
        255                 260                 265

CTG TCC GGT TCC GCG CCA GGT CCT GCT CAC CAG AAT GGG CGT TGC CGG         864
Leu Ser Gly Ser Ala Pro Gly Pro Ala His Gln Asn Gly Arg Cys Arg
270                 275                 280

CCT GAA TCT GGC CTG TCA GGC GAG GAC AGC GAC GGC TGC TAT GTG CAA         912
Pro Glu Ser Gly Leu Ser Gly Glu Asp Ser Asp Gly Cys Tyr Val Gln
285                 290                 295                 300

CTG CCA CGG TCT CGG CCG GCC CTG GAG CTG TCG GCC CTG GCG GCG TCC         960
Leu Pro Arg Ser Arg Pro Ala Leu Glu Leu Ser Ala Leu Ala Ala Ser
                305                 310                 315

ACC CCT GCA CCA GGA CCT GGC CCC CGG CCC ACC CAG GCC AAG CTG CTG        1008
Thr Pro Ala Pro Gly Pro Gly Pro Arg Pro Thr Gln Ala Lys Leu Leu
            320                 325                 330

GCT AAG AAG CGC GTG GTG CGG ATG TTG CTG GTC ATC GTT GTG CTC TTT        1056
Ala Lys Lys Arg Val Val Arg Met Leu Leu Val Ile Val Val Leu Phe
        335                 340                 345

TTC CTG TGT TGG TTG CCG GTG TAC AGC GCC AAC ACG TGG CGT GCC TTC        1104
Phe Leu Cys Trp Leu Pro Val Tyr Ser Ala Asn Thr Trp Arg Ala Phe
350                 355                 360

GAC GGC CCG GGT GCG CAT CGG GCC CTC TCG GGA GCT CCC ATC TCT TTC        1152
Asp Gly Pro Gly Ala His Arg Ala Leu Ser Gly Ala Pro Ile Ser Phe
365                 370                 375                 380

ATC CAT TTG CTG AGC TAC GCC TCC GCC TGT GTC AAC CCA CTG GTC TAC        1200
Ile His Leu Leu Ser Tyr Ala Ser Ala Cys Val Asn Pro Leu Val Tyr
                385                 390                 395

TGC TTC ATG CAC CGT CCG TTT CGC CAG GCC TGC CTG GAC ACT TGC GCC        1248
Cys Phe Met His Arg Pro Phe Arg Gln Ala Cys Leu Asp Thr Cys Ala
            400                 405                 410

CGC TGC TGC CCT AGG CCT CCT CGA GCT CGT CCC AGG CCT CTC CCA GAG        1296
Arg Cys Cys Pro Arg Pro Pro Arg Ala Arg Pro Arg Pro Leu Pro Glu
        415                 420                 425
```

```
GAG GAC CCT CCC ACC CCC TCC ATT CGT TCG CTG TCC AGG CTG AGC TAC      1344
Glu Asp Pro Pro Thr Pro Ser Ile Arg Ser Leu Ser Arg Leu Ser Tyr
    430                 435                 440

ACC ACC ATC AGC ACG CTG GGG CCC GGC TGATGGGGGT GGTGGGGGCG             1391
Thr Thr Ile Ser Thr Leu Gly Pro Gly
445                 450

CTGAGGCAGC ACAGGCATCC TGTAAGCACA AATACATCCA GACACACAAG AAACACAAAC     1451

CACACTTGAC AGAGAGACTA ACACTCAACA GCATCGACTA ACCCAACACT CAGGAAACGG     1511

TGGCATAGTA CACACACACA CACACACACC AGAGCTTTAC ACAGAAAGGA GGCTCCCTGA     1571

GGGCCTTCCT AGAGACAGGG CACTGATCTT GACAGGCAAA CATAGCATCC TTAGCAGCAT     1631

CCTTATGCAC TGGGAACTCT GACAGCTGAC CGGTCCTCAT GCCCACATGC ATTAATCACA     1691

CTGATTCTCT AAGGGCAGCA GACCGTGGCA CAGGACTGAT TTGGGTTATT CCAGGCTGTC     1751

TTTAGTTTGA CATCACAAGA CACTTCTCCC CACCAGCACT GCCCCTACAA CAGGCCTGAT     1811

ACCTTCCTGA CCAACAGGCT CTTTAGGACT AAAAACTCTC TCTTCGTCCC TTTCCAGTTA     1871

AGGACTGCAG CCCTGCCCCC TCATCTTCAC CAGACCTCTT CAAAACACAA TAAATGACTT     1931

GCTCTCAAAA AAAAAAAAAA AAAAAAAGC GGNNGCAGAA TTCGAGCTCG GTACCCGGGG     1991

ATCCTCTAGA GTCGACCTGC AGGC                                           2015
```

(2) INFORMATION FOR SEQ ID NO:26:

(i) SEQUENCE CHARACTERISTICS:
        (A) LENGTH: 453 amino acids
        (B) TYPE: amino acid
        (D) TOPOLOGY: linear (ii) MOLECULE TYPE: protein (xi) SEQUENCE DESCRIPTION: SEQ ID NO:26:

```
Met Glu Leu Leu Lys Leu Asn Arg Ser Leu Gln Gly Pro Gly Pro Gly
1               5                   10                  15

Pro Gly Ala Pro Leu Cys Arg Pro Ala Gly Pro Leu Leu Asn Ser Ser
                20                  25                  30

Gly Ala Gly Asn Val Ser Cys Glu Thr Pro Arg Ile Arg Gly Ala Gly
            35                  40                  45

Thr Arg Glu Leu Glu Leu Ala Ile Arg Val Thr Leu Tyr Ala Val Ile
        50                  55                  60

Phe Leu Met Ser Val Gly Gly Asn Val Leu Ile Ile Val Val Leu Gly
65                  70                  75                  80

Leu Ser Arg Arg Leu Arg Thr Val Thr Asn Ala Phe Leu Leu Ser Leu
                85                  90                  95

Ala Val Ser Asp Leu Leu Leu Ala Val Ala Cys Met Pro Phe Thr Leu
                100                 105                 110

Leu Pro Asn Leu Met Gly Thr Phe Ile Phe Gly Thr Val Ile Cys Lys
                115                 120                 125

Ala Val Ser Tyr Leu Met Gly Val Ser Val Ser Val Ser Thr Leu Ser
            130                 135                 140

Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Leu
                165                 170                 175

Ala Thr Trp Leu Leu Ser Gly Leu Leu Met Val Pro Tyr Pro Val Tyr
                180                 185                 190
```

```
Thr Ala Val Gln Pro Val Gly Pro Arg Val Leu Gln Cys Val His Arg
        195                 200                 205

Trp Pro Asn Ala Arg Val Arg Gln Thr Trp Ser Val Leu Leu Leu Leu
        210                 215                 220

Leu Leu Phe Phe Val Pro Gly Val Val Met Ala Val Ala Tyr Gly Leu
225                 230                 235                 240

Ile Ser Arg Glu Leu Tyr Leu Gly Leu Arg Phe Asp Gly Asp Ala Asp
                245                 250                 255

Ser Glu Ser Gln Ser Arg Val Arg Gly Pro Gly Gly Leu Ser Gly Ser
            260                 265                 270

Ala Pro Gly Pro Ala His Gln Asn Gly Arg Cys Arg Pro Glu Ser Gly
        275                 280                 285

Leu Ser Gly Glu Asp Ser Asp Gly Cys Tyr Val Gln Leu Pro Arg Ser
    290                 295                 300

Arg Pro Ala Leu Glu Leu Ser Ala Leu Ala Ala Ser Thr Pro Ala Pro
305                 310                 315                 320

Gly Pro Gly Pro Arg Pro Thr Gln Ala Lys Leu Leu Ala Lys Lys Arg
                325                 330                 335

Val Val Arg Met Leu Leu Val Ile Val Val Leu Phe Phe Leu Cys Trp
                340                 345                 350

Leu Pro Val Tyr Ser Ala Asn Thr Trp Arg Ala Phe Asp Gly Pro Gly
            355                 360                 365

Ala His Arg Ala Leu Ser Gly Ala Pro Ile Ser Phe Ile His Leu Leu
        370                 375                 380

Ser Tyr Ala Ser Ala Cys Val Asn Pro Leu Val Tyr Cys Phe Met His
385                 390                 395                 400

Arg Pro Phe Arg Gln Ala Cys Leu Asp Thr Cys Ala Arg Cys Cys Pro
                405                 410                 415

Arg Pro Pro Arg Ala Arg Pro Arg Pro Leu Pro Glu Glu Asp Pro Pro
            420                 425                 430

Thr Pro Ser Ile Arg Ser Leu Ser Arg Leu Ser Tyr Thr Thr Ile Ser
        435                 440                 445

Thr Leu Gly Pro Gly
450

(2) INFORMATION FOR SEQ ID NO:27:

(i) SEQUENCE CHARACTERISTICS:
        (A) LENGTH: 453 amino acids
        (B) TYPE: amino acid
        (D) TOPOLOGY: linear (vii) IMMEDIATE SOURCE:
        (B) CLONE: canine gastrin receptor (xi) SEQUENCE DESCRIPTION: SEQ ID NO:27:

Met Glu Leu Leu Lys Leu Asn Arg Ser Ala Gln Gly Ser Gly Ala Gly
1               5                   10                  15

Pro Gly Ala Ser Leu Cys Arg Ala Gly Gly Ala Leu Leu Asn Ser Ser
            20                  25                  30

Gly Ala Gly Asn Leu Ser Cys Glu Pro Pro Arg Leu Arg Gly Ala Gly
        35                  40                  45

Thr Arg Glu Leu Glu Leu Ala Ile Arg Val Thr Leu Tyr Ala Val Ile
    50                  55                  60

Phe Leu Met Ser Val Gly Gly Asn Val Leu Ile Ile Val Val Leu Gly
65                  70                  75                  80
```

-continued

```
Leu Ser Arg Arg Leu Arg Thr Val Thr Asn Ala Phe Leu Leu Ser Leu
                85                  90                  95

Ala Val Ser Asp Leu Leu Ala Val Ala Cys Met Pro Phe Thr Leu
            100                 105                 110

Leu Pro Asn Leu Met Gly Thr Phe Ile Phe Gly Thr Val Val Cys Lys
        115                 120                 125

Ala Val Ser Tyr Leu Met Gly Val Ser Val Ser Thr Leu Ser
    130                 135                 140

Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Ile
                165                 170                 175

Ala Thr Trp Met Leu Ser Gly Leu Leu Met Val Pro Tyr Pro Val Tyr
            180                 185                 190

Thr Ala Val Gln Pro Ala Gly Gly Ala Arg Ala Leu Gln Cys Val His
        195                 200                 205

Arg Trp Pro Ser Ala Arg Val Arg Gln Thr Trp Ser Val Leu Leu Leu
    210                 215                 220

Leu Leu Leu Phe Phe Val Pro Gly Val Val Met Ala Val Ala Tyr Gly
225                 230                 235                 240

Leu Ile Ser Arg Glu Leu Tyr Leu Gly Leu Arg Phe Asp Glu Asp Ser
                245                 250                 255

Asp Ser Glu Ser Arg Val Arg Ser Gln Gly Gly Leu Arg Gly Gly Ala
            260                 265                 270

Gly Pro Gly Pro Ala Pro Pro Asn Gly Ser Cys Arg Pro Glu Gly Gly
        275                 280                 285

Leu Ala Gly Glu Asp Gly Asp Gly Cys Tyr Val Gln Leu Pro Arg Ser
    290                 295                 300

Arg Gln Thr Leu Glu Leu Ser Ala Leu Thr Ala Pro Thr Pro Gly Pro
305                 310                 315                 320

Gly Gly Gly Pro Arg Pro Tyr Gln Ala Lys Leu Leu Ala Lys Lys Arg
                325                 330                 335

Val Val Arg Met Leu Leu Val Ile Val Val Leu Phe Phe Leu Cys Trp
            340                 345                 350

Leu Pro Leu Tyr Ser Ala Asn Thr Trp Arg Ala Phe Asp Ser Ser Gly
        355                 360                 365

Ala His Arg Ala Leu Ser Gly Ala Pro Ile Ser Phe Ile His Leu Leu
    370                 375                 380

Ser Tyr Ala Ser Ala Cys Val Asn Pro Leu Val Tyr Cys Phe Met His
385                 390                 395                 400

Arg Arg Phe Arg Gln Ala Cys Leu Glu Thr Cys Ala Arg Cys Cys Pro
                405                 410                 415

Arg Pro Pro Arg Ala Arg Pro Arg Pro Leu Pro Asp Glu Asp Pro Pro
            420                 425                 430

Thr Pro Ser Ile Ala Ser Leu Ser Arg Leu Ser Tyr Thr Thr Ile Ser
        435                 440                 445

Thr Leu Gly Pro Gly
    450
```

(2) INFORMATION FOR SEQ ID NO:28:

(i) SEQUENCE CHARACTERISTICS:
        (A) LENGTH: 1969 base pairs
        (B) TYPE: nucleic acid (C) STRANDEDNESS: double
            (D) TOPOLOGY: linear (ii) MOLECULE TYPE: cDNA (vii) IMMEDIATE SOURCE:
            (B) CLONE: human CCKB receptor (ix) FEATURE:
            (A) NAME/KEY: CDS
            (B) LOCATION: 1..1344

(xi) SEQUENCE DESCRIPTION: SEQ ID NO:28:

```
ATG GAG CTG CTC AAG CTG AAC CGG AAC GTG CAG GGA ACC GGA CCC GGG       48
Met Glu Leu Leu Lys Leu Asn Arg Asn Val Gln Gly Thr Gly Pro Gly
 1               5                  10                  15

CCG GGG GCT TCC CTG TGC CGC CCG GGG GCG CCT CTC CTC AAC AGC AGC       96
Pro Gly Ala Ser Leu Cys Arg Pro Gly Ala Pro Leu Leu Asn Ser Ser
                20                  25                  30

AGT GTG GGC AAC CTC AGC TGC GAG CCC CCT CGC ATT CGC GGA GCC GGG      144
Ser Val Gly Asn Leu Ser Cys Glu Pro Pro Arg Ile Arg Gly Ala Gly
            35                  40                  45

ACA CGA GAA TTG GAG CTG GCC ATT AGA ATC ACT CTT TAC GCA GTG ATC      192
Thr Arg Glu Leu Glu Leu Ala Ile Arg Ile Thr Leu Tyr Ala Val Ile
 50                  55                  60

TTC CTG ATG AGC GTT GGA GGA AAT ATG CTC ATC ATC GTG GTC CTG GGA      240
Phe Leu Met Ser Val Gly Gly Asn Met Leu Ile Ile Val Val Leu Gly
 65                  70                  75                  80

CTG AGC CGC CGC CTG AGG ACT GTC ACC AAT GCC TTC CTC CTC TCA CTG      288
Leu Ser Arg Arg Leu Arg Thr Val Thr Asn Ala Phe Leu Leu Ser Leu
                85                  90                  95

GCA GTC AGC GAC CTC CTG CTG GCT GTG GCT TGC ATG CCC TTC ACC CTC      336
Ala Val Ser Asp Leu Leu Leu Ala Val Ala Cys Met Pro Phe Thr Leu
            100                 105                 110

CTG CCC AAT CTC ATG GGC ACA TTC ATC TTT GGC ACC GTC ATC TGC AAG      384
Leu Pro Asn Leu Met Gly Thr Phe Ile Phe Gly Thr Val Ile Cys Lys
        115                 120                 125

GCG GTT TCC TAC CTC ATG GGG GTG TCT GTG AGT GTG TCC ACG CTA AGC      432
Ala Val Ser Tyr Leu Met Gly Val Ser Val Ser Val Ser Thr Leu Ser
    130                 135                 140

CTC GTG GCC ATC GCA CTG GAG CGG TAC AGC GCC ATC TGC CGA CCA CTG      480
Leu Val Ala Ile Ala Leu Glu Arg Tyr Ser Ala Ile Cys Arg Pro Leu
145                 150                 155                 160

CAG GCA CGA GTG TGG CAG ACG CGC TCC CAC GCG GCT CGC GTG ATT GTA      528
Gln Ala Arg Val Trp Gln Thr Arg Ser His Ala Ala Arg Val Ile Val
                165                 170                 175

GCC ACG TGG CTG CTG TCC GGA CTA CTC ATG GTG CCC TAC CCC GTG TAC      576
Ala Thr Trp Leu Leu Ser Gly Leu Leu Met Val Pro Tyr Pro Val Tyr
            180                 185                 190

ACT GTC GTG CAA CCA GTG GGG CCT CGT GTG CTG CAG TGC GTG CAT CGC      624
Thr Val Val Gln Pro Val Gly Pro Arg Val Leu Gln Cys Val His Arg
        195                 200                 205

TGG CCC AGT GCG CGG GTC CGC CAG ACC TGG TCC GTA CTG CTG CTT CTG      672
Trp Pro Ser Ala Arg Val Arg Gln Thr Trp Ser Val Leu Leu Leu Leu
    210                 215                 220

CTC TTG TTC TTC ATC CCG AGT GTG GTT ATG GCC GTG GCC TAC GGG CTT      720
Leu Leu Phe Phe Ile Pro Ser Val Val Met Ala Val Ala Tyr Gly Leu
225                 230                 235                 240

ATC TCT CGC GAG CTC TAC TTA GGG CTT CGC TTT GAC GGC GAC AGT GAC      768
Ile Ser Arg Glu Leu Tyr Leu Gly Leu Arg Phe Asp Gly Asp Ser Asp
                245                 250                 255
```

```
AGC GAC AGC CAA AGC AGG GTC CGA AAC CAA GGC GGG CTG CCA GGG GCT      816
Ser Asp Ser Gln Ser Arg Val Arg Asn Gln Gly Gly Leu Pro Gly Ala
            260                 265                 270

GTT CAC CAG AAC GGG CGT TGC CGG CCT GAG ACT GGC GCG GTT GGC GAA      864
Val His Gln Asn Gly Arg Cys Arg Pro Glu Thr Gly Ala Val Gly Glu
            275                 280                 285

GAC AGC GAT GGC TGC TAC GTG CAA CTT CCA CGT TCC CGG CCT GCC CTG      912
Asp Ser Asp Gly Cys Tyr Val Gln Leu Pro Arg Ser Arg Pro Ala Leu
            290                 295                 300

GAG CTG ACG GCG CTG ACG GCT CCA GGG CCG GGA TCC GGC TCC CGG CCC      960
Glu Leu Thr Ala Leu Thr Ala Pro Gly Pro Gly Ser Gly Ser Arg Pro
305                 310                 315                 320

ACC CAG GCC AAG CTG CTG GCT AAG AAG CGC GTG GTG CGA ATG TTG CTG     1008
Thr Gln Ala Lys Leu Leu Ala Lys Lys Arg Val Val Arg Met Leu Leu
                325                 330                 335

GTG ATC GTT GTG CTT TTT TTT CTG TGT TGG TTG CCA GTT TAT AGT GCC     1056
Val Ile Val Val Leu Phe Phe Leu Cys Trp Leu Pro Val Tyr Ser Ala
            340                 345                 350

AAC ACG TGG CGC GCC TTT GAT GGC CCG GGT GCA CAC GCA CTC TCG         1104
Asn Thr Trp Arg Ala Phe Asp Gly Pro Gly Ala His Arg Ala Leu Ser
            355                 360                 365

GGT GCT CCT ATC TCC TTC ATT CAC TTG CTG AGC TAC GCC TCG GCC TGT     1152
Gly Ala Pro Ile Ser Phe Ile His Leu Leu Ser Tyr Ala Ser Ala Cys
370                 375                 380

GTC AAC CCC CTG GTC TAC TGC TTC ATG CAC CGT CGC TTT CGC CAG GCC     1200
Val Asn Pro Leu Val Tyr Cys Phe Met His Arg Arg Phe Arg Gln Ala
385                 390                 395                 400

TGC CTG GAA ACT TGC GCT CGC TGC TGC CCC CGG CCT CCA CGA GCT CGC     1248
Cys Leu Glu Thr Cys Ala Arg Cys Cys Pro Arg Pro Pro Arg Ala Arg
                405                 410                 415

CCC AGG GCT CTT CCC GAT GAG GAC CCT CCC ACT CCC TCC ATT GCT TCG     1296
Pro Arg Ala Leu Pro Asp Glu Asp Pro Pro Thr Pro Ser Ile Ala Ser
            420                 425                 430

CTG TCC AGG CTT AGC TAC ACC ACC ATC AGC ACA CTG GGC CCT GGC TGAGGAGT1351
Leu Ser Arg Leu Ser Tyr Thr Thr Ile Ser Thr Leu Gly Pro Gly
            435                 440                 445

AGGGGCCGTG GGGGTTGAGG CAGGGCAAAT GACATGCACT GACCCTTCCA GACATAGAAA   1411

ACACAAACCA CAACTGACAC AGGAAACCAA CACCCAAAGC ATGGACTAAC CCCAACGACA   1471

GGAAAAGGTA GCTTACCTGA CACAAGAGGA ATAAGAATGG AGCAGTACAT GGGAAAGGAG   1531

GCATGCCTCT GATATGGGAC TGAGCCTGGC CCATAGAAAC ATGACACTGA CCTTGGAGAG   1591

ACACAGCGTC CCTAGCAGTG AACTATTTCT ACACAGTGGG AACTCTGACA AGGGCTGACC   1651

TGCCTCTCAC ACACATAGAT TAATGGCACT GATTGTTTTA GAGACTATGG AGCCTGGCAC   1711

AGGACTGACT CTGGGATGCT CCTAGTTTGA CCTCACAGTG ACCCTTCCCA ATCAGCACTG   1771

AAAATACCAT CAGGCCTAAT CTCATACCTC TGACCAACAG GCTGTTCTGC ACTGAAAAGG   1831

TTCTTCATCC CTTTCCAGTT AAGGACCGTG GCCCTGCCCT CTCCTTCCTT CCCAAACTGT   1891

TCAAGAAATA ATAAATTGTT TGGCTTCCTC CTGAAAAAAA AAAAAAAAAA AAAAAAAAA    1951

AAAAAAAAAA GGAATTCC                                                 1969

(2) INFORMATION FOR SEQ ID NO:29:

(i) SEQUENCE CHARACTERISTICS:
            (A) LENGTH: 447 amino acids
            (B) TYPE: amino acid
            (D) TOPOLOGY: linear (ii) MOLECULE TYPE: protein
```

-continued (xi) SEQUENCE DESCRIPTION: SEQ ID NO:29:

```
Met Glu Leu Leu Lys Leu Asn Arg Asn Val Gln Gly Thr Gly Pro Gly
 1               5                  10                  15

Pro Gly Ala Ser Leu Cys Arg Pro Gly Ala Pro Leu Leu Asn Ser Ser
             20                  25                  30

Ser Val Gly Asn Leu Ser Cys Glu Pro Pro Arg Ile Arg Gly Ala Gly
         35                  40                  45

Thr Arg Glu Leu Glu Leu Ala Ile Arg Ile Thr Leu Tyr Ala Val Ile
     50                  55                  60

Phe Leu Met Ser Val Gly Asn Met Leu Ile Ile Val Val Leu Gly
 65                  70                  75                  80

Leu Ser Arg Arg Leu Arg Thr Val Thr Asn Ala Phe Leu Leu Ser Leu
                 85                  90                  95

Ala Val Ser Asp Leu Leu Leu Ala Val Ala Cys Met Pro Phe Thr Leu
            100                 105                 110

Leu Pro Asn Leu Met Gly Thr Phe Ile Phe Gly Thr Val Ile Cys Lys
            115                 120                 125

Ala Val Ser Tyr Leu Met Gly Val Ser Val Ser Val Ser Thr Leu Ser
        130                 135                 140

Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Val
                165                 170                 175

Ala Thr Trp Leu Leu Ser Gly Leu Leu Met Val Pro Tyr Pro Val Tyr
            180                 185                 190

Thr Val Val Gln Pro Val Gly Pro Arg Val Leu Gln Cys Val His Arg
        195                 200                 205

Trp Pro Ser Ala Arg Val Arg Gln Thr Trp Ser Val Leu Leu Leu Leu
    210                 215                 220

Leu Leu Phe Phe Ile Pro Ser Val Val Met Ala Val Ala Tyr Gly Leu
225                 230                 235                 240

Ile Ser Arg Glu Leu Tyr Leu Gly Leu Arg Phe Asp Gly Asp Ser Asp
                245                 250                 255

Ser Asp Ser Gln Ser Arg Val Arg Asn Gln Gly Gly Leu Pro Gly Ala
            260                 265                 270

Val His Gln Asn Gly Arg Cys Arg Pro Glu Thr Gly Ala Val Gly Glu
        275                 280                 285

Asp Ser Asp Gly Cys Tyr Val Gln Leu Pro Arg Ser Arg Pro Ala Leu
    290                 295                 300

Glu Leu Thr Ala Leu Thr Ala Pro Gly Pro Gly Ser Gly Ser Arg Pro
305                 310                 315                 320

Thr Gln Ala Lys Leu Leu Ala Lys Lys Arg Val Val Arg Met Leu Leu
                325                 330                 335

Val Ile Val Leu Phe Phe Leu Cys Trp Leu Pro Val Tyr Ser Ala
            340                 345                 350

Asn Thr Trp Arg Ala Phe Asp Gly Pro Gly Ala His Arg Ala Leu Ser
        355                 360                 365

Gly Ala Pro Ile Ser Phe Ile His Leu Leu Ser Tyr Ala Ser Ala Cys
    370                 375                 380

Val Asn Pro Leu Val Tyr Cys Phe Met His Arg Arg Phe Arg Gln Ala
385                 390                 395                 400

Cys Leu Glu Thr Cys Ala Arg Cys Cys Pro Arg Pro Arg Ala Arg
                405                 410                 415
```

```
Pro Arg Ala Leu Pro Asp Glu Asp Pro Pro Thr Pro Ser Ile Ala Ser
            420                 425                 430
Leu Ser Arg Leu Ser Tyr Thr Thr Ile Ser Thr Leu Gly Pro Gly
        435                 440                 445
```

(2) INFORMATION FOR SEQ ID NO:30:

(i) SEQUENCE CHARACTERISTICS:
        (A) LENGTH: 1686 base pairs
        (B) TYPE: nucleic acid
        (C) STRANDEDNESS: double
        (D) TOPOLOGY: linear (vii) IMMEDIATE SOURCE:
        (B) CLONE: Human CCKAR (ix) FEATURE:
        (A) NAME/KEY: CDS
        (B) LOCATION: 154..1440

(xi) SEQUENCE DESCRIPTION: SEQ ID NO:30:

```
GGAATGGCTG AAAAAGCCCA CACCTGGAAA TCACTCCCTC CCTGCTCCTC CACGGCAGGT      60

TGCATCTGCG AGACGCTTCG GTCATTAGAG GAATGAGCCG GGAGTGAGCA ATTCACCAGC     120

TCTCCAGCAC TTGGTGGAAA GCAGCAGGCA AGG ATG GAT GTG GTT GAC AGC CTT     174
                                    Met Asp Val Val Asp Ser Leu
                                      1               5

CTT GTG AAT GGA AGC AAC ATC ACT CCT CCC TGT GAA CTC GGG CTC GAA       222
Leu Val Asn Gly Ser Asn Ile Thr Pro Pro Cys Glu Leu Gly Leu Glu
         10                  15                  20

AAT GAG ACG CTT TTC TGC TTG GAT CAG CCC CGT CCT TCC AAA GAG TGG      270
Asn Glu Thr Leu Phe Cys Leu Asp Gln Pro Arg Pro Ser Lys Glu Trp
     25                  30                  35

CAG CCA GCG GTG CAG ATT CTC TTG TAC TCC TTG ATA TTC CTG CTC AGC      318
Gln Pro Ala Val Gln Ile Leu Leu Tyr Ser Leu Ile Phe Leu Leu Ser
 40                  45                  50                  55

GTG CTG GGA AAC ACG CTG GTC ATC ACC GTG CTG ATT CGG AAC AAG CGG      366
Val Leu Gly Asn Thr Leu Val Ile Thr Val Leu Ile Arg Asn Lys Arg
             60                  65                  70

ATG CGG ACG GTC ACC AAC ATC TTC CTC CTC TCC CTG GCT GTC AGC GAC      414
Met Arg Thr Val Thr Asn Ile Phe Leu Leu Ser Leu Ala Val Ser Asp
         75                  80                  85

CTC ATG CTC TGT CTC TTC TGC ATG CCG TTC AAC CTC ATC CCC AAT CTG      462
Leu Met Leu Cys Leu Phe Cys Met Pro Phe Asn Leu Ile Pro Asn Leu
         90                  95                 100

CTC AAG GAT TTC ATC TTC GGG AGC GCC GTT TGC AAG ACC ACC ACC TAC      510
Leu Lys Asp Phe Ile Phe Gly Ser Ala Val Cys Lys Thr Thr Thr Tyr
    105                 110                 115

TTC ATG GGC ACC TCT GTG AGT GTA TCT ACC TTT AAT CTG GTA GCC ATA      558
Phe Met Gly Thr Ser Val Ser Val Ser Thr Phe Asn Leu Val Ala Ile
120                 125                 130                 135

TCT CTA GAG AGA TAT GGT GCG ATT TGC AAA CCC TTA CAG TCC CGG GTC      606
Ser Leu Glu Arg Tyr Gly Ala Ile Cys Lys Pro Leu Gln Ser Arg Val
                140                 145                 150

TGG CAG ACA AAA TCC CAT GCT TTG AAG GTG ATT GCT GCT ACC TGG TGC      654
Trp Gln Thr Lys Ser His Ala Leu Lys Val Ile Ala Ala Thr Trp Cys
            155                 160                 165

CTT TCC TTT ACC ATC ATG ACT CCG TAC CCC ATT TAT AGC AAC TTG GTG      702
Leu Ser Phe Thr Ile Met Thr Pro Tyr Pro Ile Tyr Ser Asn Leu Val
        170                 175                 180

CCT TTT ACC AAA AAT AAC AAC CAG ACC GCG AAT ATG TGC CGC TTT CTA      750
Pro Phe Thr Lys Asn Asn Asn Gln Thr Ala Asn Met Cys Arg Phe Leu
    185                 190                 195
```

-continued

```
CTG CCA AAT GAT GTT ATG CAG CAG TCC TGG CAC ACA TTC CTG TTA CTC      798
Leu Pro Asn Asp Val Met Gln Gln Ser Trp His Thr Phe Leu Leu Leu
200             205                 210                 215

ATC CTC TTT CTT ATT CCT GGA ATT GTG ATG ATG GTG GCA TAT GGA TTA      846
Ile Leu Phe Leu Ile Pro Gly Ile Val Met Met Val Ala Tyr Gly Leu
                220                 225                 230

ATC TCT TTG GAA CTC TAC CAG GGA ATA AAA TTT GAG GCT AGC CAG AAG      894
Ile Ser Leu Glu Leu Tyr Gln Gly Ile Lys Phe Glu Ala Ser Gln Lys
        235                 240                 245

AAG TCT GCT AAA GAA AGG AAA CCT AGC ACC ACC AGC AGC GGC AAA TAT      942
Lys Ser Ala Lys Glu Arg Lys Pro Ser Thr Thr Ser Ser Gly Lys Tyr
            250                 255                 260

GAG GAC AGC GAT GGG TGT TAC CTG CAA AAG ACC AGG CCC CCG AGG AAG      990
Glu Asp Ser Asp Gly Cys Tyr Leu Gln Lys Thr Arg Pro Pro Arg Lys
265                 270                 275

CTG GAG CTC CGG CAG CTG TCC ACC GGC AGC AGC AGC AGG GCC AAC CGC     1038
Leu Glu Leu Arg Gln Leu Ser Thr Gly Ser Ser Ser Arg Ala Asn Arg
280                 285                 290                 295

ATC CGG AGT AAC AGC TCC GCA GCC AAC CTG ATG GCC AAG AAA AGG GTG     1086
Ile Arg Ser Asn Ser Ser Ala Ala Asn Leu Met Ala Lys Lys Arg Val
                300                 305                 310

ATC CGC ATG CTC ATC GTC ATC GTG GTC CTC TTC TTC CTG TGC TGG ATG     1134
Ile Arg Met Leu Ile Val Ile Val Val Leu Phe Phe Leu Cys Trp Met
            315                 320                 325

CCC ATC TTC AGC GCC AAC GCC TGG CGG GCC TAC GAC ACC GCC TCC GCA     1182
Pro Ile Phe Ser Ala Asn Ala Trp Arg Ala Tyr Asp Thr Ala Ser Ala
            330                 335                 340

GAG CGC CGC CTC TCA GGA ACC CCC ATT TCC TTC ATC CTC CTC CTG TCC     1230
Glu Arg Arg Leu Ser Gly Thr Pro Ile Ser Phe Ile Leu Leu Leu Ser
345                 350                 355

TAC ACC TCC TCC TGC GTC AAC CCC ATC ATC TAC TGC TTC ATG AAC AAA     1278
Tyr Thr Ser Ser Cys Val Asn Pro Ile Ile Tyr Cys Phe Met Asn Lys
360                 365                 370                 375

CGC TTC CGC CTC GGC TTC ATG GCC ACC TTC CCC TGC TGC CCC AAT CCT     1326
Arg Phe Arg Leu Gly Phe Met Ala Thr Phe Pro Cys Cys Pro Asn Pro
                380                 385                 390

GGT CCC CCA GGG GCG AGG GGA GAG GTG GGG GAG GAG GAG GAA GGC GGG     1374
Gly Pro Pro Gly Ala Arg Gly Glu Val Gly Glu Glu Glu Glu Gly Gly
            395                 400                 405

ACC ACA GGA GCC TCT CTG TCC AGG TTC TCG TAC AGC CAT ATG AGT GCC     1422
Thr Thr Gly Ala Ser Leu Ser Arg Phe Ser Tyr Ser His Met Ser Ala
410                 415                 420

TCG GTG CCA CCC CAG TGAGATGTCC CCTGACCCTC CACCGCAGAA GGAAGGCAGG    1477
Ser Val Pro Pro Gln
    425

GAGGAGGCAG AGAAGAAAGA ACGGAAGAAG AGATCAGGAA GAGAAGGAGC AGAGCAGAGC  1537

TGATGGAGAA GGAAGGCTCC ATCTCCAGTG GGAACTCTTC AAGGTCTCTT TTCATCCTTC  1597

ATCTGATTCC AGAGCACTGC TCCAGTGGGG CCATGATTGG TTTCTAGGCA GTTCAAAGCA  1657

GGATATGTTA AGTAACACTC AACCATCAG                                   1686

(2) INFORMATION FOR SEQ ID NO:31:

(i) SEQUENCE CHARACTERISTICS:
        (A) LENGTH: 428 amino acids
        (B) TYPE: amino acid
        (D) TOPOLOGY: linear (ii) MOLECULE TYPE: protein
```

(xi) SEQUENCE DESCRIPTION: SEQ ID NO:31:

```
Met Asp Val Val Asp Ser Leu Leu Val Asn Gly Ser Asn Ile Thr Pro
  1               5                  10                  15

Pro Cys Glu Leu Gly Leu Glu Asn Glu Thr Leu Phe Cys Leu Asp Gln
             20                  25                  30

Pro Arg Pro Ser Lys Glu Trp Gln Pro Ala Val Gln Ile Leu Leu Tyr
         35                  40                  45

Ser Leu Ile Phe Leu Leu Ser Val Leu Gly Asn Thr Leu Val Ile Thr
     50                  55                  60

Val Leu Ile Arg Asn Lys Arg Met Arg Thr Val Thr Asn Ile Phe Leu
 65                  70                  75                  80

Leu Ser Leu Ala Val Ser Asp Leu Met Leu Cys Leu Phe Cys Met Pro
                 85                  90                  95

Phe Asn Leu Ile Pro Asn Leu Leu Lys Asp Phe Ile Phe Gly Ser Ala
                100                 105                 110

Val Cys Lys Thr Thr Thr Tyr Phe Met Gly Thr Ser Val Ser Val Ser
             115                 120                 125

Thr Phe Asn Leu Val Ala Ile Ser Leu Glu Arg Tyr Gly Ala Ile Cys
    130                 135                 140

Lys Pro Leu Gln Ser Arg Val Trp Gln Thr Lys Ser His Ala Leu Lys
145                 150                 155                 160

Val Ile Ala Ala Thr Trp Cys Leu Ser Phe Thr Ile Met Thr Pro Tyr
                165                 170                 175

Pro Ile Tyr Ser Asn Leu Val Pro Phe Thr Lys Asn Asn Gln Thr
                180                 185                 190

Ala Asn Met Cys Arg Phe Leu Leu Pro Asn Asp Val Met Gln Gln Ser
                195                 200                 205

Trp His Thr Phe Leu Leu Leu Ile Leu Phe Leu Ile Pro Gly Ile Val
        210                 215                 220

Met Met Val Ala Tyr Gly Leu Ile Ser Leu Glu Leu Tyr Gln Gly Ile
225                 230                 235                 240

Lys Phe Glu Ala Ser Gln Lys Lys Ser Ala Lys Glu Arg Lys Pro Ser
                245                 250                 255

Thr Thr Ser Ser Gly Lys Tyr Glu Asp Ser Asp Gly Cys Tyr Leu Gln
                260                 265                 270

Lys Thr Arg Pro Pro Arg Lys Leu Glu Leu Arg Gln Leu Ser Thr Gly
            275                 280                 285

Ser Ser Ser Arg Ala Asn Arg Ile Arg Ser Asn Ser Ser Ala Ala Asn
    290                 295                 300

Leu Met Ala Lys Lys Arg Val Ile Arg Met Leu Ile Val Ile Val Val
305                 310                 315                 320

Leu Phe Phe Leu Cys Trp Met Pro Ile Phe Ser Ala Asn Ala Trp Arg
                325                 330                 335

Ala Tyr Asp Thr Ala Ser Ala Glu Arg Arg Leu Ser Gly Thr Pro Ile
            340                 345                 350

Ser Phe Ile Leu Leu Leu Ser Tyr Thr Ser Ser Cys Val Asn Pro Ile
    355                 360                 365

Ile Tyr Cys Phe Met Asn Lys Arg Phe Arg Leu Gly Phe Met Ala Thr
370                 375                 380

Phe Pro Cys Cys Pro Asn Pro Gly Pro Pro Gly Ala Arg Gly Glu Val
385                 390                 395                 400

Gly Glu Glu Glu Glu Gly Gly Thr Thr Gly Ala Ser Leu Ser Arg Phe
                405                 410                 415
```

```
Ser Tyr Ser His Met Ser Ala Ser Val Pro Pro Gln
            420                 425
```

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:32:

```
CGTTCTTTCT TCTCTGCCTC C                                          21
```